(12) United States Patent
Kichler et al.

(10) Patent No.: US 9,175,055 B2
(45) Date of Patent: Nov. 3, 2015

(54) USE OF FIBROMODULIN AND LUMICAN FOR INCREASING MUSCLE MASS

(71) Applicant: ASSOCIATION FRANCAISE CONTRE LES MYOPATHIES, Paris (FR)

(72) Inventors: Antoine Kichler, Mennecy (FR); Daniel Scherman, Paris (FR)

(73) Assignee: ASSOCIATION FRANCAISE CONTRE LES MYOPATHIES, Paris (FR)

( * ) Notice: Subject to any disclaimer, the term of this patent is extended or adjusted under 35 U.S.C. 154(b) by 0 days.

(21) Appl. No.: 14/357,971

(22) PCT Filed: Oct. 15, 2012

(86) PCT No.: PCT/FR2012/052349
§ 371 (c)(1),
(2) Date: May 13, 2014

(87) PCT Pub. No.: WO2013/072587
PCT Pub. Date: May 23, 2013

(65) Prior Publication Data
US 2014/0323400 A1    Oct. 30, 2014

(30) Foreign Application Priority Data
Nov. 18, 2011 (FR) .................................. 11 60533

(51) Int. Cl.
| | | |
|---|---|---|
| A61P 21/00 | (2006.01) | |
| A61P 21/06 | (2006.01) | |
| A61K 38/17 | (2006.01) | |
| A61K 38/10 | (2006.01) | |
| C07K 14/47 | (2006.01) | |
| C07K 9/00 | (2006.01) | |
| C07K 14/705 | (2006.01) | |
| C07K 7/08 | (2006.01) | |

(52) U.S. Cl.
CPC .............. *C07K 14/4725* (2013.01); *A61K 38/10* (2013.01); *A61K 38/177* (2013.01); *C07K 9/00* (2013.01); *A61K 38/1709* (2013.01); *C07K 7/08* (2013.01); *C07K 14/705* (2013.01)

(58) Field of Classification Search
None
See application file for complete search history.

(56) References Cited

U.S. PATENT DOCUMENTS

2012/0058955 A1*    3/2012    Kichler et al. ............... 514/20.9

FOREIGN PATENT DOCUMENTS

| WO | 2004/058988 A2 | 7/2004 |
| WO | 2005/094446 A2 | 10/2005 |
| WO | 2008/030706 A2 | 3/2008 |
| WO | 2010/106295 A1 | 9/2010 |
| WO | 2010/138637 A2 | 12/2010 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Antonsson et al., "Structure and deduced amino acid sequence of the human fibromodulin gene," *Biochim Biophys Acta* 1174(2):204-206 (1993) (Abstract).
Chakravarti et al., "Primary Structure of Human Lumican (Keratan Sulfate Proteoglycan) and Localization of the Gene (LUM) to Chromosome 12q21.3-q22," *Genomics* 27:481-488 (1995).
Guiraud et al., "Identification of decorin derived peptides with a zinc dependent anti-myostatin activity," *Neuromascular Disorders* 22:1057-1068 (2012).
Grover et al., "The human lumican gene. Organization, chromosomal location, and expression in articular cartilage," *J Biol Chem* 270(37):21942-21949 (1995) (Abstract).
Dennler et al., "Direct binding of Smad3 and Smad4 to critical TGF beta-inducible elements in the promoter of human plasminogen activator inhibitor-type 1 gene," *Embo J* 17(11):3091-3100 (1998) (Abstract).
Kishioka et al., "Decorin Enhances the Proliferation and Differentiation of Myogenic Cells Through Suppressing Myostatin Activity," *Journal of Cellular Physiology* pp. 856-867 (2007).
Kurisaki et al., "Nuclear factor YY1 inhibits transforming growth factor beta- and bone morphogenetic protein-induced cell differentiation," *Mol Cell Biol* 23(13):4494-4510 (2003) (Abstract).
McEwan et al., "Structural correlations in the family of small leucine-rich repeat proteins and proteoglycans," *J Struct Biol* 155(2):294-305 (2006) (Abstract).
McNally et al., "Muscle diseases: the muscular dystrophies," *Annu Rev Pathol* 2:87-109 (2007) (Abstract).
Miura et al., "Decorin binds myostatin and modulates its activity to muscle cells," *Biochemical and Biophysical Research Communications* 340:675-680 (2006).
Miura et al., "Interaction between myostatin and extracellular matrix components," *Animal Science Journal* 81:102-107, (2009).
Säämänen et al., "Murine fibromodulin: cDNA and genomic structure, and age-related expression and distribution in the knee joint," *Biochem J* 355(Pt 3):577-585 (2001).
Winokur et al., "Facioscapulohumeral muscular dystrophy (FSHD) myoblasts demonstrate increased susceptibility to oxidative stress," *Neuromuscular Disorders* 13:322-333 (2003).
XP-002694351 "Human cancer associated protein sequence SEQ ID No. 948," AAB43503 (2 pages) (Feb. 8, 2001).
Ying et al., "Characterization and expression of the mouse lumican gene," *J Biol Chem* 272(48):30306-30313 (1997).

* cited by examiner

*Primary Examiner* — Zachary Howard
(74) *Attorney, Agent, or Firm* — Seed IP Law Group PLLC

(57) ABSTRACT

The invention relates to the use of fibromodulin and lumican, particularly active fragments thereof, to increase muscle mass, especially in the treatment of muscular dystrophies.

14 Claims, 2 Drawing Sheets

USE OF FIBROMODULIN AND LUMICAN FOR INCREASING MUSCLE MASS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120220_401USPC_SEQUENCE_LISTING.txt. The text file is 117 KB, was created on May 8, 2014, and is being submitted electronically via EFS-Web.

TECHNICAL DOMAIN

The invention herein aims at augmenting the muscular mass in man or animals.

More precisely, it recommends the use of fibromodulin and lumican—in particular, a fraction of these proteins able to bind myostatin, to develop muscular mass and, notably, to treat pathological conditions associated with a muscular wasting, such as muscular dystrophies, and even non-pathological conditions such as muscular waste linked to aging.

PRIOR STATE OF THE ART

Neuromuscular diseases include various pathologies that are generally associated with a temporary or permanent loss of muscular strength. This loss of strength is usually accompanied by muscular wasting, also referred to amyotrophy.

Among these muscular diseases, myopathies constitute an important group that damage the actual muscular fiber. Among them, progressive muscular dystrophies are characterized in that a decrease in muscular strength with, generally, an atrophy of the muscles, as well as anomalies of the muscular biopsy revealing a change in the tissue. This group notably includes Duchenne muscular dystrophy (or DMD), Becker muscular dystrophy (or DMB) and limb girdle muscular dystrophies.

For some of these diseases, associated genetic abnormalities have been identified. Thus, Duchenne or Becker muscular dystrophies are linked to alterations in the gene encoding dystrophin, limb girdle muscular dystrophy type 2A (LGMD 2A or calpainopathy) with alterations in the calpain 3 gene, or sarcoglycanopathies or girdle myopathies of LGMD 2C, LGMD 2D, LGMD 2E, or LGMD 2F type to defects in the genes of γ-, α-, β- and δ-sarcoglycan, respectively (McNally E M, Pytel P, *Muscle diseases: the muscular dystrophies*. Annu Rev Pathol. 2007; Vol 2:87-109).

In these cases, different therapeutic approaches, including gene therapies, are being developed but are difficult to implement.

However, and more generally in all cases of muscle wasting, there is a clear need to develop technical solutions to increase the mass and/or muscle volume.

Thus, document WO 2005/094 446 identified antibodies directed against a localized epitope between residues 40 and 64 of mature human myostatin that can increase muscle mass. However, this strategy based on the recognition of a myostatin by an antibody is not without its difficulties. There is therefore a need to find alternative solutions.

Furthermore, WO 2010/106295 reports that decorin, particularly its N-terminal zinc-binding region, is a solution for increasing muscle mass. Decorin is a protein of the extracellular matrix belonging to the family of SLRP (Small Leucine-Rich Proteoglycan) and, more specifically, to the class I of SLRPs.

On the structural level, the SLRP protein have in common the possession of leucine-rich sequences (Leucine-Rich Repeat or LRR), cysteine residues conserved in the N-terminal position, and the presence of at least one side chain of glycosaminoglycan (GAG). Five classes SLRPs have been defined, notably on the basis of the pattern containing the cysteine residues (McEwan et al., *Structural correlations in the family of small leucine-rich repeat proteins and proteoglycans*. J. of Struct. Biol. 155(2006) 294-305).

Although the SLRP family proteins have common characteristics, notably structural, their functional involvement remains totally unpredictable. Thus, it has been shown in document Miura et al. (*Decorin binds myostatin and modulates its activity to muscle cells*. Biochemical and Biophysical Research Communications 340 (2006) 675-680) that biglycan, another SRLP of class I like decorin, as having 57% identity therewith, was not capable of binding to myostatin.

DETAILED DESCRIPTION OF THE INVENTION

The present invention forms part of the search for new solutions to increase muscle mass.

Thus, and surprisingly, the Applicant has shown that fibromodulin and lumican, two SRLPs of class II, were able to perform this function. Furthermore, the Applicant has identified fragments of these proteins able to perform that function.

Thus according to a first aspect, the present invention relates to a peptide containing a fragment of fibromodulin or lumican capable of binding myostatin.

In the context of the invention, "fibromodulin" is the generic name given to the protein described, for example, by Antonsson, P. et al. (*Structure and deduced amino acid sequence of the human fibromodulin gene*. Biochim. Biophys. Acta 1174 (2), 204-206 (1993)) ou par Saamanen, A. M., et al. (*Murine fibromodulin: cDNA and genomic structure, and age-related expression and distribution in the knee joint*. Biochem. J. 355 (PT 3), 577-585 (2001)).

Thus the corresponding murine protein has the sequence SEQ ID NO: 6 and subsequent, accessible in GenBank under the number CAA64454.1 (fibromodulin [*Mus musculus*]):

```
  1    mqwasvllla glcslsqgqy dedshwwiqy lrnqqstyyd
       pydpypyeps epypygveeg 61    payaygappp peprdcpqec dcppnfptam ycdnrnlkyl
       pfvpsrmkyv yfqnnqisai 121    qegvfdnatg llwvalhgnq itsdkvgrkv fsklrhlerl
       yldhnnltrm pgplprslre 181    lhldhnqisr vpnnalegle nitalylhhn eiqevgssmr
       glrslilldl synhlrrvpd 241    glpsaleqly lehnnvytvp dsyfrgspkl lyvrlshnsl
       tnnglatntf nsslleldl 301    synqlqkipp vntnlenlyl qgnrinefsi ssfctvvdvm
       nfsklqvlrl dgneikrsam 361    pvdaplclrl anliei
```

The corresponding human protein has the sequence SEQ ID NO: 7 and subsequent, accessible in GenBank under the number CAA51418.1 (fibromodulin [Homo sapiens]):

```
  1  mqwtslllla  glfslsqaqy  eddphwwfhy  lrsqqstyyd
     pydpypyety  epypygvdeg 61  paytygspsp  pdprdcpqec  dcppnfptam  ycdnrnlkyl
     pfvpsrmkyv  yfqnnqitsi 121  qegvfdnatg  llwialhgnq  itsdkvgrkv  fsklrhlerl
     yldhnnltrm  pgplprslre 181  lhldhnqisr  vpnnalegle  nitalylqhn  eiqevgssmr
     glrslylldl  synhlrkvpd 241  glpsaleqly  mehnnvytvp  dsyfrgapkl  lyvrlshnsl
     tnnglasntf  nsssllelddl 301  synqlqkipp  vntnlenlyl  qgnrinefsi  ssfctvvdvv
     nfsqlqvvrl  dgnemkrsam 361  paeaplclrl  asliei
```

Similarly, we give the generic name "lumican" to the protein described, for example, by Grover, J. et al. (The human lumican gene. Organization, chromosomal location, and expression in articular cartilage. *J. Biol. Chem.* 270 (37), 21942-21949 (1995)) ou Ying, S. et al. (Characterization and expression of the mouse lumican gene. *J. Biol. Chem.* 272 (48), 30306-30313 (1997)).

The corresponding murine protein has the sequence SEQ ID NO: 8 and subsequent, accessible in GenBank under the number AAB87767.1 (lumican [*Mus musculus*]):

```
  1  mnvcafslal  alvgsysgqy  ydydiplfmy  gqispncape
     cncphsypta  mycddlklks 61  vpmvppgiky  lylrnnqidh  idekafenvt  dlqwlildhn
     llenskikek  vfsklkqlkk 121  lhinynnlte  svgplpkslq  dlqltnnkis  klgsfdglvn
     ltfiylqhnq  lkedavsasl 181  kglksleyld  lsfnqmsklp  aglptslltl  yldnnkisni
     pdeyfkrftg  lqylrlshne 241  ladsgvpgns  fnisslleld  lsynklksip  tvnenlenyy
     levnelekfd  vktfckilgp 301  lsyskikhlr  ldgnpltqss  lppdmyeclr  vaneitvn
```

The corresponding human protein has the sequence SEQ ID NO: 9 and subsequent, accessible in GenBank under the number AAA85268.1 (lumican [*Homo sapiens*]):

```
  1  mslsaftlfl  aliggtsgqy  ydydfppsiy  gqsspncape
     cncpesypsa  mycdelklks 61  vpmvppgiky  lylrnnqidh  idekafenvt  dlqwlildhn
     vlenskikgr  vfsklkqlkk 121  lhinhnnlte  svgplpksle  dlqlthnkit  klgsfeglvn
     ltfihlqhnr  lkedavsaaf 181  kglksleyld  lsfnqiarlp  sglpvslltl  yldnnkisni
     pdeyfkrfna  lqylrlshne 241  ladsgipgns  fnvsslveld  lsynklknip  tvnenlenyy
     levnqlekfd  iksfckilgp 301  lsyskikhlr  ldgnrisets  lppdmyeclr  vanevtln
```

In the context of the invention, fibromodulin or lumican can come from any organism, but proteins of human origin or murine are preferred. More generally and advantageously, the protein will come from the same organism as that in which it will be administered. One of the advantages of the solutions proposed in the context of the present invention is that these are naturally-occurring proteins in mammals, especially humans, and therefore a priori not likely to cause side effects or immune responses.

Although these proteins in their natural state have a chain glycosaminoglycan (GAG), a protein devoid of GAG (GAG-) may also be used within the scope of the invention. This can for example be obtained by enzymatic treatment.

In the context of the invention, the term peptide or polypeptide means a molecule incorporating less than 100 amino acids or residues or, advantageously, less than 50 or less than 40 amino acids, or even less than 35 or even less than 30 amino acids.

According to a first definition, the peptide covered by the invention is characterized in that its ability to bind myostatin. This binding can be assessed by different methods, direct or indirect, known to those skilled in the art: by surface plasmon resonance (Miura et al, 2006.) with a plasmid encoding for a reporter gene such as luciferase and containing sequences called CAGA (plasmid called here p(CACA) 12-Luc) (Dennler S, Itoh S, Vivien D, ten Dijke P, Huet S, Gauthier J M. *Direct binding of Smad3 and Smad4 to critical TGF beta-inducible elements in the promoter of human plasminogen activator inhibitor-type 1 gene.* Embo J. 1998; 17:3091-100; Kurisaki K, Kurisaki A, Valcourt U, Terentiev A A, Pardali K, Ten Dijke P, et al. *Nuclear factor YY1 inhibits transforming growth factor beta-and bone morphogenetic protein-induced cell differentiation.* Mol Cell Biol. 2003 23:4494-510); by the execution of an ELISA test (see the examples of implementation below); . . .

It is known that these two SLRP proteins are a first subfamily of class II that has, in the N-terminal domain, a cysteine-rich consensus region, sequence $CX_3CXCX_9C$ (C represents a cysteine residue and X an amino acid; in other words: a cysteine followed by 3 aa followed by a cysteine separated by an aa of another cysteine, itself separated by 9 aa from the last cysteine).

Advantageously, and with regard to the fibromodulin, a peptide covered includes the sequence CPQECDCPPNF-PTAMYC (SEQ ID NO: 1). In other words, the peptide incorporates a fragment of fibromodulin corresponding to residues 76 to 92 of murine fibromodulin (SEQ ID NO: 6).

According to a preferred embodiment, the peptide incorporates or consists of the sequence PPPEPRD CPQECDCP-PNFPTAMYC DNRNLKYLP (SEQ ID NO: 2). In other words, the peptide incorporates or is composed of a fragment of fibromodulin corresponding to residues 69-101 of murine fibromodulin (SEQ ID NO: 6).

The peptide corresponding to residues 69 to 101 of human fibromodulin (SEQ ID NO: 7) has the sequence SEQ ID NO: 10 following: SPPDPRDCPQECDCPPNFPTAMYCDN-RNLKYLP Advantageously, and with regard to the lumican, a peptide covered includes the sequence CAPECNCPHSYPTAMYC (SEQ ID NO): 4) corresponding to residues 37 to 53 of murin lumican (SEQ ID NO: 8) or the CAPECNCPESYPSAMYC sequence (SEQ ID NO: 11) corresponding to residues 37 to 53 of human lumican (SEQ ID NO: 9).

According to a preferred implementation, the peptide incorporates or consists of the sequence YGQISPNCAPEC-NCPHSYPTAMYCDDLKLKSVP (SEQ ID NO: 5) corresponding to residues 30 to 62 of murin lumican (SEQ ID NO: 8) or the sequence YGQSSPNCAPECNCPESYPSAMYC DELKLKSVP (SEQ ID NO: 12) corresponding to residues 30 to 62 of human lumican (SEQ ID NO: 9).

The peptides described above are defined by their sequence and their ability to bind myostatin. The remainder of the peptide sequence can correspond to the amino acid juxtaposing the fragment identified in the context of the native protein, in which case the peptide is composed of a fragment of fibromodulin or lumican properly speaking. Alternatively, it may be a heterologous sequence, that is to say one which does not juxtapose the fragment in the native protein (e.g., addition of one or several PBA sequences) or that is not derived from these proteins (e.g. TAG sequences), in which case the peptide is a peptide variant or chimeric peptide.

Furthermore, the peptide according to the invention may undergo chemical changes, such as grafting of a biotin (biotinylated), or any other modification that does not impair its properties of binding to myostatin (linking of polyethylene glycol moiety, incorporation of unnatural amino acids, phosphorylation, methylation, etc.).

The peptides according to the invention have a large number of applications, particularly including:
 the detection, purification and/or titration of myostatin, particularly in vitro;
 combating muscle wasting and, therefore, the treatment of pathologies associated with muscle-wasting;
 increasing muscle mass.

In the context of the invention, the term "muscle mass" could be replaced by either muscle weight or muscle volume.

There are a number of conditions in which muscle wasting occurs.

They can first of all be pathological conditions, especially in the case of neuromuscular diseases. Muscle wasting is a direct consequence of neuromuscular diseases, and it is then a compensatory approach. In this context, Duchenne muscular dystrophy is a pathology particularly targeted, but all forms of neuromuscular diseases, especially muscular dystrophies, can be treated.

In addition, cachexia or marasmus is also a medical condition covered by this invention. This condition is characterized in that extreme thinness, particularly in muscle, caused by a long illness or an inadequate protein or caloric intake.

This condition is particularly observed in cases of chronic diseases such as cancer or AIDS, or people suffering from either heart failure—there is a skeletal muscle atrophy in 68% of patients—or urinary incontinence.

Without being considered pathological as such, some situations are associated with muscle wasting: aging, prolonged immobilization, etc. There is therefore an advantage in increasing the muscle mass.

In addition, particularly in the agro-foods sector, the invention provides the ability to increase the production of animal meat. Use of fibromodulin or lumican, or at least an active fragment of these proteins, is therefore of particular interest in animals.

The use of a peptide, instead of the corresponding protein, has certain advantages, particularly in terms of its production but also concerning possible adverse in vivo interference risks. However, for the first time, and unexpectedly, it is shown in the context of the present invention that lumican might also be successfully used in the above applications.

Also covered by the present invention are active derivatives (or functional equivalents) of lumican and fragments of fibromodulin or lumican. The activity covered that must have these derivatives concerns the ability to bind myostatin and/or the ability to augment muscle mass, which can be easily evaluated through the use of the tests described in this application or otherwise described in the literature.

In practice, the compounds advantageously have a 50% identity with one of the sequences SEQ ID NO: 1 to 2 and 4 to 12, still more preferably 60, 70%, 80%, 90% or 95% identity, and retaining their ability to bind to myostatin.

The proteins or peptides of the invention may also be in the form of protein/peptide fusion on chimeric protein/peptide, with another group (protein fragment or whatever) at their terminal N or C extremity. These may, for example—but in a non-limitative manner—increase the residence time of the protein or peptide in the body. Such associations can be obtained either from a recombinant cDNA or by chemical bonding of the two parties.

The present invention is thus based on an exogenous supply of at least a fragment of fibromodulin or lumican. Indeed, the composition covered by the invention incorporates either the protein or the peptide as such, or a system of production of the protein or peptide.

With regard to the protein, it can be the native protein purified from an organism that naturally produces this protein, or a recombinant protein produced using any of the synthetis systems available and known to an appropriately-knowledgeable professional. A peptide according to the invention can be chemically synthesized or produced from a cellular, acellular or other synthesis system.

Alternatively, a nucleic acid sequence encoding for said protein or peptide is placed in an expression system, preferably under the control of a promoter in a vector. After introduction into the body, the protein or peptide is produced in vivo. The transfer of nucleic acids (DNA or RNA) can be achieved either with viral approaches to gene transfer (e.g. adeno-associated viruses or AAVs), or with non-viral approaches (e.g. by a single intramuscular injection of a plasmid). For the protein, a genomic DNA can have an interest since, in some cases, the presence of introns stabilizes the pre-spliced mRNA and improves its stability within the core, and its exportation, which leads to a better protein expression.

The proteins and peptides that are advantageous according to the invention can be provided in the form of nucleic acids, notably DNA or RNA, in particular coding for the sequences SEQ ID NO: 1, 2, and 4 to 12, advantageously 1,2, 4, 5, 8, 9, 10, 11 and 12.

According to another preferred form of implementation, the composition covered by the invention also includes zinc, for example, in the form of zinc chloride, at a concentration advantageously between 1 and 50 µM or equal to 15 µM.

Such a composition may further contain any acceptable compound or excipient, notably pharmaceutical. The route of administration can be both intramuscular and intravenous, or subcutaneous, intraperitoneal or oral.

To facilitate the engraftment of stem cells or precursor cells, it may be advantageous to combine the administration of the composition according to the invention with the transplantation of cells (myoblasts, stem cells, etc.). This administration may be simultaneous or staggered in time.

It may also be advantageous to combine a gene therapy for the treatment of a neuromuscular disease, with administration of the composition according to the invention. Thus and according to a preferred implementation, a therapeutic gene is associated with the treatment with the aforesaid composition. The administration of the two treatments may be simultaneous or staggered in time.

The advantageous effects of fragments of fibromodulin or lumican identified in the context of the present invention give rise to an increase in muscle volume (or mass or weight). These positive effects can be observed for different skeletal muscles, both in an organism suffering from a pathology of the muscle mass, and in a healthy individual. A priori, no side effects and no immunological reaction is to be feared.

Furthermore, the present invention highlights the fact that other proteins of the extracellular matrix of the family of SLRPs, other than the decorin already described, are capable of binding myostatin and having a positive impact on muscle mass.

Thus, these proteins and the fragments thereof, which are capable of binding myostatin, also form part of the invention:

1/Class I of SLRPs:

A protein and a peptide of class I, incorporating a sequence $CX_3CXCX_6C$ (SEQ ID NO: 76)(C represents a cysteine residue and X an amino acid; in other words: a cysteine followed by any 3 aa then a cysteine separated by an aa of another cysteine, itself separated from the 6 aa of the last cysteine) and capable of binding myostatin, are covered. Advantageously, it is not decorin or a fragment of decorin.

In particular, it can be asporine (murine and human sequences SEQ ID NO: 13 and 14, respectively) or a peptide incorporating the CPFGCQCYSRVVHC (SEQ ID NO: 15) and, more precisely, incorporating or consisting of the sequence PVNPFFPFDLFPT CPFGCQCYSRVVHC SDLGLTSVP (SEQ ID NO: 16) corresponding to 55-90 of the murine asporine or the sequence PRSHFFPFDLFPM CPFGCQCYSRVVHC SDLGLTSVP sequence (SEQ ID NO: 17) corresponding to fragment 62-97 of human asporine.

The corresponding murine protein has the sequence SEQ ID NO: 13 and subsequent, accessible in GenBank under the number AAI45905.1 (Asporin [*Mus musculus*]):

```
  1  mkeyvmllll  avcsakpffs  pshtalknmm  lkdmedtddd
     dndddnslf   ptkepvnpff
 61  pfdlfptcpf  gcqcysrvvh  csdlgltsvp  nnipfdtrmv
     dlqnnkikei  kendfkglts
121  lyalilnnnk  ltkihpktfl  ttkklrrlyl  shnqlseipl
     nlpkslaelr  ihdnkvkkiq
181  kdtfkgmnal  hvlemsanpl  enngiepgaf  egvtvfhiri
     aeakltsipk  glpptllelh
241  ldfnkistve  ledlkryrel  qrlglgnnri  tdiengtfan
     iprvreihle  hnklkkipsg
301  lqelkylqii  flhynsiakv  gvndfcptvp  kmkkslysai
     slfnnpmkyw  eiqpatfrcv
361  lgrmsvqlgn  vgk
```

The corresponding human protein has the sequence SEQ ID NO: 14 and subsequent, accessible in GenBank under the number AAK35161.1 (asporin precursor [*Homo sapiens*]):

```
  1  mkeyvlllfl  alcsakpffs  pshialknmm  lkdmedtddd
     dddddddddd  dednslfptr
 61  eprshffpfd  lfpmcpfgcq  cysrvvhcsd  lgltsvptni
     pfdtrmldlq  nnkikeiken
121  dfkgltslyg  lilnnnkltk  ihpkaflttk  klrrlylshn
     qlseiplnlp  kslaelrihe
181  nkvkkiqkdt  fkgmnalhvl  emsanpldnn  giepgafegv
     tvfhiriaea  kltsvpkglp
241  ptllelhldy  nkistveled  fkrykelqrl  glgnnkitdi
     engslanipr  vreihlennk
301  lkkipsglpe  lkylqiiflh  snsiarvgvn  dfcptvpkmk
     kslysaislf  nnpvkywemq
361  patfrcvlsr  msvqlgnfgm
```

2/Class II of SLRPs:

A protein and a peptide of class II, incorporating a sequence $CX_3CXCX_9C$ (SEQ ID NO: 77)(C represents a cysteine residue and X an amino acid; in other words: a cysteine followed by any 3 aa then a cysteine separated by an aa of another cysteine, itself separated from the 9 aa of the last cysteine) and capable of binding myostatin, are covered.

Apart from fibromodulin and lumican, it can be osteoadherin (murine and human sequences SEQ ID NO: 18 and 19, respectively) or a peptide incorporating the sequence of morin origin CAKECFCPTNFPTSMYC (SEQ ID NO: 20) or the sequence of human origin CVSECFCPTNFPSSMYC (SEQ ID NO: 21) and, more precisely, incorporating or consisting of the sequence YGVPFYNNILGCAKECFCPTNF-PTSMYCDNRKLKTIP (SEQ ID NO: 22) corresponding to fragment 51-87 of murine osteoadherin or the sequence YGVPFHQYTLGCVSECFCPTNFPSSMYCDNRKLKTIP (SEQ ID NO: 23) corresponding to fragment 51-87 of human osteoadherin.

The corresponding murine protein has the sequence SEQ ID NO: 18 and subsequent, accessible in GenBank under the number NP_036180.1 (osteoadherin (osteomodulin) precursor [*Mus musculus*]):

```
  1  mgflspiyvl  ffcfgvrvyc  gyeayrwddd  ydgepnedyd
     pefgfhqnie  ygvpfynnil
 61  gcakecfcpt  nfptsmycdn  rklktipiip  mhiqqlnlqf
     ndieavtans  finathlkei
121  nlshnkiksq  kidygvfakl  snlqqlhleh  nnleefpfpl
     pkslerlllg  yneisilptn
181  amdglvnvtm  ldlcynhlsd  smlkektlsk  meklmqlnlc
     nnrlesmplg  lpsslmylsl
241  ennsissipd  nyfdklpklh  alrishnkle  dipydifnls
     nlielnvghn  klkqafyipr
301  nlehlylqnn  eiesinvtmi  cpspdpvhhh  hltylrvdqn
     klkepissyi  ffcfprihsi
361  yygeqrstng  etiqlktqvf  rsyqeeeeed  dhdsqdntle
     gqevsdehyn  shyyemqewq
421  dti
```

The corresponding human protein has the sequence SEQ ID NO: 19 and subsequent, accessible in Swiss-Prot under the number Q99983.1 (human Osteoadherin; Precursor):

```
  1  mgflspiyvi  ffffgvkvhc  qyetyqwded  ydqepdddyq
     tgfpfrqnvd  ygvpfhqytl
 61  gcvsecfcpt  nfpssmycdn  rklktipnip  mhiqqlylqf
     neieavtans  finathlkei
121  nlshnkiksq  kidygvfakl  pnllqlhleh  nnleefpfpl
     pkslerlllg  yneisklqtn
181  amdglvnltm  ldlcynylhd  sllkdkifak  meklmqlnlc
     snrlesmppg  lpsslmylsl
241  ennsissipe  kyfdklpklh  tlrmshnklq  dipynifnlp
     nivelsvghn  klkqafyipr
301  nlehlylqnn  eiekmnltvm  cpsidplhyh  hltyirvdqn
     klkepissyi  ffcfphihti
361  yygeqrstng  qtiqlktqvf  rrfpddddes  edhddpdnah
     espeqegaeg  hfdlhyyenq
421  e
```

Alternatively, it can be PRELP (murine and human sequences SEQ ID NO: 24 and 25, respectively) or a peptide incorporating the sequence CYCPPDFPSALYC (SEQ ID NO: 26) and, more precisely, incorporating or consisting of the sequence PPSVFPDCPRECYCPPDFPSALYCDSRNLRRVP (SEQ ID NO: 27) corresponding to fragment 62-94 of murine PRELP or the sequence PPSIFPDCPRECYCPPDFPSALYCDSRNLRKVP (SEQ ID NO: 28) corresponding to fragment 66-98 of human PRELP.

The corresponding murine protein has the sequence SEQ ID NO: 24 and subsequent, accessible in GenBank under the number AAF72994.2 (PRELP [*Mus musculus*]):

```
  1 mrasffwllp lllilasvaq gqptrpkpgi rrkpkprptp
    rfpqapepae ptdlppplpp 61 gppsvfpdcp recycppdfp salycdsrnl rrvpvippri
    hylylqnnfi telplesfqn 121 atglrwvnld nnrirkvdqr vlgklpslaf lymeknqlee
    vpsalprnle qlrlsqnlis 181 rippgvfskl enllllldlqh nrlsdgvfka dtfqglknlm
    qlnlahnilr kmppkvpqai 241 hqlyldsnki etipngyfkd fpnlafirmn ynklsdrglp
    knsfnisnll vlhlshnkis 301 nvpaisnkle hlylnnnsie kingtqicpn nlvafhdfss
    dlenvphlry lrldgnflkp 361 pipldlmmcf rllqsvvi
```

The corresponding human protein has the sequence SEQ ID NO: 25 and subsequent, accessible in GenBank under the number CAG47066.1 (PRELP [*Homo sapiens*]):

```
  1 mrsplcwllp llilasvaqg qptrrprpgt gpgrrprprp
    rptpsfpqpd epaeptdlpp 61 plppgppsif pdcprecycp pdfpsalycd srnlrkvpvi
    pprihylylq nnfitelpve 121 sfqnatglrw inldnnrirk idqrvleklp glvflymekn
    qleevpsalp rnleqlrlsq 181 nhisrippgv fsklenllll dlqhnrlsdg vfkpdtfhgl
    knlmqlnlah nilrkmpprv 241 ptaihqlyld snkietipng yfksfpnlaf irlnynkltd
    rglpknsfni snllvlhlsh 301 nrissvpain nrlehlylnn nsiekingtq icpndlvafh
    dfssdlenvp hlrylrldgn 361 ylkppipldl mmcfrllqsv vi
```

3/Class III of SLRPs:

A protein and a peptide of class II, incorporating a sequence $CX_2CXCX_6C$ (SEQ ID NO: 78)(C represents a cysteine residue and X an amino acid; in other words: a cysteine followed by any 2 aa then a cysteine separated by an aa of another cysteine, itself separated from the 6 aa of the last cysteine) and capable of binding myostatin, are covered.

It can be epyphican (murine and human sequences SEQ ID NO: 29 and 30, respectively) or a peptide incorporating the CLLCTCISTTVYC (SEQ ID NO: 31) and, more precisely, incorporating or consisting of the sequence TNEDFPTCLLCTCISTTVYCDDHELDAIP (SEQ ID NO: 32) corresponding to fragment 111-139 of murin or human epyphican.

The corresponding murine protein has the sequence SEQ ID NO: 29 and subsequent, accessible in GenBank under the number NP_031910.1 (epiphycan precursor [*Mus musculus*]):

```
  1 mgmlarvalg liiidavlaa pttelfnyds evydailedt
    gtfynyehip dnhvenekvs 61 erlsgnrell tpgpqlgdnq dedkdeestp rlidgsspqe
    pefpgllgph tnedfptcll 121 ctcisttvyc ddheldaipp lpkkttyfys rfnrikkink
    ndfaslndlk ridltsnlis 181 eidedafrkl phlqelvlrd nkikqlpelp ntltfidisn
    nrlgrkgikq eafkdmydlh 241 hlyitdnsld hiplplpesl ralhlqnndi lemhedtfcn
    vknityvrka ledirldgnp 301 inlsrtpqay mclprlpigs fi
```

The corresponding human protein has the sequence SEQ ID NO: 30 and subsequent, accessible in GenBank under the number AAH30958.1 (Epiphycan [*Homo sapiens*]):

```
  1 mktlaglvlg lvifdaavta ptlesinyds etydatledl
    dnlynyenip vgkveieiat 61 vmpsgnrell tpppqpekaq eeeeeeestp rlidgsspqe
    peftgvlgph tnedfptcll 121 ctcisttvyc ddheldaipp lpkntayfys rfnrikkink
    ndfaslsdlk ridltsnlis 181 eidedafrkl pqlrelvlrd nkirqlpelp ttltfidisn
    nrlgrkgikq eafkdmydlh 241 hlyltdnnld hiplplpenl ralhlqnnni lemhedtfcn
    vknltyirka ledirldgnp 301 inlsktpqay mclprlpvgs lv
```

Alternatively, it can be osteoglycin (murine and human sequences SEQ ID NO: 33 and 34, respectively) or a peptide incorporating the sequence CLLCVCLSGSVYC (SEQ ID NO: 35) and, more precisely, incorporating or consisting of the sequence KENDEMPTCLLCVCLSGSVYCEEVDIDAVP (SEQ ID NO: 36) corresponding to fragment 86-115 of morin or human osteoglycin.

The corresponding murine protein has the sequence SEQ ID NO: 33 and subsequent, accessible in GenBank under the number AAH21939.1 (Osteoglycin [*Mus musculus*]):

```
  1 metvhstfll llfvpltqqa pqsqldshvn yeyatgnsee
    tkfsqdyedk yldgksikek 61 etmiipdeks lqlqkdevip slptkkende mptcllcvcl
    sgsvyceevd idavpplpke 121 saylyarfnk ikkltakdfa dmpnlrrldf tgnliedied
    gtfsklslle eltlaenqll 181 rlpvlppklt llnakhnkik skgikantfk klnklsflyl
    dhndlesvpp nlpeslrvih 241 lqfnsisslt ddtfckandt ryirerieei rlegnpialg
    khpnsficlk rlpigsyf
```

The corresponding human protein has the sequence SEQ ID NO: 34 and subsequent, accessible in GenBank under the number AAH37273.1 (Osteoglycin [*Homo sapiens*]):

```
  1 mktlqstlll lllvplikpa pptqqdsrii ydygtdnfee
    sifsqdyedk yldgknikek 61 etviipneks lqlqkdeait plppkkende mptcllcvcl
    sgsvyceevd idavpplpke
```

```
121   saylyarfnk  ikkltakdfa  dipnlrrldf  tgnliedied
      gtfsklslle  elslaenqll 181   klpvlppklt  lfnakynkik  srgikanafk  klnnltflyl
      dhnalesvpl  nlpeslrvih 241   lqfnniasit  ddtfckandt  syirdrieei  rlegnpivlg
      khpnsficlk  rlpigsyf
```

Lastly, It can be opticin (murine and human sequences SEQ ID NO: 37 and 38, respectively) or a peptide incorporating the sequence CLVCVCLGSSVYC (SEQ ID NO: 39) and, more precisely, incorporating or consisting of the sequence NSQSSHGLPTCLVCVCLGSSVYCD-DADLENIP (SEQ ID NO: 40) corresponding to fragment 114-145 of murine opticin or the sequence SSQPNHGLPT-CLVCVCLGSSVYCDDIDLEDIP (SEQ ID NO: 41) corresponding to fragment 118-149 of human opticin.

The corresponding murine protein has the sequence SEQ ID NO: 37 and subsequent, accessible in GenBank under the number AAL78287.1 (opticin [*Mus musculus*]):

```
  1   mkflaflsll  slvlqkaeta  sllgerere  qspeegdtya
      slyvgnhtls  iedynevidl 61   snyeeladyg  dqipeakisn  ltlptrtspt  stvaqktlsp
      nltmavpttt  gllnsqsshg 121   lptclvcvcl  gssvycddad  lenipplpqm  ttylyarfnh
      ishiqagdfk  gltklrridl 181   sgnsissihn  dalrllpalq  dlilpenqla  alpvlpsgie
      fldvrlnrlq  ssgiqpeafv 241   alkklqflyl  annmldsipg  plplslrslh  lqnnmietme
      sdtfcdtgeh  rherrqledi 301   rldgnpinls  lfpeayfclp  rlpvghft
```

The corresponding human protein has the sequence SEQ ID NO: 38 and subsequent, accessible in GenBank under the number AAL78286.1 (opticin [*Homo sapiens*]):

```
  1   mrllaflsll  alvlqetgta  slprkerkrr  eeqmpregds
      fevlplrndv  lnpdnygevi 61   dlsnyeeltd  ygdqlpevkv  tslapatsis  paksttapgt
      pssnptmtrp  ttaglllssq 121   pnhglptclv  cvclgssvyc  ddidledipp  lprrtaylya
      rfnrisrira  edfkgltklk 181   ridlsnnlis  sidndafrll  halqdlilpe  nqlealpvlp
      sgiefldvrl  nrlqssgiqp 241   aaframeklq  flylsdnlld  sipgplplsl  rsvhlqnnli
      etmqrdvfcd  peehkhtrrq 301   ledirldgnp  inlslfpsay  fclprlpigr  ft
```

4/Class IV of SLRPs:

A protein and a peptide of class IV, incorporating a sequence $CX_3CXCX_{6-17}C$ (SEQ ID NO: 76) (C represents a cysteine residue and X an amino acid; in other words: a cysteine followed by any 3 aa then a cysteine separated by an aa of another cysteine, itself separated from the 6 to 17 aa of the last cysteine) and capable of binding myostatin, are covered.

It can be chondroadherin (murine and human sequences SEQ ID NO: 42 and 43, respectively) or a peptide incorporating the sequence of morin origin CPQNCHCHGDLQH-VIC (SEQ ID NO: 44) or the sequence of human origin CPQNCHCHSDLQHVIC (SEQ ID NO: 45) and, more precisely, incorporating or consisting of the sequence LAILL-PALAACPQNCHCHGDLQHVICDKVGLQKIP (SEQ ID NO: 46) corresponding to fragment 12-46 of murine chondroadherin or the sequence LAGLLPALAACPQNCHCHS-DLQHVICDKVGLQKIP (SEQ ID NO: 47) corresponding to fragment 13-47 of human chondroadherin.

The corresponding murine protein has the sequence SEQ ID NO: 42 and subsequent, accessible in GenBank under the number AAC39963.1 (chondroadherin [*Mus musculus*]):

```
  1   marallfslv  flaillpala  acpqnchchg  dlqhvicdkv
      glqkipkvse  ttkllnlqrn 61   nfpvlaansf  rtmpnlvslh  lqhcnireva  agafrglkql
      iylylshndi  rvlragafdd 121   lteltylyld  hnkvselprg  llsplvnlfi  lqlnnnkire
      lragafqgak  dlrwlylsen 181   alsslqpgsl  ddvenlakfh  ldknqlssyp  saalsklrvv
      eelklshnpl  ksipdnafqs 241   fgryletlwl  dntnlekfsd  aafsgvttlk  hvhldnnrln
      qlpssfpfdn  letltltnnp 301   wkctcqlrgl  rrwleakasr  pdatcsspak
      fkgqrirdtd  alrscksptk  rskkagrh
```

The corresponding human protein has the sequence SEQ ID NO: 43 and subsequent, accessible in GenBank under the number AAC13410.1 (chondroadherin [*Homo sapiens*]):

```
  1   mvrpmlllsl  gllagllpal  aacpqnchch  sdlqhvicdk
      vglqkipkvs  ektkllnlqr 61   nnfpvlaans  frampnlvsl  hlqhcqirev  aagafrglkq
      liylylshnd  irvvragafd 121   dlteltylyl  dhnkvtelpr  gllsplvnlf  ilqlnnnkir
      elragpfqga  kdlrwlylse 181   nalsslqpga  lddvenlakf  hvdrnqlssy  psaalsklrv
      veelklshnp  lksipdnafq 241   sfgryletlw  ldntnlekfs  dgaflgvttl  khvhlennrl
      nqlpsnfpfd  sletlaltnn 301   pwkctcqlrg  lrrwleakas  rpdatcaspa  kfkgqhirdt
      dafrsckfpt  krskkagrh
```

Alternatively, it can be nyctalopin (murine and human sequences SEQ ID NO: 48 and 49, respectively) or a peptide incorporating the sequence of murin origin CLRACPAACTCSHVERGCSVRC (SEQ ID NO: 50) or the sequence of human origin CARACPAACACSTVERGCS-VRC (SEQ ID NO: 51) and, more precisely, incorporating or consisting of the sequence YTRATEACLRACPAACTCSH-VERGCSVRCDRAGLQRVP (SEQ ID NO: 52) corresponding to fragment 15-52 of murine nyctalopin or the sequence SAWAVGACARACPAACACSTVERGCS-VRCDRAGLLRVP (SEQ ID NO: 53) corresponding to fragment 20-57 of human nyctalopin.

The corresponding murine protein has the sequence SEQ ID NO: 48 and subsequent, accessible in GenBank under the number AAM47034.1 (nyctalopin [*Mus musculus*]):

```
  1   mlillihavv  fslpytrate  aclracpaac  tcshvergcs
      vrcdraglqr  vpqefpceaa
```

```
 61   sidldrnglr ilgerafgtl pslrrlslrh nnlsfitpga
      fkglprlael rlahngelry 121   lhvrtfaalg rlrrldlaac rlfsvperll aelpalrelt
      afdnlfrrvp galrglanlt 181   hahfersrie avasgsllgm rrlrslslqa nrvravhaga
      fgdcgaledl llndnllatl 241   paaafrglrr lrtlnlggna lgsvarawfs dlaelellyl
      drnsitfvee gafqnlsgll 301   alhlngnrlt vlswaafqpg fflgrlflfr npwrcdcqle
      wlrdwmegsg rvadvacasp 361   gsvagqdlsq vvferssdgl cvdpdelnft tsspgpspep
      vattvsrfss llskllapra 421   pveevanttw elvnvslnds frshavmvfc ykatflftsc
      vllslaqyvv vglqre
```

The corresponding human protein has the sequence SEQ ID NO: 49 and subsequent, accessible in GenBank under the number AAG42685.1 (nyctalopin [*Homo sapiens*]):

```
  1   mkgrgmlvll lhavvlglps awavgacara cpaacacstv
      ergcsvrcdr agllrvpael 61   pceavsidld rnglrflger afgtlpslrr lslrhnnlsf
      itpgafkglp rlaelrlahn 121   gdlrylhart faalsrlrrl dlaacrlfsv perllaelpa
      lrelaafdnl frrvpgalrg 181   lanlthahle rgrieavass slqglrrlrs lslqanrvra
      vhagafgdcg vlehlllndn 241   llaelpadaf rglrrlrtln lggnaldrva rawfadlael
      ellyldrnsi afveegafqn 301   lsgllalhln gnrltvlawv afqpgfflgr lflfrnpwcc
      dcrlewlrdw megsgrvtdv 361   pcaspgsvag ldlsqvtfgr ssdglcvdpe elnlttsspg
      pspepaattv srfssllskl 421   laprvpveea anttgglana slsdslssrg vggagrqpwf
      llascllpsv aqhvvfglqm 481   d
```

Alternatively, it can be tsukushi (murine and human sequences SEQ ID NO: 54 and 55, respectively) or a peptide incorporating the sequence of murin origin CFPGCQ-CEEETFGLFDSFSLIRVDC (SEQ ID NO: 56) or the sequence of human origin CFPGCQCEVETFGLFDSFSL-TRVD (SEQ ID NO: 57) and, more precisely, incorporating or consisting of the sequence RVQTTRPCFPGCQCEEETF-GLFDSFSLIRVDCSSLGPHIVP (SEQ ID NO: 58) corresponding to fragment 14-54 of murine tsukushi or the sequence GAQTTRPCFPGCQCEVETFGLFDSFSL-TRVDCSGLPHIMP (SEQ ID NO: 59) corresponding to fragment 13-53 of human tsukushi.

The corresponding murine protein has the sequence SEQ ID NO: 54 and subsequent, accessible in GenBank under the number BAD98727.1 (Tsukushi [*Mus musculus*]):

```
  1   mlcslfllll avgrvqttrp cfpgcqceee tfglfdsfsl
      irvdcsslgp hivpvpipld 61   tahldlssnr letvnesvla gpgyttlagl dlsynlltsi
      mpsafsrlry lesldlshng 121   laalpaeift ssplsdinls hnrlrevsis aftthsqgra
      lhvdlshnli hrllphpara 181   slpaptiqsl nlswnrfrav pdlrdlplry lsldgnplat
      inpdafmgla glthlslasl 241   qgilhlpphg frelpglqvl dlsgnpklkw agaevfsglg
      llgeldlsgs slvplpemll 301   hhlpalqsys vgqdvqcrrl vregayhrqp gsspkvvlhc
      gdtqesaarg pdil
```

The corresponding human protein has the sequence SEQ ID NO: 55 and subsequent, accessible in GenBank under the number Q8WUA8.3 (Tsukushi [*homo sapiens*]):

```
  1   mpwplllla vsgaqttrpc fpgcqcevet fglfdsfslt
      rvdcsglgph impvpipldt 61   ahldlssnrl emvnesvlag pgyttlagld lshnlltsis
      ptafsrlryl esldlshngl 121   talpaesfts splsdvnlsh nqlrevsvsa ftthsqgral
      hvdlshnlih rlvphptrag 181   lpaptiqsln lawnrlhavp nlrdlplryl sldgnplavi
      gpgafaglgg lthlslaslq 241   rlpelapsgf relpglqvld lsgnpklnwa gaevfsglss
      lqeldlsgtn lvplpeallt 301   hlpalqsvsv gqdvrcrrlv regtyprrpg sspkvalhcv
      dtrdsaargp til
```

5/Class V of SLRPs:

A protein and a peptide of class V, incorporating a sequence $CX_{3-4}CXCX_7C$ (SEQ ID NO: 79) (C represents a cysteine residue and X an amino acid; in other words: a cysteine followed by any 3 or 4 aa then a cysteine separated by an aa of another cysteine, itself separated from the 7 aa of the last cysteine) and capable of binding myostatin, are covered.

It can be podocan (murine and human sequences SEQ ID NO: 60 and 61, respectively) or a peptide incorporating the CPRDCACSQEGVVDC (SEQ ID NO: 62) and, more precisely, incorporating or consisting of the sequence PGPATVDCPRDCACSQEGVVDCGGIDLREFP (SEQ ID NO: 63) corresponding to fragment 62-92 of murine podocan or the sequence PGPAAVSCPRDCACSQEGVVDCG-GIDLREFP (SEQ ID NO: 64) corresponding to fragment 61-91 of human podocan.

The corresponding murine protein has the sequence SEQ ID NO: 60 and subsequent, accessible in GenBank under the number CAM23596.1 (Podocan [*Mus musculus*]):

```
  1   magsrglpll llvlqlflgp vlpvrapvfg rsdtptlspe
      enefveeenq pvlvlsseep 61   epgpatvdcp rdcacsqegv vdcggidlre fpgdlpehtn
      hlslqnnqle kiypeelsrl 121   qrletlnlqn nrltsrglpe eafehltsln ylylannklt
      laprflpnal isvdfaanyl 181   tkiygltfgq kpnlrsvylh nnkladaglp dhmfngssnv
      eililssnfl rhvpkhlppa 241   lyklhlknnk lekippgafs elsnlrelyl qnnyltdegl
      dnetfwklss leyldlssnn 301   lsrvpaglpr slvllhlekn aiqsveadvl tpirnleyll
      lhsnqlqakg ihplafqglk
```

```
361  klhtvhlynn alervpsglp rrvrtlmilh nqitgigred
     fattyfleel nlsynritsp 421  qmhrdafrkl rllrsldlsg nrlqtlppgl pknvhvlkvk
     rnelaalarg alagmaqlre 481  lyltgnrlrs ralgprawvd laglqlldia gnqltevpeg
     lppsleylyl qnnkisavpa 541  nafdstpnlk giflrfnkla vgsvvesafr rlkhlgvldi
     egnfefgngs kdkdeeeeee 601  eeeedeeeet r
```

The corresponding human protein has the sequence SEQ ID NO: 61 and subsequent, accessible in GenBank under the number AAP79898.1 (Podocan [*Homo sapiens*]):

```
  1  maqsrvllll lllppqlhlg pvlavrapgf grsgghslsp
     eenefaeeep vlvlspeepg 61  pgpaavscpr dcacsqegvv dcggidlref pgdlpehtnh
     lslqnnqlek iypeelsrlh 121  rletlnlqnn rltsrglpek afehltnlny lylannkltl
     aprflpnali svdfaanylt 181  kiygltfgqk pnlrsvylhn nkladaglpd nmfngssnve
     vlilssnflr hvpkhlppal 241  yklhlknnkl ekippgafse lsslrelylq nnyltdegld
     netfwklssl eyldlssnnl 301  srvpaglprs lvllhlekna irsvdanvlt pirsleylll
     hsnqlreqgi hplafqglkr 361  lhtvhlynna lervpsglpr rvrtlmilhn qitgigredf
     attyfleeln lsynritspq 421  vhrdafrklr llrsldlsgn rlhmlppglp rnvhvlkvkr
     nelaalarga lagmaqlrel 481  yltsnrlrsr algprawvdl ahlqlldiag nqlteipegl
     pesleylylq nnkisavpan 541  afdstpnlkg iflrfnklav gsvvdsafrr lkhlqvldie
     gnlefgdisk drgrlgkeke 601  eeeeeeeeee etr
```

It can also be podocan-like protein 1 (murine and human sequences SEQ ID NO: 65 and 66, respectively) or a peptide incorporating the sequence of morin origin CPWRCSCPRD-DTVDC (SEQ ID NO: 67) or the sequence of human origin CPLRCSCPRVDTVDC (SEQ ID NO: 68) and, more precisely, incorporating or consisting of the sequence GDSSQ-PLPRPCPWRCSCPRDDTVDCAGLDLRIFP (SEQ ID NO: 69) corresponding to fragment 29-62 of murine podocan-like protein 1 or the sequence GESLQPLLRACPLRC-SCPRVDTVDCDGLDLRVFP (SEQ ID NO: 70) corresponding to fragment 36-69 of human podocan-like protein 1.

The corresponding murine protein has the sequence SEQ ID NO: 65 and subsequent, accessible in NCBI under the number NP_001013402.2 (podocan-like protein 1 precursor [*Mus musculus*]):

```
  1  mrpqelllll lmlkwslaht edpafphlgd ssqplprpcp
     wrcscprddt vdcagldlri 61  fpdnitraar hlslqnnqlr elpynelsrl sglrtldlhs
     nlitseglpd eafeslnqle
```

```
121  nfyvahnkls vapqflprsl rvadlaanev veifpltfge
     kpalrsvylh nnrlrntglp 181  pntfhgsevi ttlslssnql sylppslpas lerlhlqnnl
     iskvprgals lgthlrelyl 241  qhnqltdsgl dattfsklss leyldlshnq latvpeglpg
     tltilhlgrn cirhveavrl 301  hkarglryll lqhnklgasa lpkgtlrplr alhtlhlygn
     klervppalp rhlqalvmph 361  nhvaalgard lvsaralael nlaynslasa hvhpsafrrl
     ralrsldlag nqltrlpegl 421  paslrslrlq rnqlrtlepe qlaglnklre lnlahnrlrv
     gdigpgtwhe lqalkvldls 481  hnelsfvppd lpealeelyl qanrishvgp eaflstphlr
     alflranrlh mtsiraealq 541  glthlrvvdt aenpeqvlv
```

The corresponding human protein has the sequence SEQ ID NO: 66 and subsequent, accessible in GenBank under the number AAH57786.1 (Podocan-like 1 [*Homo sapiens*]):

```
  1  maesglamwp slllllllpg pppvagleda afphlgeslq
     pllracplrc scprvdtvdc 61  dgldlrvfpd nitraaqhls lqnnqlqelp ynelsrlsgl
     rtlnlhnnli sseglpdeaf 121  esltqlqhlc vahnklsvap qflprslrva dlaanqvmei
     fpltfgekpa lrsvylhnnq 181  lsnaglppda frgseaiatl slsnnqlsyl ppslppsler
     lhlqnnlisk vprgalsrqt 241  qlrelylqhn qltdsgldat tfsklhsley ldlshnqltt
     vpaglprtla ilhlgrnrir 301  qveaarlhga rglrylllqh nqlgssglpa galrplrglh
     tlhlygngld rvppalprrl 361  ralvlphnhv aalgardlva tpgltelnla ynrlasarvh
     hrafrrlral rsldlagnql 421  trlpmglptg lrtlqlqrnq lrmlepepla gldqlrelsl
     ahnrlrvgdi gpgtwhelqa 481  lqvrhrlvsh tvprappspc lpchvpnilv sw
```

Lastly, the invention can concern ECM2 (murine and human sequences SEQ ID NO: 71 and 72, respectively) or a peptide incorporating the sequence AVWSPEPCTTCLCSN-GRVLCDETECHPKACP (SEQ ID NO: 73) corresponding to fragment 109-139 of murine ECM2 or the sequence AVWSPEPCTTCLCSDGRVLCDETMCHPQRCP (SEQ ID NO: 74) corresponding to fragment 114-144 of human ECM2.

The corresponding murine protein has the sequence SEQ ID NO: 71 and subsequent, accessible in NCBI under the number NP_001012324.1 (extracellular matrix protein 2 precursor [*Mus musculus*]):

```
  1  mklavlfcfi lliviqtdce rgtrrqrrrm hqrrlrksss
     fhlranrqle vqqttaapda 61  rlptansdys veeniestls nlgvessysv lpgkkgycfv
     kgmimynkav wspepcttcl
```

```
121  csngrvlcde techpkacpy tikpegeccp icsdaeqesi
     nklhkqvppp qmemdqvaik 181  ealqseedee iaeghkehkk etsvptkihg dgerterklr
     pekegrsahq plyhgrreee 241  eskeetereg eeeeeeeeee eedairgdvf rmssrvipgt
     prgrprlprs cslsyrtisc 301  vhadfteipp itapevtnle lvgnsiisip deafnglpnl
     erldlsrnni tssgigpkaf 361  kslkklmrln mdgnnlvhip sdlpstleel kindnnlqai
     dekslsdlnq lvtlelegnn 421  lseinvdpla fqsleslsyl rlgrnkfrii pqglpastee
     lylennqiee iteicfnhtr 481  kitmiilryn kieesriapl awinqenles idlsynklyh
     vpsylpksll hlvlignqid 541  ripgyvfghm qpgleylyls fnrlsddgvd lvsfygayhs
     lrelfldhnd fksippgiqd 601  mkalhflrin nnkirnihpe qicnaeeded salehlhlen
     nyirtreiss yafscirlys 661  sivlkpqhik
```

The corresponding human protein has the sequence SEQ ID NO: 72 and subsequent, accessible in GenBank under the number AAI05959.1 (ECM2 protein [*Homo sapiens*]):

```
  1  mkiavlfcff lliifqtdfg kneeiprkqr rkiyhrrlrk
     sstshkhrsn rqlgipqttv 61  ftpvarlpiv nfdysmeekf esfssfpgve ssynvlpgkk
     ghclvkgitm ynkavwspep 121  cttclcsdgr vlcdetmchp qrcpqtvipe geccpvcsat
     eqreptnllh kqlpppqvgm 181  drivrkealq seedeevkee dteqkretpe srnqgqlyse
     gdsrggdrkq rpgeerrlah 241  qqqrqgreee edeeeegeeg eedeedeedp vrgdmfrmps
     rsplpapprg tlrlpsgcsl 301  syrtiscina mltqipplta pqitsleltg nsiasipdea
     fnglpnlerl dlsknnitss 361  gigpkafkll kklmrsnmdg nnliqipsql pstleelkvn
     ennlqaidee slsdlnqlvt 421  lelegnnlse anvnplafkp lkslaylrlg knkfriipqg
     lpgsieelyl ennqieeite 481  icfnhtrkin vivlrynkie enriaplawi nqenlesidl
     synklyhvps ylpksllhlv 541  llgnqierip gyvfghmepg leylylsfnk laddgmdrvs
     fygayhslre lfldhndlks 601  ippgiqemka lhflrlnnnk irnilpeeic naeedddsnl
     ehlhlennyi kireipsytf 661  scirsyssiv lkpqnik
```

The invention therefore covers:

proteins and peptides, such as defined, and their functional or active variants;

the use of these proteins or peptides for the detection, purification and/or titration of myostatin;

compositions incorporating these proteins or peptides for use in the treatment of pathologies with associated muscle wasting, notably neuromuscular diseases including, advantageously, muscular dystrophies such as Duchenne myopathy and cachexia;

compositions incorporating these proteins or peptides to increase muscle mass, notably to offset the resulting wasting resulting from immobilization, or aging or, in animals:

the presence of zinc in these compositions;

Administration of these compositions by the intramuscular, intraperitoneal, subcutaneous, intravenous or oral path;

the association of these compositions with other treatments such as gene therapy and cell transplantation.

EXAMPLES OF IMPLEMENTATION

The invention and the resulting advantages will come to the fore clearly in the following implementation examples, with reference to the appended Figures. However, the aforesaid Figures have no limitative scope.

The invention is illustrated further on by means of a fragment of fibromodulin or recombinant mouse lumican, tested in vitro for binding to myostatin or intramuscularly injected in mdx mice having a gene encoding an altered dystrophin serving as a model for the study of Duchenne myopathy.

CAPITIONS IN THE FIGURES

I) MATERIALS AND METHODS

Figure 1:
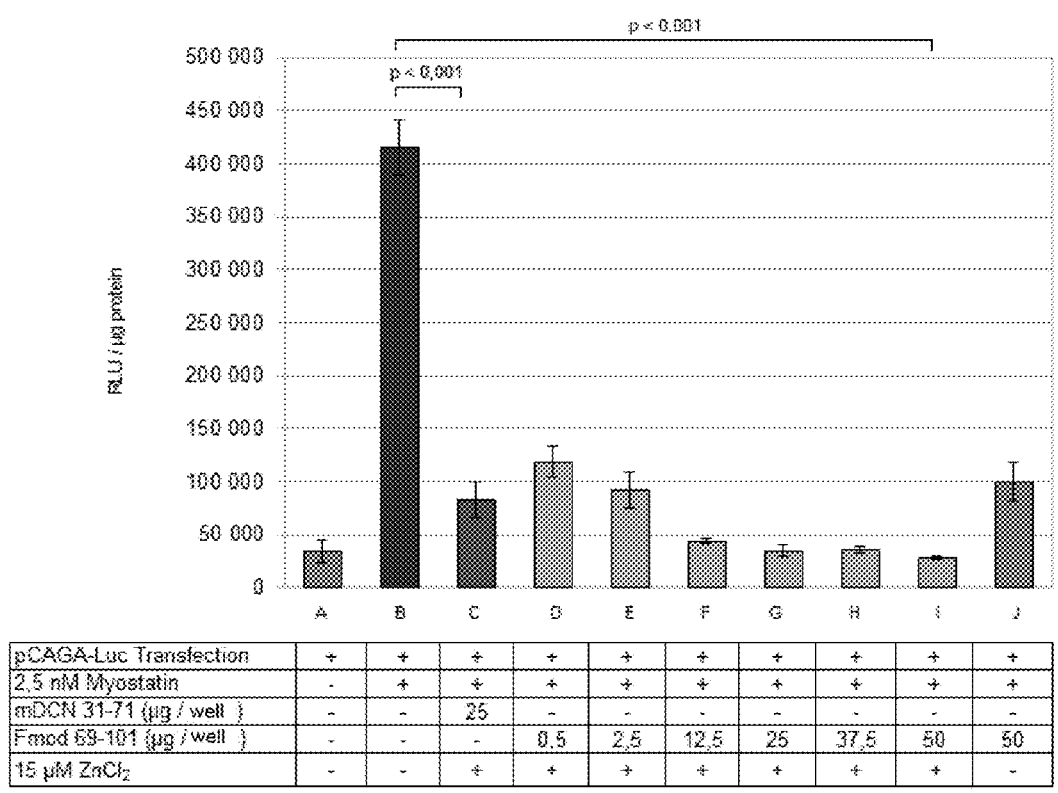
FIG. 1 shows the inhibition of the activity of the myostatin by the murine peptide Fmod 69-101 (SEQ ID NO: 2) in HEK293T cells in vitro in the presence or absence of zinc.

1. Expression Cassette pGL3-(CAGA)$_{12}$-Luc:

The plasmidic construction pGL3-(CAGA)$_{12}$-firefly luciferase (notated pGL3-(CAGA)$_{12}$-Luc) obtained by MTA of the Pr. Carl-Henrik Heldin (Ludwig Institute for Cancer Research, Sweden) contains 12 CAGA copies of the consensus SBE (Smad Binding Element) consensus sequence and allows to indirectly measure the binding of myostatin to its receptor. Indeed, when myostatin binds to the receptor Activin IIb, the Smad 3 and 4 proteins are activated and will bind to the 12 CAGA copies. The promoter of the cassette pGL3-(CAGA)$_{12}$-Luc is thus activated, which results in luciferase production. The myostatin/Activin IIb binding can be followed, therefore, by measuring the luciferase. Accordingly, this test can also be used to demonstrate the ability of a compound (protein or peptide) to prevent binding of myostatin to its receptor.

2. In vitro Study of the Inhibition of Myostatin:

The ability of the peptides to inhibit the in vitro activity of the myostatin has been evaluated on embryonic human kidney cells 293T by means of the pGL3-(CAGA)$_{12}$-Luc construction. For this, 350,000 293T cells were placed per well in a 24-well plate. After 24 hours of culture, the cells were transfected with a mixture of 8 μl de PEI (PEI 25 kDa; Sigma) and 2 μg of plasmide pGL3-(CAGA)$_{12}$-Luc/well. Note that all the transfection experiments were performed in duplicate. Twenty-four hours after transfection, 2.5 nM of recombinant murine myostatin, mixed or not mixed with various quantities of fibromodulin or lumican peptides were added to each well. Prior incubation of 30 minutes at 37° C. was performed for conditions combining myostatin and the potential inhibitor. This pre-incubation—unless otherwise stated—has always performed in the presence of 15 microM of $ZnCl_2$. Twenty-four hours after incubation, the cells were lysed, then collected to be assayed for luciferase activity and the quantity of protein.

The following fibromodulin or lumican peptides were used:

```
for the fibromodulin:
                                            (SEQ ID NO: 2)
Fmod: PPPEPRDCPQECDCPPNFPTAMYCDNRNLKYLP.

for the lumican:
                                            (SEQ ID NO: 5)
mLumican: YGQISPNCAPECNCPHSYPTAMYCDDLKLKSVP.
```

3. Highlighting of the MSTN/Fibromodulin Peptides (Fmod) Binding

The ELISA test (Enzyme Linked ImmunoSorbent Assay) is a test for detecting and/or assaying a protein present in a biological fluid. In the technique known as "sandwich" assay, the wells of a microtiter plate are covered with a capture antibody capable of binding specifically to the desired antigen. During this operation called "coating", the capture antibody binds to the plastic of the wells by electrostatic interaction. The capture antibody ensures the specificity of the test. The solution to be tested is then deposited into the wells of the microtiter plate and, if the desired antigen is present, it will bind specifically to the capture antibody. A second antibody, the tracer antibody, capable of binding to the captured antigen is then added to the wells, and the unbound tracer antibodies are eliminated by rinsing. The tracer antibody is coupled to an enzyme catalyzing the formation of a colored product.

The principle of this technique was used to study the direct interaction of the mature myostatin with the peptides 69-101 Fmod Biotin and 69-101 Fmod Biotin mutated (see sequences below). For this, 3 μl of myostatin at a concentration of 100 ng/μl are taken up in 50 μl of carbonate buffer and added to each well of the assay plate (R&D Systems DY990). After an overnight incubation at 4° C., the plate is washed with 100 μl of PBS-Tween (0.05% Tween 20), then the blocking step to saturate non-specific sites is carried out for 2 hours at room temperature with 100 μl of PBS and 6% of milk per well. Five successive washes with 200 μl of PBS-Tween (0.05% Tween 20) are performed and increasing amounts of biotinylated fibromodulin peptides are then deposited (100 μl final in PBS) and the plate is incubated for 1 hour at 37° C. For the positive control, an antibody of goat anti-myostatin (≠AF788, R&D Systems), which was deposited in the control wells and incubated for 1 hour at $\frac{1}{100}^{th}$ (0.1 mg/ml) was unused. The wells were then washed 5 times with PBS-Tween (0.05% Tween 20). To detect binding of the biotinylated peptides to MSTN, streptavidin-HRP (≠N100, Pierce) was used at $\frac{1}{20,000}^{th}$. was added to the wells. For the controls points with the goat anti-myostatin antibody, an HRP-marked (≠ab6885, Abcam) polyclonal secondary donkey anti-goat antibody was added (at $\frac{1}{4000}^{th}$)). After five washes, adding the peroxidase substrate, the TMB Substrate Reagent Set (Tetramehylbenzidine, OptEIA, ≠555214) allows the obtention of a colored reaction proportional to the quantity of HRP present in the wells. The reaction is stopped after 20 minutes by addition of sulfuric acid 2N, and the plate is read at 450 nm on a Discovery HT-R spectrophotometer (Bio-TEK).

Buffer Composition: 0.1 M carbonate buffer: 4.2 g $NaHCO_3$, 1.78 g of $Na_2CO$ in 500 ml of $H_20$ MilliQ, pH 9,5. Storage at 4° C.

Biotinylated Peptide Sequences:
Biotin-peptide 69-101 mFibromodulin (Fmod)

```
                                            (SEQ ID NO: 2)
Biotine-PPPEPRDCPQECDCPPNFPTAMYCDNRNLK
YLP-CONH2
```

Peptide Biotine-69-101 mFibromodulin mutated (Fmod mutated)

```
                                            (SEQ ID NO: 3)
Biotine-PPPEPRDCPQEADAPPNFPTAMYADNR
NLKYLP- CONH2
```

4. Animal Experimentation:

a. Mice

Mdx mice (C57BL/10ScSn-DmD$^{max}$/J) from colonies maintained at Genethon. Mice aged at least six weeks were used. All experiments were performed in accordance with European ethical rules regarding the use of animals for experimental research.

b. Anesthesia

The mice were anaesthetized prior to each intramuscular injection and prior to each blood collection by an intraperitoneal injection of a mixture of Ketamine 100 mg/kg and xylazine 1 mg/kg (0.1 mL/10 g).

c. Intramuscular Injection

Intramuscular injection is performed on animals anesthetized at the tibialis anterior muscle (TA). The injected volume was around 20-35 μl. The injection is performed in the middle of TA Left (TAG). An equal volume of NaCl 150 mM/15 μM $ZnCl_2$ was systematically injected into the right anterior tibialis (TAD) to serve as a control. After a specified number of days after the injection, the TAD and TAG were taken after sacrificing the mice, which were weighed and frozen for histological studies.

d. Preparation of the Peptide Solution

The peptide fibromodulin (Fmod, SEQ ID NO: 2) and lumican (mLumican, SEQ ID NO: 5) were dissolved in water and stored at −80° C. For the injections, the preparation procedure is as follows: 24-40 hours before the injection, the desired quantity of peptide is removed from the stock solution and mixed with a solution of zinc chloride ($ZnCl_2$) and 150 mM NaCl so as to have a final concentration of 15 μM of zinc. The peptide was stored at 4° C. until injection.

e. Histological Analyses

Laminine Marking:

Cryostat sections (8 microns) of the treated muscles and the controls were carried out according to standard techniques. The slides were fixed with Dakopen (DAKO®, Ref.: S 2002) for 10 minutes in the open air and then blocked with a solution of PBS/10% goat serum for 30 min at room temperature and in a humid chamber. The rabbit anti-laminin antibody (DAKO®, Ref: Z0097) was applied to the slides at a dilution of 1:1000 for 12 hours in a humid chamber. The slides were then rinsed in PBS (5 minutes) with stirring and the secondary antibody (Envision HRP Kit Rabbit) was applied to the slides in a humid chamber for 30 mins at room temperature. After rinsing the slides in PBS (5 minutes) under agitation, DAB (DAKO®, Ref: K 3466) was applied to the sections for 2-5 minutes at room temperature and in a humid chamber. The slides were rinsed in constant renewal and were mounted under the fume hood. Analysis of the results was performed using the ELLIX software.

HPS Marking:

Cryostat sections (8 μm) of the treated muscles and the controls were prepared according to the standard techniques. The slides were dipped in Harris hematoxylin for 3 minutes before being rinsed with running water. They were then soaked in hydrochloric alcohol, rinsed, and immersed in Scott water for one minute. After rinsing, the slides were immersed in Phloxine for 30 seconds, rinsed with running water, and soaked in absolute ethanol for one minute. After exposure to Safran for 3 minutes, they were rinsed with absolute ethanol and mounted with Eukitt resin, of which the solvent is Xylene. Analysis of the results was performed using the CARTOGRAPH software.

II) Results

Figure 2:
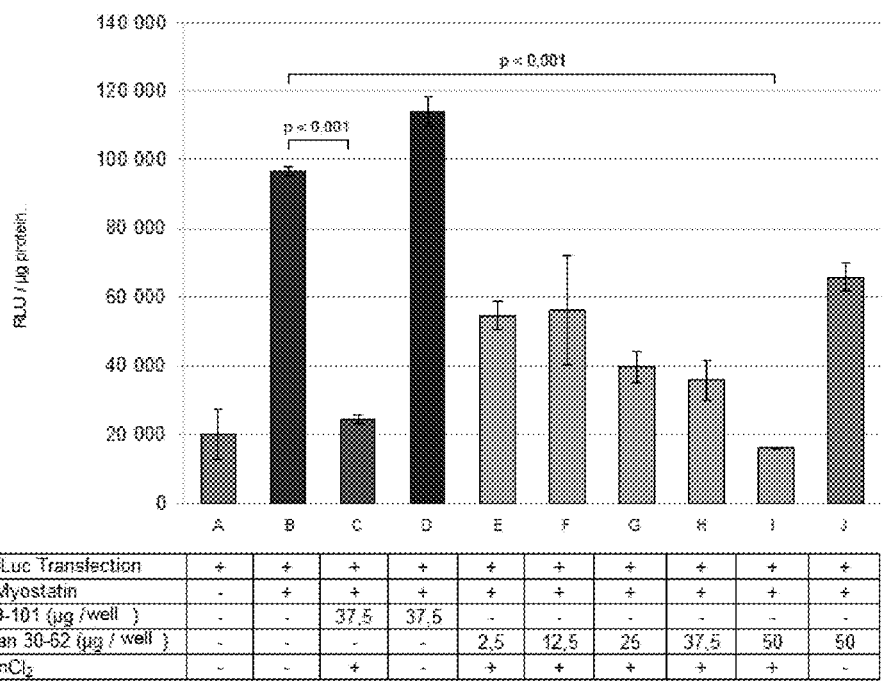
FIG. 2 shows the inhibition of the activity of the myostatin by the murine Lumican peptide 30-62 (SEQ ID NO: 5) in HEK293T cells in vitro in the presence or absence of zinc.

1/Inhibition of Myostatin Activity by the Peptides Fmod 69-101 (SEQ ID NO: 2) and mLum 30-62 (SEQ ID NO: 5) in HEK293T Cells in vitro:

The induction of the pCAGA-Luc promoter was measured as per the instructions for the equipment and methods, and is shown in FIGS. 1 and 2. A net inhibition of the promoter in a dose-dependent manner is observed both with the peptide mFmod 69-101 (FIG. 1), with the peptide mLumican 30-62 (FIG. 2).

Figure 3:
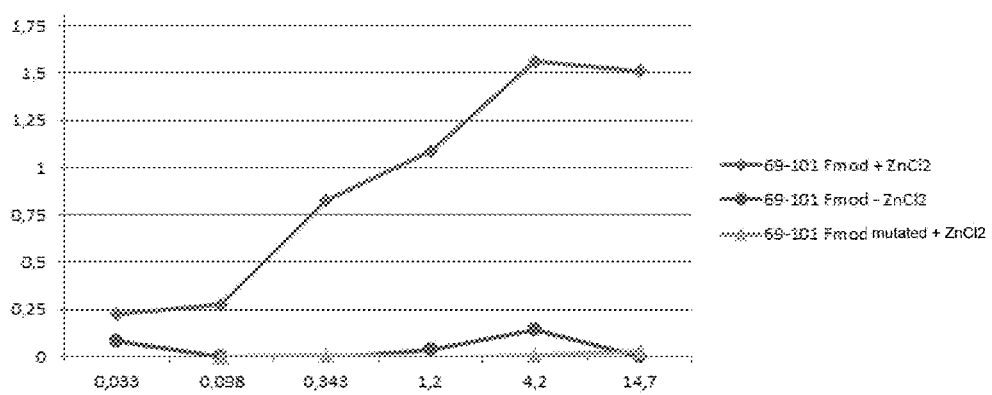
FIG. 3 shows the in vitro interaction between the peptides Fmod 69-101 (SEQ ID NO: 2) and Fmod 69-101 mutated (SEQ ID NO: 3) and myostatin, in the presence or absence of zinc.

2/In vitro Study of the Interaction Between the Myostatin and the Fibromodulin Peptides:

As shown in FIG. 3, the greater the amount of peptide Fmod 69-101 (SEQ ID NO: 2), the higher the absorbence. This indicates that a direct interaction takes place between the biotinylated mFmod 69-101 peptide and the myostatin. There is a plateau is obtained as from 4.2 μg of mFmod 69-101 peptide. In contrast, no interaction is seen between the peptide mFmod 69-101 and the myostatin in the absence of zinc. The mFmod 69-101 interaction with the myostatin is therefore zinc-dependent. Furthermore, no interaction is visible between the mutated biotin mFmod peptide (SEQ ID NO: 3) and the myostatin, even in the presence of zinc, which shows the importance of the three cysteines mutated to alanine.

3/In vivo Study: Body Mass and Weight of Muscles and Mice on D20 after Injection into the mdx Mice:

A first series of experiments was carried out on 5 mdx mice, injected by the IM path in the Tibialis Anterior (TA) with the following formulations:

TAG: 50 μg peptide mFmod 69-101 (SEQ ID NO: 2)+15 μM ZnCl2 in 25 μl of NaCl;

TAD: 15 μM ZnCl2+25 μl NaCl.

On D20, the mice were sacrificed and the weight of the TAG and TAD muscles was measured. The results are shown in the following table:

| Mouse   | Muscles | Weight (in mg) | Growth  |
|---------|---------|----------------|---------|
| Mouse 1 | TAD 1   | 71.6           | 5.31%   |
|         | TAG 1   | 75.4           |         |
| Mouse 2 | TAD 2   | 62.2           | 19.94%  |
|         | TAG 2   | 74.6           |         |
| Mouse 3 | TAD 3   | 61.9           | 5.33%   |
|         | TAG 3   | 65.2           |         |
| Mouse 4 | TAD 4   | 65.8           | 12.31%  |
|         | TAG 4   | 73.9           |         |
| Mouse 5 | TAG 5   | 54.4           | 22.24%  |
|         | TAG 5   | 66.5           |         |

These results show an effect on muscle growth.

4/In vivo Comparative Study of Muscle Hypertrophy 18 Days after Injection of Dystrophic mdx Mice with Decorin Peptide (MdCN 31-71, SEQ ID NO: 75), Fibromodulin (mFmod 69-101) or lumican (mLum 30-62):

The TAD and TAG muscles were removed 18 days after injection of the peptides, and then weighed. The experiment was performed on five separate mice. The average results obtained are shown in the following table:

| Treatment                | Hypertrophy %   |
|--------------------------|-----------------|
| mDCN 31-71 (SEQ ID NO: 75) | 10.02 ± 8.3   |
| mFmod 69-101 (SEQ ID NO: 2) | 29.34 ± 15.76 |
| mLum 30-62 (SEQ ID NO: 5) | 37.26 ± 14.69  |

The difference in muscle mass on day 18 between an mdx mouse having or not having received an intramuscular injection of decorin, fibromodulin or lumican indicates a significant effect for treatments based on peptide mFmod 69-101 and mLumican 30-62. There is a clear increase in muscular hypertrophy of a factor of 2.9 and 3.7 respectively compared to decorin.

---

The invention claimed is:

1. A method for increasing muscle mass, comprising:
administering to a subject in need thereof a composition comprising a peptide of less than 100 residues that
comprises a sequence containing the cysteine-rich consensus region $CX_3CXCX_9C$ and having at least 50% identity with SEQ ID NO: 1; and
is capable of binding myostatin in the presence of zinc;
so that the muscle mass of the subject is increased.

2. The method according to claim 1, wherein the increase in muscle mass is to compensate for wasting resulting from immobilization or old age.

3. The method according to claim 1, wherein the increase in muscle mass is to compensate for wasting resulting from a disease associated with muscle wasting.

4. The method according to claim 3, wherein the disease is a neuromuscular disease or cachexia.

5. The method of claim 4, wherein the neuromuscular disease is muscular dystrophy.

6. The method of claim 5, wherein the muscular dystrophy is Duchenne myopathy.

7. The method according to claim 1, wherein the subject is an animal.

8. The method according to claim 1, wherein the peptide comprises the sequence CAPECNCPHSYPTAMYC (SEQ ID NO: 4) or the sequence CAPECNCPESYPSAMYC (SEQ ID NO: 11).

9. The method according to claim 8, wherein the peptide comprises the sequence YGQISPNCAPECNCPH SYPTAMYCDDLKLKSVP (SEQ ID NO: 5) or the sequence YGQSSPNCAPECNCPE SYPSAMYCDELKLKSVP (SEQ ID NO: 12).

10. The method according to claim 1, wherein the peptide comprises the sequence CPQECDCPPNFPTAMYC (SEQ ID NO: 1).

11. The method according to claim 10, wherein the peptide comprises the sequence PPPEPRDCPQECDCPPNFPTAMYCDNRNLKYLP (SEQ ID NO: 2) or the sequence SPPDPRDCPQECDCPPNFPTAMYCDNRNLKYLP (SEQ ID NO: 10).

12. The method of claim 1, wherein the peptide has at least 50% identity with the sequence SEQ ID NO: 6 or the sequence SEQ ID NO: 7 over the full length of the peptide.

13. The method according to claim 1, wherein the composition further includes zinc.

14. The method according to claim 1, wherein the composition is administered by the intramuscular, intraperitoneal, subcutaneous, intravenous or oral path.

* * * * *

SEQUENCE LISTING

```
<160> NUMBER OF SEQ ID NOS: 79

<210> SEQ ID NO 1
<211> LENGTH: 17
<212> TYPE: PRT
<213> ORGANISM: artificial sequence
<220> FEATURE:
<223> OTHER INFORMATION: 76-92 mouse fibromodulin

<400> SEQUENCE: 1

Cys Pro Gln Glu Cys Asp Cys Pro Pro Asn Phe Pro Thr Ala Met Tyr
1               5                   10                  15

Cys

<210> SEQ ID NO 2
<211> LENGTH: 33
<212> TYPE: PRT
<213> ORGANISM: artificial sequence
<220> FEATURE:
<223> OTHER INFORMATION: 69-101 mouse fibromodulin Fmod
```

<400> SEQUENCE: 2

Pro Pro Pro Glu Pro Arg Asp Cys Pro Gln Glu Cys Asp Cys Pro Pro
1               5                   10                  15

Asn Phe Pro Thr Ala Met Tyr Cys Asp Asn Arg Asn Leu Lys Tyr Leu
            20                  25                  30

Pro

<210> SEQ ID NO 3
<211> LENGTH: 33
<212> TYPE: PRT
<213> ORGANISM: artificial sequence
<220> FEATURE:
<223> OTHER INFORMATION: 69-101 mutated mouse fibromodulin Fmod mutee

<400> SEQUENCE: 3

Pro Pro Pro Glu Pro Arg Asp Cys Pro Gln Glu Ala Asp Ala Pro Pro
1               5                   10                  15

Asn Phe Pro Thr Ala Met Tyr Ala Asp Asn Arg Asn Leu Lys Tyr Leu
            20                  25                  30

Pro

<210> SEQ ID NO 4
<211> LENGTH: 17
<212> TYPE: PRT
<213> ORGANISM: artificial sequence
<220> FEATURE:
<223> OTHER INFORMATION: 37-53 mouse lumican

<400> SEQUENCE: 4

Cys Ala Pro Glu Cys Asn Cys Pro His Ser Tyr Pro Thr Ala Met Tyr
1               5                   10                  15

Cys

<210> SEQ ID NO 5
<211> LENGTH: 33
<212> TYPE: PRT
<213> ORGANISM: artificial sequence
<220> FEATURE:
<223> OTHER INFORMATION: 30-62 mouse lumican

<400> SEQUENCE: 5

Tyr Gly Gln Ile Ser Pro Asn Cys Ala Pro Glu Cys Asn Cys Pro His
1               5                   10                  15

Ser Tyr Pro Thr Ala Met Tyr Cys Asp Asp Leu Lys Leu Lys Ser Val
            20                  25                  30

Pro

<210> SEQ ID NO 6
<211> LENGTH: 376
<212> TYPE: PRT
<213> ORGANISM: Mus musculus

<400> SEQUENCE: 6

Met Gln Trp Ala Ser Val Leu Leu Leu Ala Gly Leu Cys Ser Leu Ser
1               5                   10                  15

Gln Gly Gln Tyr Asp Glu Asp Ser His Trp Trp Ile Gln Tyr Leu Arg
            20                  25                  30

Asn Gln Gln Ser Thr Tyr Tyr Asp Pro Tyr Asp Pro Tyr Pro Tyr Glu
        35                  40                  45

```
Pro Ser Glu Pro Tyr Pro Tyr Gly Val Glu Glu Pro Ala Tyr Ala
    50                  55                  60

Tyr Gly Ala Pro Pro Pro Glu Pro Arg Asp Cys Pro Gln Glu Cys
 65             70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Ser Ala Ile Gln Glu Gly Val Phe Asp Asn Ala
                115                 120                 125

Thr Gly Leu Leu Trp Val Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu His
        195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Arg Val Pro Asp
225                 230                 235                 240

Gly Leu Pro Ser Ala Leu Glu Gln Leu Tyr Leu Glu His Asn Asn Val
                245                 250                 255

Tyr Thr Val Pro Asp Ser Tyr Phe Arg Gly Ser Pro Lys Leu Leu Tyr
            260                 265                 270

Val Arg Leu Ser His Asn Ser Leu Thr Asn Asn Gly Leu Ala Thr Asn
        275                 280                 285

Thr Phe Asn Ser Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Met Asn Phe Ser Lys Leu Gln Val Leu Arg Leu Asp Gly
            340                 345                 350

Asn Glu Ile Lys Arg Ser Ala Met Pro Val Asp Ala Pro Leu Cys Leu
        355                 360                 365

Arg Leu Ala Asn Leu Ile Glu Ile
    370                 375

<210> SEQ ID NO 7
<211> LENGTH: 376
<212> TYPE: PRT
<213> ORGANISM: Homo sapiens

<400> SEQUENCE: 7

Met Gln Trp Thr Ser Leu Leu Leu Ala Gly Leu Phe Ser Leu Ser
 1               5                  10                  15

Gln Ala Gln Tyr Glu Asp Asp Pro His Trp Trp Phe His Tyr Leu Arg
             20                  25                  30

Ser Gln Gln Ser Thr Tyr Tyr Asp Pro Tyr Asp Pro Tyr Pro Tyr Glu
         35                  40                  45
```

Thr Tyr Glu Pro Tyr Pro Tyr Gly Val Asp Glu Gly Pro Ala Tyr Thr
    50                  55                  60

Tyr Gly Ser Pro Ser Pro Asp Pro Arg Asp Cys Pro Gln Glu Cys
 65                  70                  75                  80

Asp Cys Pro Pro Asn Phe Pro Thr Ala Met Tyr Cys Asp Asn Arg Asn
                 85                  90                  95

Leu Lys Tyr Leu Pro Phe Val Pro Ser Arg Met Lys Tyr Val Tyr Phe
                100                 105                 110

Gln Asn Asn Gln Ile Thr Ser Ile Gln Glu Gly Val Phe Asp Asn Ala
                115                 120                 125

Thr Gly Leu Leu Trp Ile Ala Leu His Gly Asn Gln Ile Thr Ser Asp
                130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
                180                 185                 190

Asn Asn Ala Leu Glu Gly Leu Glu Asn Leu Thr Ala Leu Tyr Leu Gln
                195                 200                 205

His Asn Glu Ile Gln Glu Val Gly Ser Ser Met Arg Gly Leu Arg Ser
                210                 215                 220

Leu Tyr Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
                260                 265                 270

Val Arg Leu Ser His Asn Ser Leu Thr Asn Asn Gly Leu Ala Ser Asn
                275                 280                 285

Thr Phe Asn Ser Ser Ser Leu Leu Glu Leu Asp Leu Ser Tyr Asn Gln
                290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Gln Leu Gln Val Val Arg Leu Asp Gly
                340                 345                 350

Asn Glu Met Lys Arg Ser Ala Met Pro Ala Glu Ala Pro Leu Cys Leu
                355                 360                 365

Arg Leu Ala Ser Leu Ile Glu Ile
                370                 375

<210> SEQ ID NO 8
<211> LENGTH: 338
<212> TYPE: PRT
<213> ORGANISM: Mus musculus

<400> SEQUENCE: 8

Met Asn Val Cys Ala Phe Ser Leu Ala Leu Ala Leu Val Gly Ser Val
  1               5                  10                  15

Ser Gly Gln Tyr Tyr Asp Tyr Asp Ile Pro Leu Phe Met Tyr Gly Gln
                 20                  25                  30

Ile Ser Pro Asn Cys Ala Pro Glu Cys Asn Cys Pro His Ser Tyr Pro

```
            35                  40                  45
Thr Ala Met Tyr Cys Asp Asp Leu Lys Leu Lys Ser Val Pro Met Val
 50                  55                  60

Pro Pro Gly Ile Lys Tyr Leu Tyr Leu Arg Asn Asn Gln Ile Asp His
 65                  70                  75                  80

Ile Asp Glu Lys Ala Phe Glu Asn Val Thr Asp Leu Gln Trp Leu Ile
                 85                  90                  95

Leu Asp His Asn Leu Leu Glu Asn Ser Lys Ile Lys Glu Lys Val Phe
                100                 105                 110

Ser Lys Leu Lys Gln Leu Lys Lys Leu His Ile Asn Tyr Asn Asn Leu
                115                 120                 125

Thr Glu Ser Val Gly Pro Leu Pro Lys Ser Leu Gln Asp Leu Gln Leu
130                 135                 140

Thr Asn Asn Lys Ile Ser Lys Leu Gly Ser Phe Asp Gly Leu Val Asn
145                 150                 155                 160

Leu Thr Phe Ile Tyr Leu Gln His Asn Gln Leu Lys Glu Asp Ala Val
                165                 170                 175

Ser Ala Ser Leu Lys Gly Leu Lys Ser Leu Glu Tyr Leu Asp Leu Ser
                180                 185                 190

Phe Asn Gln Met Ser Lys Leu Pro Ala Gly Leu Pro Thr Ser Leu Leu
                195                 200                 205

Thr Leu Tyr Leu Asp Asn Asn Lys Ile Ser Asn Ile Pro Asp Glu Tyr
210                 215                 220

Phe Lys Arg Phe Thr Gly Leu Gln Tyr Leu Arg Leu Ser His Asn Glu
225                 230                 235                 240

Leu Ala Asp Ser Gly Val Pro Gly Asn Ser Phe Asn Ile Ser Ser Leu
                245                 250                 255

Leu Glu Leu Asp Leu Ser Tyr Asn Lys Leu Lys Ser Ile Pro Thr Val
                260                 265                 270

Asn Glu Asn Leu Glu Asn Tyr Tyr Leu Glu Val Asn Glu Leu Glu Lys
                275                 280                 285

Phe Asp Val Lys Thr Phe Cys Lys Ile Leu Gly Pro Leu Ser Tyr Ser
290                 295                 300

Lys Ile Lys His Leu Arg Leu Asp Gly Asn Pro Leu Thr Gln Ser Ser
305                 310                 315                 320

Leu Pro Pro Asp Met Tyr Glu Cys Leu Arg Val Ala Asn Glu Ile Thr
                325                 330                 335

Val Asn

<210> SEQ ID NO 9
<211> LENGTH: 338
<212> TYPE: PRT
<213> ORGANISM: Homo sapiens

<400> SEQUENCE: 9

Met Ser Leu Ser Ala Phe Thr Leu Phe Leu Ala Leu Ile Gly Gly Thr
 1               5                  10                  15

Ser Gly Gln Tyr Tyr Asp Tyr Asp Phe Pro Ser Ile Tyr Gly Gln
                 20                  25                  30

Ser Ser Pro Asn Cys Ala Pro Glu Cys Asn Cys Pro Glu Ser Tyr Pro
                 35                  40                  45

Ser Ala Met Tyr Cys Asp Glu Leu Lys Leu Lys Ser Val Pro Met Val
 50                  55                  60

Pro Pro Gly Ile Lys Tyr Leu Tyr Leu Arg Asn Asn Gln Ile Asp His
```

```
              65                  70                  75                  80
        Ile Asp Glu Lys Ala Phe Glu Asn Val Thr Asp Leu Gln Trp Leu Ile
                        85                  90                  95
        Leu Asp His Asn Val Leu Glu Asn Ser Lys Ile Lys Gly Arg Val Phe
                       100                 105                 110
        Ser Lys Leu Lys Gln Leu Lys Lys Leu His Ile Asn His Asn Asn Leu
                       115                 120                 125
        Thr Glu Ser Val Gly Pro Leu Pro Lys Ser Leu Glu Asp Leu Gln Leu
                       130                 135                 140
        Thr His Asn Lys Ile Thr Lys Leu Gly Ser Phe Glu Gly Leu Val Asn
                       145                 150                 155                 160
        Leu Thr Phe Ile His Leu Gln His Asn Arg Leu Lys Glu Asp Ala Val
                       165                 170                 175
        Ser Ala Ala Phe Lys Gly Leu Lys Ser Leu Glu Tyr Leu Asp Leu Ser
                       180                 185                 190
        Phe Asn Gln Ile Ala Arg Leu Pro Ser Gly Leu Pro Val Ser Leu Leu
                       195                 200                 205
        Thr Leu Tyr Leu Asp Asn Asn Lys Ile Ser Asn Ile Pro Asp Glu Tyr
                       210                 215                 220
        Phe Lys Arg Phe Asn Ala Leu Gln Tyr Leu Arg Leu Ser His Asn Glu
        225                 230                 235                 240
        Leu Ala Asp Ser Gly Ile Pro Gly Asn Ser Phe Asn Val Ser Ser Leu
                       245                 250                 255
        Val Glu Leu Asp Leu Ser Tyr Asn Lys Leu Lys Asn Ile Pro Thr Val
                       260                 265                 270
        Asn Glu Asn Leu Glu Asn Tyr Tyr Leu Glu Val Asn Gln Leu Glu Lys
                       275                 280                 285
        Phe Asp Ile Lys Ser Phe Cys Lys Ile Leu Gly Pro Leu Ser Tyr Ser
                       290                 295                 300
        Lys Ile Lys His Leu Arg Leu Asp Gly Asn Arg Ile Ser Glu Thr Ser
        305                 310                 315                 320
        Leu Pro Pro Asp Met Tyr Glu Cys Leu Arg Val Ala Asn Glu Val Thr
                       325                 330                 335
        Leu Asn

<210> SEQ ID NO 10
<211> LENGTH: 33
<212> TYPE: PRT
<213> ORGANISM: artificial
<220> FEATURE:
<223> OTHER INFORMATION: human fibromodulin peptide

<400> SEQUENCE: 10

Ser Pro Pro Asp Pro Arg Asp Cys Pro Gln Glu Cys Asp Cys Pro Pro
        1               5                   10                  15
        Asn Phe Pro Thr Ala Met Tyr Cys Asp Asn Arg Asn Leu Lys Tyr Leu
                       20                  25                  30
        Pro

<210> SEQ ID NO 11
<211> LENGTH: 17
<212> TYPE: PRT
<213> ORGANISM: artificial sequence
<220> FEATURE:
<223> OTHER INFORMATION: 37-53 human lumican

<400> SEQUENCE: 11
```

```
Cys Ala Pro Glu Cys Asn Cys Pro Glu Ser Tyr Pro Ser Ala Met Tyr
1               5                   10                  15

Cys

<210> SEQ ID NO 12
<211> LENGTH: 33
<212> TYPE: PRT
<213> ORGANISM: artificial sequence
<220> FEATURE:
<223> OTHER INFORMATION: 30-62 human lumican

<400> SEQUENCE: 12

Tyr Gly Gln Ser Ser Pro Asn Cys Ala Pro Glu Cys Asn Cys Pro Glu
1               5                   10                  15

Ser Tyr Pro Ser Ala Met Tyr Cys Asp Glu Leu Lys Leu Lys Ser Val
            20                  25                  30

Pro

<210> SEQ ID NO 13
<211> LENGTH: 373
<212> TYPE: PRT
<213> ORGANISM: Mus musculus

<400> SEQUENCE: 13

Met Lys Glu Tyr Val Met Leu Leu Leu Leu Ala Val Cys Ser Ala Lys
1               5                   10                  15

Pro Phe Phe Ser Pro Ser His Thr Ala Leu Lys Asn Met Met Leu Lys
            20                  25                  30

Asp Met Glu Asp Thr Asp Asp Asp Asn Asp Asp Asp Asn Ser
        35                  40                  45

Leu Phe Pro Thr Lys Glu Pro Val Asn Pro Phe Phe Pro Phe Asp Leu
    50                  55                  60

Phe Pro Thr Cys Pro Phe Gly Cys Gln Cys Tyr Ser Arg Val Val His
65                  70                  75                  80

Cys Ser Asp Leu Gly Leu Thr Ser Val Pro Asn Asn Ile Pro Phe Asp
                85                  90                  95

Thr Arg Met Val Asp Leu Gln Asn Asn Lys Ile Lys Glu Ile Lys Glu
            100                 105                 110

Asn Asp Phe Lys Gly Leu Thr Ser Leu Tyr Ala Leu Ile Leu Asn Asn
        115                 120                 125

Asn Lys Leu Thr Lys Ile His Pro Lys Thr Phe Leu Thr Thr Lys Lys
    130                 135                 140

Leu Arg Arg Leu Tyr Leu Ser His Asn Gln Leu Ser Glu Ile Pro Leu
145                 150                 155                 160

Asn Leu Pro Lys Ser Leu Ala Glu Leu Arg Ile His Asp Asn Lys Val
                165                 170                 175

Lys Lys Ile Gln Lys Asp Thr Phe Lys Gly Met Asn Ala Leu His Val
            180                 185                 190

Leu Glu Met Ser Ala Asn Pro Leu Glu Asn Asn Gly Ile Glu Pro Gly
        195                 200                 205

Ala Phe Glu Gly Val Thr Val Phe His Ile Arg Ile Ala Glu Ala Lys
    210                 215                 220

Leu Thr Ser Ile Pro Lys Gly Leu Pro Pro Thr Leu Leu Glu Leu His
225                 230                 235                 240

Leu Asp Phe Asn Lys Ile Ser Thr Val Glu Leu Glu Asp Leu Lys Arg
                245                 250                 255
```

Tyr Arg Glu Leu Gln Arg Leu Gly Leu Gly Asn Asn Arg Ile Thr Asp
                260                 265                 270

Ile Glu Asn Gly Thr Phe Ala Asn Ile Pro Arg Val Arg Glu Ile His
            275                 280                 285

Leu Glu His Asn Lys Leu Lys Lys Ile Pro Ser Gly Leu Gln Glu Leu
        290                 295                 300

Lys Tyr Leu Gln Ile Ile Phe Leu His Tyr Asn Ser Ile Ala Lys Val
305                 310                 315                 320

Gly Val Asn Asp Phe Cys Pro Thr Val Pro Lys Met Lys Lys Ser Leu
                325                 330                 335

Tyr Ser Ala Ile Ser Leu Phe Asn Asn Pro Met Lys Tyr Trp Glu Ile
            340                 345                 350

Gln Pro Ala Thr Phe Arg Cys Val Leu Gly Arg Met Ser Val Gln Leu
        355                 360                 365

Gly Asn Val Gly Lys
    370

<210> SEQ ID NO 14
<211> LENGTH: 380
<212> TYPE: PRT
<213> ORGANISM: Homo sapiens

<400> SEQUENCE: 14

Met Lys Glu Tyr Val Leu Leu Leu Phe Leu Ala Leu Cys Ser Ala Lys
1               5                   10                  15

Pro Phe Phe Ser Pro Ser His Ile Ala Leu Lys Asn Met Met Leu Lys
            20                  25                  30

Asp Met Glu Asp Thr Asp Asp Asp Asp Asp Asp Asp Asp Asp Asp Asp
        35                  40                  45

Asp Asp Asp Glu Asp Asn Ser Leu Phe Pro Thr Arg Glu Pro Arg Ser
    50                  55                  60

His Phe Phe Pro Phe Asp Leu Phe Pro Met Cys Pro Phe Gly Cys Gln
65                  70                  75                  80

Cys Tyr Ser Arg Val Val His Cys Ser Asp Leu Gly Leu Thr Ser Val
                85                  90                  95

Pro Thr Asn Ile Pro Phe Asp Thr Arg Met Leu Asp Leu Gln Asn Asn
            100                 105                 110

Lys Ile Lys Glu Ile Lys Glu Asn Asp Phe Lys Gly Leu Thr Ser Leu
        115                 120                 125

Tyr Gly Leu Ile Leu Asn Asn Asn Lys Leu Thr Lys Ile His Pro Lys
    130                 135                 140

Ala Phe Leu Thr Thr Lys Lys Leu Arg Arg Leu Tyr Leu Ser His Asn
145                 150                 155                 160

Gln Leu Ser Glu Ile Pro Leu Asn Leu Pro Lys Ser Leu Ala Glu Leu
                165                 170                 175

Arg Ile His Glu Asn Lys Val Lys Lys Ile Gln Lys Asp Thr Phe Lys
            180                 185                 190

Gly Met Asn Ala Leu His Val Leu Glu Met Ser Ala Asn Pro Leu Asp
        195                 200                 205

Asn Asn Gly Ile Glu Pro Gly Ala Phe Glu Gly Val Thr Val Phe His
    210                 215                 220

Ile Arg Ile Ala Glu Ala Lys Leu Thr Ser Val Pro Lys Gly Leu Pro
225                 230                 235                 240

Pro Thr Leu Leu Glu Leu His Leu Asp Tyr Asn Lys Ile Ser Thr Val

```
                245                 250                 255
Glu Leu Glu Asp Phe Lys Arg Tyr Lys Glu Leu Gln Arg Leu Gly Leu
            260                 265                 270

Gly Asn Asn Lys Ile Thr Asp Ile Glu Asn Gly Ser Leu Ala Asn Ile
        275                 280                 285

Pro Arg Val Arg Glu Ile His Leu Glu Asn Asn Lys Leu Lys Lys Ile
    290                 295                 300

Pro Ser Gly Leu Pro Glu Leu Lys Tyr Leu Gln Ile Ile Phe Leu His
305                 310                 315                 320

Ser Asn Ser Ile Ala Arg Val Gly Val Asn Asp Phe Cys Pro Thr Val
                325                 330                 335

Pro Lys Met Lys Lys Ser Leu Tyr Ser Ala Ile Ser Leu Phe Asn Asn
            340                 345                 350

Pro Val Lys Tyr Trp Glu Met Gln Pro Ala Thr Phe Arg Cys Val Leu
        355                 360                 365

Ser Arg Met Ser Val Gln Leu Gly Asn Phe Gly Met
    370                 375                 380

<210> SEQ ID NO 15
<211> LENGTH: 14
<212> TYPE: PRT
<213> ORGANISM: artificial sequence
<220> FEATURE:
<223> OTHER INFORMATION: asporin fragment

<400> SEQUENCE: 15

Cys Pro Phe Gly Cys Gln Cys Tyr Ser Arg Val Val His Cys
1               5                   10

<210> SEQ ID NO 16
<211> LENGTH: 36
<212> TYPE: PRT
<213> ORGANISM: artificial sequence
<220> FEATURE:
<223> OTHER INFORMATION: 55-90 mouse asporin

<400> SEQUENCE: 16

Pro Val Asn Pro Phe Phe Pro Phe Asp Leu Phe Pro Thr Cys Pro Phe
1               5                   10                  15

Gly Cys Gln Cys Tyr Ser Arg Val Val His Cys Ser Asp Leu Gly Leu
            20                  25                  30

Thr Ser Val Pro
        35

<210> SEQ ID NO 17
<211> LENGTH: 36
<212> TYPE: PRT
<213> ORGANISM: artificial sequence
<220> FEATURE:
<223> OTHER INFORMATION: 62-97 human asporin

<400> SEQUENCE: 17

Pro Arg Ser His Phe Phe Pro Phe Asp Leu Phe Pro Met Cys Pro Phe
1               5                   10                  15

Gly Cys Gln Cys Tyr Ser Arg Val Val His Cys Ser Asp Leu Gly Leu
            20                  25                  30

Thr Ser Val Pro
        35

<210> SEQ ID NO 18
```

<211> LENGTH: 423
<212> TYPE: PRT
<213> ORGANISM: Mus musculus

<400> SEQUENCE: 18

```
Met Gly Phe Leu Ser Pro Ile Tyr Val Leu Phe Phe Cys Phe Gly Val
1               5                   10                  15

Arg Val Tyr Cys Gln Tyr Glu Ala Tyr Arg Trp Asp Asp Tyr Asp
            20                  25                  30

Gln Glu Pro Asn Glu Asp Tyr Asp Pro Glu Phe Gln Phe His Gln Asn
            35                  40                  45

Ile Glu Tyr Gly Val Pro Phe Tyr Asn Asn Ile Leu Gly Cys Ala Lys
50                  55                  60

Glu Cys Phe Cys Pro Thr Asn Phe Pro Thr Ser Met Tyr Cys Asp Asn
65                  70                  75                  80

Arg Lys Leu Lys Thr Ile Pro Ile Ile Pro Met His Ile Gln Gln Leu
                85                  90                  95

Asn Leu Gln Phe Asn Asp Ile Glu Ala Val Thr Ala Asn Ser Phe Ile
            100                 105                 110

Asn Ala Thr His Leu Lys Glu Ile Asn Leu Ser His Asn Lys Ile Lys
        115                 120                 125

Ser Gln Lys Ile Asp Tyr Gly Val Phe Ala Lys Leu Ser Asn Leu Gln
    130                 135                 140

Gln Leu His Leu Glu His Asn Asn Leu Glu Glu Phe Pro Phe Pro Leu
145                 150                 155                 160

Pro Lys Ser Leu Glu Arg Leu Leu Leu Gly Tyr Asn Glu Ile Ser Ile
                165                 170                 175

Leu Pro Thr Asn Ala Met Asp Gly Leu Val Asn Val Thr Met Leu Asp
            180                 185                 190

Leu Cys Tyr Asn His Leu Ser Asp Ser Met Leu Lys Glu Lys Thr Leu
        195                 200                 205

Ser Lys Met Glu Lys Leu Met Gln Leu Asn Leu Cys Asn Asn Arg Leu
    210                 215                 220

Glu Ser Met Pro Leu Gly Leu Pro Ser Ser Leu Met Tyr Leu Ser Leu
225                 230                 235                 240

Glu Asn Asn Ser Ile Ser Ser Ile Pro Asp Asn Tyr Phe Asp Lys Leu
                245                 250                 255

Pro Lys Leu His Ala Leu Arg Ile Ser His Asn Lys Leu Glu Asp Ile
            260                 265                 270

Pro Tyr Asp Ile Phe Asn Leu Ser Asn Leu Ile Glu Leu Asn Val Gly
        275                 280                 285

His Asn Lys Leu Lys Gln Ala Phe Tyr Ile Pro Arg Asn Leu Glu His
    290                 295                 300

Leu Tyr Leu Gln Asn Asn Glu Ile Glu Ser Ile Asn Val Thr Met Ile
305                 310                 315                 320

Cys Pro Ser Pro Asp Pro Val His His His Leu Thr Tyr Leu Arg
                325                 330                 335

Val Asp Gln Asn Lys Leu Lys Glu Pro Ile Ser Ser Tyr Ile Phe Phe
            340                 345                 350

Cys Phe Pro Arg Ile His Ser Ile Tyr Tyr Gly Glu Gln Arg Ser Thr
        355                 360                 365

Asn Gly Glu Thr Ile Gln Leu Lys Thr Gln Val Phe Arg Ser Tyr Gln
    370                 375                 380

Glu Glu Glu Glu Glu Asp Asp His Asp Ser Gln Asp Asn Thr Leu Glu
```

```
            385                 390                 395                 400
Gly Gln Glu Val Ser Asp Glu His Tyr Asn Ser His Tyr Tyr Glu Met
                    405                 410                 415
Gln Glu Trp Gln Asp Thr Ile
                420
```

<210> SEQ ID NO 19
<211> LENGTH: 421
<212> TYPE: PRT
<213> ORGANISM: Homo sapiens

<400> SEQUENCE: 19

```
Met Gly Phe Leu Ser Pro Ile Tyr Val Ile Phe Phe Phe Phe Gly Val
1               5                   10                  15

Lys Val His Cys Gln Tyr Glu Thr Tyr Gln Trp Asp Glu Asp Tyr Asp
                20                  25                  30

Gln Glu Pro Asp Asp Asp Tyr Gln Thr Gly Phe Pro Phe Arg Gln Asn
            35                  40                  45

Val Asp Tyr Gly Val Pro Phe His Gln Tyr Thr Leu Gly Cys Val Ser
    50                  55                  60

Glu Cys Phe Cys Pro Thr Asn Phe Pro Ser Ser Met Tyr Cys Asp Asn
65                  70                  75                  80

Arg Lys Leu Lys Thr Ile Pro Asn Ile Pro Met His Ile Gln Gln Leu
                85                  90                  95

Tyr Leu Gln Phe Asn Glu Ile Glu Ala Val Thr Ala Asn Ser Phe Ile
            100                 105                 110

Asn Ala Thr His Leu Lys Glu Ile Asn Leu Ser His Asn Lys Ile Lys
        115                 120                 125

Ser Gln Lys Ile Asp Tyr Gly Val Phe Ala Lys Leu Pro Asn Leu Leu
    130                 135                 140

Gln Leu His Leu Glu His Asn Asn Leu Glu Glu Phe Pro Phe Pro Leu
145                 150                 155                 160

Pro Lys Ser Leu Glu Arg Leu Leu Leu Gly Tyr Asn Glu Ile Ser Lys
                165                 170                 175

Leu Gln Thr Asn Ala Met Asp Gly Leu Val Asn Leu Thr Met Leu Asp
            180                 185                 190

Leu Cys Tyr Asn Tyr Leu His Asp Ser Leu Leu Lys Asp Lys Ile Phe
        195                 200                 205

Ala Lys Met Glu Lys Leu Met Gln Leu Asn Leu Cys Ser Asn Arg Leu
    210                 215                 220

Glu Ser Met Pro Pro Gly Leu Pro Ser Ser Leu Met Tyr Leu Ser Leu
225                 230                 235                 240

Glu Asn Asn Ser Ile Ser Ser Ile Pro Glu Lys Tyr Phe Asp Lys Leu
                245                 250                 255

Pro Lys Leu His Thr Leu Arg Met Ser His Asn Lys Leu Gln Asp Ile
            260                 265                 270

Pro Tyr Asn Ile Phe Asn Leu Pro Asn Ile Val Glu Leu Ser Val Gly
        275                 280                 285

His Asn Lys Leu Lys Gln Ala Phe Tyr Ile Pro Arg Asn Leu Glu His
    290                 295                 300

Leu Tyr Leu Gln Asn Asn Glu Ile Glu Lys Met Asn Leu Thr Val Met
305                 310                 315                 320

Cys Pro Ser Ile Asp Pro Leu His Tyr His Leu Thr Tyr Ile Arg
                325                 330                 335
```

```
Val Asp Gln Asn Lys Leu Lys Glu Pro Ile Ser Ser Tyr Ile Phe Phe
            340                 345                 350

Cys Phe Pro His Ile His Thr Ile Tyr Tyr Gly Glu Gln Arg Ser Thr
        355                 360                 365

Asn Gly Gln Thr Ile Gln Leu Lys Thr Gln Val Phe Arg Arg Phe Pro
    370                 375                 380

Asp Asp Asp Asp Glu Ser Glu Asp His Asp Asp Pro Asp Asn Ala His
385                 390                 395                 400

Glu Ser Pro Glu Gln Glu Gly Ala Glu Gly His Phe Asp Leu His Tyr
                405                 410                 415

Tyr Glu Asn Gln Glu
            420

<210> SEQ ID NO 20
<211> LENGTH: 17
<212> TYPE: PRT
<213> ORGANISM: artificial sequence
<220> FEATURE:
<223> OTHER INFORMATION: mouse osteoadherin fragment

<400> SEQUENCE: 20

Cys Ala Lys Glu Cys Phe Cys Pro Thr Asn Pro Thr Ser Met Tyr
1               5                   10                  15

Cys

<210> SEQ ID NO 21
<211> LENGTH: 17
<212> TYPE: PRT
<213> ORGANISM: artificial sequence
<220> FEATURE:
<223> OTHER INFORMATION: human osteoadherin fragment

<400> SEQUENCE: 21

Cys Val Ser Glu Cys Phe Cys Pro Thr Asn Phe Pro Ser Ser Met Tyr
1               5                   10                  15

Cys

<210> SEQ ID NO 22
<211> LENGTH: 37
<212> TYPE: PRT
<213> ORGANISM: artificial sequence
<220> FEATURE:
<223> OTHER INFORMATION: 51-87 mouse osteoadherin

<400> SEQUENCE: 22

Tyr Gly Val Pro Phe Tyr Asn Asn Ile Leu Gly Cys Ala Lys Glu Cys
1               5                   10                  15

Phe Cys Pro Thr Asn Phe Pro Thr Ser Met Tyr Cys Asp Asn Arg Lys
            20                  25                  30

Leu Lys Thr Ile Pro
        35

<210> SEQ ID NO 23
<211> LENGTH: 37
<212> TYPE: PRT
<213> ORGANISM: artificial sequence
<220> FEATURE:
<223> OTHER INFORMATION: 51-87 human osteoadherin

<400> SEQUENCE: 23

Tyr Gly Val Pro Phe His Gln Tyr Thr Leu Gly Cys Val Ser Glu Cys
1               5                   10                  15
```

-continued

```
Phe Cys Pro Thr Asn Phe Pro Ser Ser Met Tyr Cys Asp Asn Arg Lys
            20                  25                  30

Leu Lys Thr Ile Pro
        35

<210> SEQ ID NO 24
<211> LENGTH: 378
<212> TYPE: PRT
<213> ORGANISM: Mus musculus

<400> SEQUENCE: 24

Met Arg Ala Ser Phe Phe Trp Leu Leu Pro Leu Leu Ile Leu Ala
1               5                  10                  15

Ser Val Ala Gln Gly Gln Pro Thr Arg Pro Lys Pro Gly Ile Arg Arg
            20                  25                  30

Lys Pro Lys Pro Arg Pro Thr Pro Arg Phe Pro Gln Ala Pro Glu Pro
        35                  40                  45

Ala Glu Pro Thr Asp Leu Pro Pro Leu Pro Gly Pro Pro Ser
50                  55                  60

Val Phe Pro Asp Cys Pro Arg Glu Cys Tyr Cys Pro Pro Asp Phe Pro
65                  70                  75                  80

Ser Ala Leu Tyr Cys Asp Ser Arg Asn Leu Arg Arg Val Pro Val Ile
                85                  90                  95

Pro Pro Arg Ile His Tyr Leu Tyr Leu Gln Asn Asn Phe Ile Thr Glu
            100                 105                 110

Leu Pro Leu Glu Ser Phe Gln Asn Ala Thr Gly Leu Arg Trp Val Asn
        115                 120                 125

Leu Asp Asn Asn Arg Ile Arg Lys Val Asp Gln Arg Val Leu Gly Lys
    130                 135                 140

Leu Pro Ser Leu Ala Phe Leu Tyr Met Glu Lys Asn Gln Leu Glu Glu
145                 150                 155                 160

Val Pro Ser Ala Leu Pro Arg Asn Leu Glu Gln Leu Arg Leu Ser Gln
                165                 170                 175

Asn Leu Ile Ser Arg Ile Pro Pro Gly Val Phe Ser Lys Leu Glu Asn
            180                 185                 190

Leu Leu Leu Leu Asp Leu Gln His Asn Arg Leu Ser Asp Gly Val Phe
        195                 200                 205

Lys Ala Asp Thr Phe Gln Gly Leu Lys Asn Leu Met Gln Leu Asn Leu
    210                 215                 220

Ala His Asn Ile Leu Arg Lys Met Pro Pro Lys Val Pro Gln Ala Ile
225                 230                 235                 240

His Gln Leu Tyr Leu Asp Ser Asn Lys Ile Glu Thr Ile Pro Asn Gly
                245                 250                 255

Tyr Phe Lys Asp Phe Pro Asn Leu Ala Phe Ile Arg Met Asn Tyr Asn
            260                 265                 270

Lys Leu Ser Asp Arg Gly Leu Pro Lys Asn Ser Phe Asn Ile Ser Asn
        275                 280                 285

Leu Leu Val Leu His Leu Ser His Asn Lys Ile Ser Asn Val Pro Ala
    290                 295                 300

Ile Ser Asn Lys Leu Glu His Leu Tyr Leu Asn Asn Ser Ile Glu
305                 310                 315                 320

Lys Ile Asn Gly Thr Gln Ile Cys Pro Asn Asn Leu Val Ala Phe His
                325                 330                 335

Asp Phe Ser Ser Asp Leu Glu Asn Val Pro His Leu Arg Tyr Leu Arg
```

```
            340             345             350
Leu Asp Gly Asn Phe Leu Lys Pro Pro Ile Pro Leu Asp Leu Met Met
        355                 360                 365

Cys Phe Arg Leu Leu Gln Ser Val Val Ile
370                 375

<210> SEQ ID NO 25
<211> LENGTH: 382
<212> TYPE: PRT
<213> ORGANISM: Homo sapiens

<400> SEQUENCE: 25

Met Arg Ser Pro Leu Cys Trp Leu Leu Pro Leu Leu Ile Leu Ala Ser
1               5                   10                  15

Val Ala Gln Gly Gln Pro Thr Arg Arg Pro Arg Pro Gly Thr Gly Pro
            20                  25                  30

Gly Arg Arg Pro Arg Pro Arg Pro Thr Pro Ser Phe Pro Gln
        35                  40                  45

Pro Asp Glu Pro Ala Glu Pro Thr Asp Leu Pro Pro Pro Leu Pro Pro
    50                  55                  60

Gly Pro Pro Ser Ile Phe Pro Asp Cys Pro Arg Glu Cys Tyr Cys Pro
65                  70                  75                  80

Pro Asp Phe Pro Ser Ala Leu Tyr Cys Asp Ser Arg Asn Leu Arg Lys
                85                  90                  95

Val Pro Val Ile Pro Arg Ile His Tyr Leu Tyr Leu Gln Asn Asn
            100                 105                 110

Phe Ile Thr Glu Leu Pro Val Glu Ser Phe Gln Asn Ala Thr Gly Leu
            115                 120                 125

Arg Trp Ile Asn Leu Asp Asn Asn Arg Ile Arg Lys Ile Asp Gln Arg
130                 135                 140

Val Leu Glu Lys Leu Pro Gly Leu Val Phe Leu Tyr Met Glu Lys Asn
145                 150                 155                 160

Gln Leu Glu Glu Val Pro Ser Ala Leu Pro Arg Asn Leu Glu Gln Leu
                165                 170                 175

Arg Leu Ser Gln Asn His Ile Ser Arg Ile Pro Pro Gly Val Phe Ser
            180                 185                 190

Lys Leu Glu Asn Leu Leu Leu Leu Asp Leu Gln His Asn Arg Leu Ser
        195                 200                 205

Asp Gly Val Phe Lys Pro Asp Thr Phe His Gly Leu Lys Asn Leu Met
210                 215                 220

Gln Leu Asn Leu Ala His Asn Ile Leu Arg Lys Met Pro Pro Arg Val
225                 230                 235                 240

Pro Thr Ala Ile His Gln Leu Tyr Leu Asp Ser Asn Lys Ile Glu Thr
                245                 250                 255

Ile Pro Asn Gly Tyr Phe Lys Ser Phe Pro Asn Leu Ala Phe Ile Arg
            260                 265                 270

Leu Asn Tyr Asn Lys Leu Thr Asp Arg Gly Leu Pro Lys Asn Ser Phe
        275                 280                 285

Asn Ile Ser Asn Leu Leu Val Leu His Leu Ser His Asn Arg Ile Ser
290                 295                 300

Ser Val Pro Ala Ile Asn Asn Arg Leu Glu His Leu Tyr Leu Asn Asn
305                 310                 315                 320

Asn Ser Ile Glu Lys Ile Asn Gly Thr Gln Ile Cys Pro Asn Asp Leu
                325                 330                 335
```

```
Val Ala Phe His Asp Phe Ser Ser Leu Glu Asn Val Pro His Leu
            340                 345                 350

Arg Tyr Leu Arg Leu Asp Gly Asn Tyr Leu Lys Pro Pro Ile Pro Leu
        355                 360                 365

Asp Leu Met Met Cys Phe Arg Leu Leu Gln Ser Val Val Ile
    370                 375                 380

<210> SEQ ID NO 26
<211> LENGTH: 13
<212> TYPE: PRT
<213> ORGANISM: artificial sequence
<220> FEATURE:
<223> OTHER INFORMATION: PRELP fragment

<400> SEQUENCE: 26

Cys Tyr Cys Pro Pro Asp Phe Pro Ser Ala Leu Tyr Cys
1               5                   10

<210> SEQ ID NO 27
<211> LENGTH: 33
<212> TYPE: PRT
<213> ORGANISM: artificial sequence
<220> FEATURE:
<223> OTHER INFORMATION: 62-94 mouse PRELP

<400> SEQUENCE: 27

Pro Pro Ser Val Phe Pro Asp Cys Pro Arg Glu Cys Tyr Cys Pro Pro
1               5                   10                  15

Asp Phe Pro Ser Ala Leu Tyr Cys Asp Ser Arg Asn Leu Arg Arg Val
            20                  25                  30

Pro

<210> SEQ ID NO 28
<211> LENGTH: 33
<212> TYPE: PRT
<213> ORGANISM: artificial sequence
<220> FEATURE:
<223> OTHER INFORMATION: 66-98 human PRELP

<400> SEQUENCE: 28

Pro Pro Ser Ile Phe Pro Asp Cys Pro Arg Glu Cys Tyr Cys Pro Pro
1               5                   10                  15

Asp Phe Pro Ser Ala Leu Tyr Cys Asp Ser Arg Asn Leu Arg Lys Val
            20                  25                  30

Pro

<210> SEQ ID NO 29
<211> LENGTH: 322
<212> TYPE: PRT
<213> ORGANISM: Mus musculus

<400> SEQUENCE: 29

Met Gly Met Leu Ala Arg Val Ala Leu Gly Leu Ile Ile Ile Asp Ala
1               5                   10                  15

Val Leu Ala Ala Pro Thr Thr Glu Leu Phe Asn Tyr Asp Ser Glu Val
            20                  25                  30

Tyr Asp Ala Ile Leu Glu Asp Thr Gly Thr Phe Tyr Asn Tyr Glu His
        35                  40                  45

Ile Pro Asp Asn His Val Glu Asn Glu Lys Val Ser Glu Arg Leu Ser
    50                  55                  60

Gly Asn Arg Glu Leu Leu Thr Pro Gly Pro Gln Leu Gly Asp Asn Gln
```

```
                65                  70                  75                  80
Asp Glu Asp Lys Asp Glu Glu Ser Thr Pro Arg Leu Ile Asp Gly Ser
                    85                  90                  95

Ser Pro Gln Glu Pro Glu Phe Pro Gly Leu Leu Gly Pro His Thr Asn
                100                 105                 110

Glu Asp Phe Pro Thr Cys Leu Leu Cys Thr Cys Ile Ser Thr Thr Val
                115                 120                 125

Tyr Cys Asp Asp His Glu Leu Asp Ala Ile Pro Pro Leu Pro Lys Lys
            130                 135                 140

Thr Thr Tyr Phe Tyr Ser Arg Phe Asn Arg Ile Lys Lys Ile Asn Lys
145                 150                 155                 160

Asn Asp Phe Ala Ser Leu Asn Asp Leu Lys Arg Ile Asp Leu Thr Ser
                    165                 170                 175

Asn Leu Ile Ser Glu Ile Asp Glu Asp Ala Phe Arg Lys Leu Pro His
                180                 185                 190

Leu Gln Glu Leu Val Leu Arg Asp Asn Lys Ile Lys Gln Leu Pro Glu
                195                 200                 205

Leu Pro Asn Thr Leu Thr Phe Ile Asp Ile Ser Asn Asn Arg Leu Gly
            210                 215                 220

Arg Lys Gly Ile Lys Gln Glu Ala Phe Lys Asp Met Tyr Asp Leu His
225                 230                 235                 240

His Leu Tyr Ile Thr Asp Asn Ser Leu Asp His Ile Pro Leu Pro Leu
                    245                 250                 255

Pro Glu Ser Leu Arg Ala Leu His Leu Gln Asn Asn Asp Ile Leu Glu
                260                 265                 270

Met His Glu Asp Thr Phe Cys Asn Val Lys Asn Leu Thr Tyr Val Arg
                275                 280                 285

Lys Ala Leu Glu Asp Ile Arg Leu Asp Gly Asn Pro Ile Asn Leu Ser
            290                 295                 300

Arg Thr Pro Gln Ala Tyr Met Cys Leu Pro Arg Leu Pro Ile Gly Ser
305                 310                 315                 320

Phe Ile

<210> SEQ ID NO 30
<211> LENGTH: 322
<212> TYPE: PRT
<213> ORGANISM: Homo sapiens

<400> SEQUENCE: 30

Met Lys Thr Leu Ala Gly Leu Val Leu Gly Leu Val Ile Phe Asp Ala
1               5                   10                  15

Ala Val Thr Ala Pro Thr Leu Glu Ser Ile Asn Tyr Asp Ser Glu Thr
                20                  25                  30

Tyr Asp Ala Thr Leu Glu Asp Leu Asp Asn Leu Tyr Asn Tyr Glu Asn
            35                  40                  45

Ile Pro Val Gly Lys Val Glu Ile Glu Ile Ala Thr Val Met Pro Ser
        50                  55                  60

Gly Asn Arg Glu Leu Leu Thr Pro Pro Gln Pro Glu Lys Ala Gln
65                  70                  75                  80

Glu Glu Glu Glu Glu Glu Ser Thr Pro Arg Leu Ile Asp Gly Ser
                    85                  90                  95

Ser Pro Gln Glu Pro Glu Phe Thr Gly Val Leu Gly Pro His Thr Asn
                100                 105                 110

Glu Asp Phe Pro Thr Cys Leu Leu Cys Thr Cys Ile Ser Thr Thr Val
```

```
                    115                 120                 125
Tyr Cys Asp Asp His Glu Leu Asp Ala Ile Pro Pro Leu Pro Lys Asn
            130                 135                 140

Thr Ala Tyr Phe Tyr Ser Arg Phe Asn Arg Ile Lys Lys Ile Asn Lys
145                 150                 155                 160

Asn Asp Phe Ala Ser Leu Ser Asp Leu Lys Arg Ile Asp Leu Thr Ser
                165                 170                 175

Asn Leu Ile Ser Glu Ile Asp Glu Asp Ala Phe Arg Lys Leu Pro Gln
            180                 185                 190

Leu Arg Glu Leu Val Leu Arg Asp Asn Lys Ile Arg Gln Leu Pro Glu
        195                 200                 205

Leu Pro Thr Thr Leu Thr Phe Ile Asp Ile Ser Asn Asn Arg Leu Gly
        210                 215                 220

Arg Lys Gly Ile Lys Gln Glu Ala Phe Lys Asp Met Tyr Asp Leu His
225                 230                 235                 240

His Leu Tyr Leu Thr Asp Asn Asn Leu Asp His Ile Pro Leu Pro Leu
                245                 250                 255

Pro Glu Asn Leu Arg Ala Leu His Leu Gln Asn Asn Asn Ile Leu Glu
            260                 265                 270

Met His Glu Asp Thr Phe Cys Asn Val Lys Asn Leu Thr Tyr Ile Arg
        275                 280                 285

Lys Ala Leu Glu Asp Ile Arg Leu Asp Gly Asn Pro Ile Asn Leu Ser
        290                 295                 300

Lys Thr Pro Gln Ala Tyr Met Cys Leu Pro Arg Leu Pro Val Gly Ser
305                 310                 315                 320

Leu Val

<210> SEQ ID NO 31
<211> LENGTH: 13
<212> TYPE: PRT
<213> ORGANISM: artificial sequence
<220> FEATURE:
<223> OTHER INFORMATION: epiphycan fragment

<400> SEQUENCE: 31

Cys Leu Leu Cys Thr Cys Ile Ser Thr Thr Val Tyr Cys
1               5                   10

<210> SEQ ID NO 32
<211> LENGTH: 29
<212> TYPE: PRT
<213> ORGANISM: artificial sequence
<220> FEATURE:
<223> OTHER INFORMATION: 111-139 epiphycan

<400> SEQUENCE: 32

Thr Asn Glu Asp Phe Pro Thr Cys Leu Leu Cys Thr Cys Ile Ser Thr
1               5                   10                  15

Thr Val Tyr Cys Asp Asp His Glu Leu Asp Ala Ile Pro
            20                  25

<210> SEQ ID NO 33
<211> LENGTH: 298
<212> TYPE: PRT
<213> ORGANISM: Mus musculus

<400> SEQUENCE: 33

Met Glu Thr Val His Ser Thr Phe Leu Leu Leu Leu Phe Val Pro Leu
1               5                   10                  15
```

-continued

Thr Gln Gln Ala Pro Gln Ser Gln Leu Asp Ser His Val Asn Tyr Glu
         20                  25                  30

Tyr Ala Thr Gly Asn Ser Glu Glu Thr Lys Phe Ser Gln Asp Tyr Glu
             35                  40                  45

Asp Lys Tyr Leu Asp Gly Lys Ser Ile Lys Glu Lys Glu Thr Met Ile
 50                  55                  60

Ile Pro Asp Glu Lys Ser Leu Gln Leu Gln Lys Asp Glu Val Ile Pro
 65                  70                  75                  80

Ser Leu Pro Thr Lys Lys Glu Asn Asp Glu Met Pro Thr Cys Leu Leu
             85                  90                  95

Cys Val Cys Leu Ser Gly Ser Val Tyr Cys Glu Glu Val Asp Ile Asp
            100                 105                 110

Ala Val Pro Pro Leu Pro Lys Glu Ser Ala Tyr Leu Tyr Ala Arg Phe
            115                 120                 125

Asn Lys Ile Lys Lys Leu Thr Ala Lys Asp Phe Ala Asp Met Pro Asn
130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Thr Leu Ala Glu
                165                 170                 175

Asn Gln Leu Leu Arg Leu Pro Val Leu Pro Pro Lys Leu Thr Leu Leu
            180                 185                 190

Asn Ala Lys His Asn Lys Ile Lys Ser Lys Gly Ile Lys Ala Asn Thr
            195                 200                 205

Phe Lys Lys Leu Asn Lys Leu Ser Phe Leu Tyr Leu Asp His Asn Asp
210                 215                 220

Leu Glu Ser Val Pro Pro Asn Leu Pro Glu Ser Leu Arg Val Ile His
225                 230                 235                 240

Leu Gln Phe Asn Ser Ile Ser Ser Leu Thr Asp Asp Thr Phe Cys Lys
            245                 250                 255

Ala Asn Asp Thr Arg Tyr Ile Arg Glu Arg Ile Glu Glu Ile Arg Leu
            260                 265                 270

Glu Gly Asn Pro Ile Ala Leu Gly Lys His Pro Asn Ser Phe Ile Cys
            275                 280                 285

Leu Lys Arg Leu Pro Ile Gly Ser Tyr Phe
            290                 295

<210> SEQ ID NO 34
<211> LENGTH: 298
<212> TYPE: PRT
<213> ORGANISM: Homo sapiens

<400> SEQUENCE: 34

Met Lys Thr Leu Gln Ser Thr Leu Leu Leu Leu Leu Val Pro Leu
 1               5                  10                  15

Ile Lys Pro Ala Pro Thr Gln Gln Asp Ser Arg Ile Ile Tyr Asp
             20                  25                  30

Tyr Gly Thr Asp Asn Phe Glu Glu Ser Ile Phe Ser Gln Asp Tyr Glu
             35                  40                  45

Asp Lys Tyr Leu Asp Gly Lys Asn Ile Lys Glu Lys Glu Thr Val Ile
 50                  55                  60

Ile Pro Asn Glu Lys Ser Leu Gln Leu Gln Lys Asp Glu Ala Ile Thr
 65                  70                  75                  80

Pro Leu Pro Pro Lys Lys Glu Asn Asp Glu Met Pro Thr Cys Leu Leu

```
                85                  90                  95
Cys Val Cys Leu Ser Gly Ser Val Tyr Cys Glu Glu Val Asp Ile Asp
        100                 105                 110

Ala Val Pro Pro Leu Pro Lys Glu Ser Ala Tyr Leu Tyr Ala Arg Phe
        115                 120                 125

Asn Lys Ile Lys Lys Leu Thr Ala Lys Asp Phe Ala Asp Ile Pro Asn
        130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
                180                 185                 190

Asn Ala Lys Tyr Asn Lys Ile Lys Ser Arg Gly Ile Lys Ala Asn Ala
                195                 200                 205

Phe Lys Lys Leu Asn Asn Leu Thr Phe Leu Tyr Leu Asp His Asn Ala
        210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
                260                 265                 270

Glu Gly Asn Pro Ile Val Leu Gly Lys His Pro Asn Ser Phe Ile Cys
        275                 280                 285

Leu Lys Arg Leu Pro Ile Gly Ser Tyr Phe
        290                 295

<210> SEQ ID NO 35
<211> LENGTH: 13
<212> TYPE: PRT
<213> ORGANISM: artificial sequence
<220> FEATURE:
<223> OTHER INFORMATION: osteoglycin fragment

<400> SEQUENCE: 35

Cys Leu Leu Cys Val Cys Leu Ser Gly Ser Val Tyr Cys
1               5                   10

<210> SEQ ID NO 36
<211> LENGTH: 30
<212> TYPE: PRT
<213> ORGANISM: artificial sequence
<220> FEATURE:
<223> OTHER INFORMATION: 86-115 osteoglycin

<400> SEQUENCE: 36

Lys Glu Asn Asp Glu Met Pro Thr Cys Leu Leu Cys Val Cys Leu Ser
1               5                   10                  15

Gly Ser Val Tyr Cys Glu Glu Val Asp Ile Asp Ala Val Pro
            20                  25                  30

<210> SEQ ID NO 37
<211> LENGTH: 328
<212> TYPE: PRT
<213> ORGANISM: Mus musculus

<400> SEQUENCE: 37

Met Lys Phe Leu Ala Phe Leu Ser Leu Leu Ser Leu Val Leu Gln Lys
```

```
            1               5                  10                 15
        Ala Glu Thr Ala Ser Leu Leu Gly Glu Arg Glu Arg Glu Gln Ser
                        20                 25                 30

Pro Glu Glu Gly Asp Thr Tyr Ala Ser Leu Tyr Val Gly Asn His Thr
                        35                 40                 45

Leu Ser Ile Glu Asp Tyr Asn Glu Val Ile Asp Leu Ser Asn Tyr Glu
         50                 55                 60

Glu Leu Ala Asp Tyr Gly Asp Gln Ile Pro Glu Ala Lys Ile Ser Asn
         65                 70                 75                 80

Leu Thr Leu Pro Thr Arg Thr Ser Pro Thr Ser Thr Val Ala Gln Lys
                        85                 90                 95

Thr Leu Ser Pro Asn Leu Thr Met Ala Val Pro Thr Thr Thr Gly Leu
                        100                105                110

Leu Asn Ser Gln Ser Ser His Gly Leu Pro Thr Cys Leu Val Cys Val
                        115                120                125

Cys Leu Gly Ser Ser Val Tyr Cys Asp Asp Ala Asp Leu Glu Asn Ile
                        130                135                140

Pro Pro Leu Pro Gln Met Thr Thr Tyr Leu Tyr Ala Arg Phe Asn His
        145                 150                155                160

Ile Ser His Ile Gln Ala Gly Asp Phe Lys Gly Leu Thr Lys Leu Arg
                        165                170                175

Arg Ile Asp Leu Ser Gly Asn Ser Ile Ser Ser Ile His Asn Asp Ala
                        180                185                190

Leu Arg Leu Leu Pro Ala Leu Gln Asp Leu Ile Leu Pro Glu Asn Gln
                        195                200                205

Leu Ala Ala Leu Pro Val Leu Pro Ser Gly Ile Glu Phe Leu Asp Val
        210                 215                220

Arg Leu Asn Arg Leu Gln Ser Ser Gly Ile Gln Pro Glu Ala Phe Val
        225                 230                235                240

Ala Leu Lys Lys Leu Gln Phe Leu Tyr Leu Ala Asn Asn Met Leu Asp
                        245                250                255

Ser Ile Pro Gly Pro Leu Pro Leu Ser Leu Arg Ser Leu His Leu Gln
                        260                265                270

Asn Asn Met Ile Glu Thr Met Glu Ser Asp Thr Phe Cys Asp Thr Gly
                        275                280                285

Glu His Arg His Glu Arg Arg Gln Leu Glu Asp Ile Arg Leu Asp Gly
                        290                295                300

Asn Pro Ile Asn Leu Ser Leu Phe Pro Glu Ala Tyr Phe Cys Leu Pro
        305                 310                315                320

Arg Leu Pro Val Gly His Phe Thr
                        325

<210> SEQ ID NO 38
<211> LENGTH: 332
<212> TYPE: PRT
<213> ORGANISM: Homo sapiens

<400> SEQUENCE: 38

Met Arg Leu Leu Ala Phe Leu Ser Leu Leu Ala Leu Val Leu Gln Glu
        1                   5                  10                 15

Thr Gly Thr Ala Ser Leu Pro Arg Lys Glu Arg Lys Arg Arg Glu Glu
                        20                 25                 30

Gln Met Pro Arg Glu Gly Asp Ser Phe Glu Val Leu Pro Leu Arg Asn
                        35                 40                 45
```

```
Asp Val Leu Asn Pro Asp Asn Tyr Gly Glu Val Ile Asp Leu Ser Asn
 50                  55                  60

Tyr Glu Glu Leu Thr Asp Tyr Gly Asp Gln Leu Pro Glu Val Lys Val
 65                  70                  75                  80

Thr Ser Leu Ala Pro Ala Thr Ser Ile Ser Pro Ala Lys Ser Thr Thr
                 85                  90                  95

Ala Pro Gly Thr Pro Ser Ser Asn Pro Thr Met Thr Arg Pro Thr Thr
            100                 105                 110

Ala Gly Leu Leu Leu Ser Ser Gln Pro Asn His Gly Leu Pro Thr Cys
            115                 120                 125

Leu Val Cys Val Cys Leu Gly Ser Ser Val Tyr Cys Asp Asp Ile Asp
130                 135                 140

Leu Glu Asp Ile Pro Leu Pro Arg Arg Thr Ala Tyr Leu Tyr Ala
145                 150                 155                 160

Arg Phe Asn Arg Ile Ser Arg Ile Arg Ala Glu Asp Phe Lys Gly Leu
                165                 170                 175

Thr Lys Leu Lys Arg Ile Asp Leu Ser Asn Asn Leu Ile Ser Ser Ile
            180                 185                 190

Asp Asn Asp Ala Phe Arg Leu Leu His Ala Leu Gln Asp Leu Ile Leu
            195                 200                 205

Pro Glu Asn Gln Leu Glu Ala Leu Pro Val Leu Pro Ser Gly Ile Glu
210                 215                 220

Phe Leu Asp Val Arg Leu Asn Arg Leu Gln Ser Ser Gly Ile Gln Pro
225                 230                 235                 240

Ala Ala Phe Arg Ala Met Glu Lys Leu Gln Phe Leu Tyr Leu Ser Asp
                245                 250                 255

Asn Leu Leu Asp Ser Ile Pro Gly Pro Leu Pro Leu Ser Leu Arg Ser
            260                 265                 270

Val His Leu Gln Asn Asn Leu Ile Glu Thr Met Gln Arg Asp Val Phe
            275                 280                 285

Cys Asp Pro Glu Glu His Lys His Thr Arg Arg Gln Leu Glu Asp Ile
            290                 295                 300

Arg Leu Asp Gly Asn Pro Ile Asn Leu Ser Leu Phe Pro Ser Ala Tyr
305                 310                 315                 320

Phe Cys Leu Pro Arg Leu Pro Ile Gly Arg Phe Thr
                325                 330

<210> SEQ ID NO 39
<211> LENGTH: 13
<212> TYPE: PRT
<213> ORGANISM: artificial sequence
<220> FEATURE:
<223> OTHER INFORMATION: opticin fragment

<400> SEQUENCE: 39

Cys Leu Val Cys Val Cys Leu Gly Ser Ser Val Tyr Cys
1               5                   10

<210> SEQ ID NO 40
<211> LENGTH: 32
<212> TYPE: PRT
<213> ORGANISM: artificial sequence
<220> FEATURE:
<223> OTHER INFORMATION: 114-145 mouse opticin

<400> SEQUENCE: 40

Asn Ser Gln Ser Ser His Gly Leu Pro Thr Cys Leu Val Cys Val Cys
1               5                   10                  15
```

```
Leu Gly Ser Ser Val Tyr Cys Asp Asp Ala Asp Leu Glu Asn Ile Pro
            20                  25                  30
```

<210> SEQ ID NO 41
<211> LENGTH: 32
<212> TYPE: PRT
<213> ORGANISM: artificial sequence
<220> FEATURE:
<223> OTHER INFORMATION: 118-149 human opticin

<400> SEQUENCE: 41

```
Ser Ser Gln Pro Asn His Gly Leu Pro Thr Cys Leu Val Cys Val Cys
1               5                   10                  15

Leu Gly Ser Ser Val Tyr Cys Asp Asp Ile Asp Leu Glu Asp Ile Pro
            20                  25                  30
```

<210> SEQ ID NO 42
<211> LENGTH: 358
<212> TYPE: PRT
<213> ORGANISM: Mus musculus

<400> SEQUENCE: 42

```
Met Ala Arg Ala Leu Leu Phe Ser Leu Val Phe Leu Ala Ile Leu Leu
1               5                   10                  15

Pro Ala Leu Ala Ala Cys Pro Gln Asn Cys His Cys His Gly Asp Leu
            20                  25                  30

Gln His Val Ile Cys Asp Lys Val Gly Leu Gln Lys Ile Pro Lys Val
        35                  40                  45

Ser Glu Thr Thr Lys Leu Leu Asn Leu Gln Arg Asn Asn Phe Pro Val
    50                  55                  60

Leu Ala Ala Asn Ser Phe Arg Thr Met Pro Asn Leu Val Ser Leu His
65                  70                  75                  80

Leu Gln His Cys Asn Ile Arg Glu Val Ala Ala Gly Ala Phe Arg Gly
                85                  90                  95

Leu Lys Gln Leu Ile Tyr Leu Tyr Leu Ser His Asn Asp Ile Arg Val
            100                 105                 110

Leu Arg Ala Gly Ala Phe Asp Asp Leu Thr Glu Leu Thr Tyr Leu Tyr
        115                 120                 125

Leu Asp His Asn Lys Val Ser Glu Leu Pro Arg Gly Leu Leu Ser Pro
    130                 135                 140

Leu Val Asn Leu Phe Ile Leu Gln Leu Asn Asn Asn Lys Ile Arg Glu
145                 150                 155                 160

Leu Arg Ala Gly Ala Phe Gln Gly Ala Lys Asp Leu Arg Trp Leu Tyr
                165                 170                 175

Leu Ser Glu Asn Ala Leu Ser Ser Leu Gln Pro Gly Ser Leu Asp Asp
            180                 185                 190

Val Glu Asn Leu Ala Lys Phe His Leu Asp Lys Asn Gln Leu Ser Ser
        195                 200                 205

Tyr Pro Ser Ala Ala Leu Ser Lys Leu Arg Val Val Glu Glu Leu Lys
    210                 215                 220

Leu Ser His Asn Pro Leu Lys Ser Ile Pro Asp Asn Ala Phe Gln Ser
225                 230                 235                 240

Phe Gly Arg Tyr Leu Glu Thr Leu Trp Leu Asp Asn Thr Asn Leu Glu
                245                 250                 255

Lys Phe Ser Asp Ala Ala Phe Ser Gly Val Thr Thr Leu Lys His Val
            260                 265                 270
```

His Leu Asp Asn Asn Arg Leu Asn Gln Leu Pro Ser Ser Phe Pro Phe
                275                 280                 285

Asp Asn Leu Glu Thr Leu Thr Leu Thr Asn Asn Pro Trp Lys Cys Thr
290                 295                 300

Cys Gln Leu Arg Gly Leu Arg Arg Trp Leu Glu Ala Lys Ala Ser Arg
305                 310                 315                 320

Pro Asp Ala Thr Cys Ser Ser Pro Ala Lys Phe Lys Gly Gln Arg Ile
                325                 330                 335

Arg Asp Thr Asp Ala Leu Arg Ser Cys Lys Ser Pro Thr Lys Arg Ser
                340                 345                 350

Lys Lys Ala Gly Arg His
            355

<210> SEQ ID NO 43
<211> LENGTH: 359
<212> TYPE: PRT
<213> ORGANISM: Homo sapiens

<400> SEQUENCE: 43

Met Val Arg Pro Met Leu Leu Ser Leu Gly Leu Leu Ala Gly Leu
1               5                   10                  15

Leu Pro Ala Leu Ala Ala Cys Pro Gln Asn Cys His Cys His Ser Asp
                20                  25                  30

Leu Gln His Val Ile Cys Asp Lys Val Gly Leu Gln Lys Ile Pro Lys
            35                  40                  45

Val Ser Glu Lys Thr Lys Leu Leu Asn Leu Gln Arg Asn Asn Phe Pro
50                  55                  60

Val Leu Ala Ala Asn Ser Phe Arg Ala Met Pro Asn Leu Val Ser Leu
65                  70                  75                  80

His Leu Gln His Cys Gln Ile Arg Glu Val Ala Ala Gly Ala Phe Arg
                85                  90                  95

Gly Leu Lys Gln Leu Ile Tyr Leu Tyr Leu Ser His Asn Asp Ile Arg
            100                 105                 110

Val Val Arg Ala Gly Ala Phe Asp Asp Leu Thr Glu Leu Thr Tyr Leu
        115                 120                 125

Tyr Leu Asp His Asn Lys Val Thr Glu Leu Pro Arg Gly Leu Leu Ser
130                 135                 140

Pro Leu Val Asn Leu Phe Ile Leu Gln Leu Asn Asn Asn Lys Ile Arg
145                 150                 155                 160

Glu Leu Arg Ala Gly Pro Phe Gln Gly Ala Lys Asp Leu Arg Trp Leu
                165                 170                 175

Tyr Leu Ser Glu Asn Ala Leu Ser Ser Leu Gln Pro Gly Ala Leu Asp
            180                 185                 190

Asp Val Glu Asn Leu Ala Lys Phe His Val Asp Arg Asn Gln Leu Ser
        195                 200                 205

Ser Tyr Pro Ser Ala Ala Leu Ser Lys Leu Arg Val Val Glu Glu Leu
210                 215                 220

Lys Leu Ser His Asn Pro Leu Lys Ser Ile Pro Asp Asn Ala Phe Gln
225                 230                 235                 240

Ser Phe Gly Arg Tyr Leu Glu Thr Leu Trp Leu Asp Asn Thr Asn Leu
                245                 250                 255

Glu Lys Phe Ser Asp Gly Ala Phe Leu Gly Val Thr Thr Leu Lys His
            260                 265                 270

Val His Leu Glu Asn Asn Arg Leu Asn Gln Leu Pro Ser Asn Phe Pro
        275                 280                 285

```
Phe Asp Ser Leu Glu Thr Leu Ala Leu Thr Asn Asn Pro Trp Lys Cys
        290                 295                 300
Thr Cys Gln Leu Arg Gly Leu Arg Arg Trp Leu Glu Ala Lys Ala Ser
305                 310                 315                 320
Arg Pro Asp Ala Thr Cys Ala Ser Pro Ala Lys Phe Lys Gly Gln His
                325                 330                 335
Ile Arg Asp Thr Asp Ala Phe Arg Ser Cys Lys Phe Pro Thr Lys Arg
            340                 345                 350
Ser Lys Lys Ala Gly Arg His
        355

<210> SEQ ID NO 44
<211> LENGTH: 16
<212> TYPE: PRT
<213> ORGANISM: artificial sequence
<220> FEATURE:
<223> OTHER INFORMATION: mouse chondroadherin fragment

<400> SEQUENCE: 44

Cys Pro Gln Asn Cys His Cys His Gly Asp Leu Gln His Val Ile Cys
1               5                   10                  15

<210> SEQ ID NO 45
<211> LENGTH: 16
<212> TYPE: PRT
<213> ORGANISM: artificial sequence
<220> FEATURE:
<223> OTHER INFORMATION: human chondroadherin fragment

<400> SEQUENCE: 45

Cys Pro Gln Asn Cys His Cys His Ser Asp Leu Gln His Val Ile Cys
1               5                   10                  15

<210> SEQ ID NO 46
<211> LENGTH: 35
<212> TYPE: PRT
<213> ORGANISM: artificial sequence
<220> FEATURE:
<223> OTHER INFORMATION: 12-46 mouse chondroadherin

<400> SEQUENCE: 46

Leu Ala Ile Leu Leu Pro Ala Leu Ala Ala Cys Pro Gln Asn Cys His
1               5                   10                  15

Cys His Gly Asp Leu Gln His Val Ile Cys Asp Lys Val Gly Leu Gln
            20                  25                  30

Lys Ile Pro
        35

<210> SEQ ID NO 47
<211> LENGTH: 35
<212> TYPE: PRT
<213> ORGANISM: artificial sequence
<220> FEATURE:
<223> OTHER INFORMATION: 13-47 human chondroadherin

<400> SEQUENCE: 47

Leu Ala Gly Leu Leu Pro Ala Leu Ala Ala Cys Pro Gln Asn Cys His
1               5                   10                  15

Cys His Ser Asp Leu Gln His Val Ile Cys Asp Lys Val Gly Leu Gln
            20                  25                  30

Lys Ile Pro
        35
```

<210> SEQ ID NO 48
<211> LENGTH: 476
<212> TYPE: PRT
<213> ORGANISM: Mus musculus

<400> SEQUENCE: 48

```
Met Leu Ile Leu Leu His Ala Val Val Phe Ser Leu Pro Tyr Thr
1               5                   10                  15

Arg Ala Thr Glu Ala Cys Leu Arg Ala Cys Pro Ala Ala Cys Thr Cys
            20                  25                  30

Ser His Val Glu Arg Gly Cys Ser Val Arg Cys Asp Arg Ala Gly Leu
            35                  40                  45

Gln Arg Val Pro Gln Glu Phe Pro Cys Glu Ala Ala Ser Ile Asp Leu
        50                  55                  60

Asp Arg Asn Gly Leu Arg Ile Leu Gly Glu Arg Ala Phe Gly Thr Leu
65                  70                  75                  80

Pro Ser Leu Arg Arg Leu Ser Leu Arg His Asn Asn Leu Ser Phe Ile
                85                  90                  95

Thr Pro Gly Ala Phe Lys Gly Leu Pro Arg Leu Ala Glu Leu Arg Leu
            100                 105                 110

Ala His Asn Gly Glu Leu Arg Tyr Leu His Val Arg Thr Phe Ala Ala
        115                 120                 125

Leu Gly Arg Leu Arg Arg Leu Asp Leu Ala Ala Cys Arg Leu Phe Ser
130                 135                 140

Val Pro Glu Arg Leu Leu Ala Glu Leu Pro Ala Leu Arg Glu Leu Thr
145                 150                 155                 160

Ala Phe Asp Asn Leu Phe Arg Arg Val Pro Gly Ala Leu Arg Gly Leu
                165                 170                 175

Ala Asn Leu Thr His Ala His Phe Glu Arg Ser Arg Ile Glu Ala Val
            180                 185                 190

Ala Ser Gly Ser Leu Leu Gly Met Arg Arg Leu Arg Ser Leu Ser Leu
        195                 200                 205

Gln Ala Asn Arg Val Arg Ala Val His Ala Gly Ala Phe Gly Asp Cys
    210                 215                 220

Gly Ala Leu Glu Asp Leu Leu Leu Asn Asp Asn Leu Leu Ala Thr Leu
225                 230                 235                 240

Pro Ala Ala Ala Phe Arg Gly Leu Arg Arg Leu Arg Thr Leu Asn Leu
                245                 250                 255

Gly Gly Asn Ala Leu Gly Ser Val Ala Arg Ala Trp Phe Ser Asp Leu
            260                 265                 270

Ala Glu Leu Glu Leu Leu Tyr Leu Asp Arg Asn Ser Ile Thr Phe Val
        275                 280                 285

Glu Glu Gly Ala Phe Gln Asn Leu Ser Gly Leu Leu Ala Leu His Leu
    290                 295                 300

Asn Gly Asn Arg Leu Thr Val Leu Ser Trp Ala Ala Phe Gln Pro Gly
305                 310                 315                 320

Phe Phe Leu Gly Arg Leu Phe Leu Phe Arg Asn Pro Trp Arg Cys Asp
                325                 330                 335

Cys Gln Leu Glu Trp Leu Arg Asp Trp Met Glu Gly Ser Gly Arg Val
            340                 345                 350

Ala Asp Val Ala Cys Ala Ser Pro Gly Ser Val Ala Gly Gln Asp Leu
        355                 360                 365

Ser Gln Val Val Phe Glu Arg Ser Ser Asp Gly Leu Cys Val Asp Pro
```

```
                    370                 375                 380
Asp Glu Leu Asn Phe Thr Thr Ser Ser Pro Gly Pro Ser Pro Glu Pro
385                 390                 395                 400

Val Ala Thr Thr Val Ser Arg Phe Ser Ser Leu Leu Ser Lys Leu Leu
                    405                 410                 415

Ala Pro Arg Ala Pro Val Glu Val Ala Asn Thr Thr Trp Glu Leu
            420                 425                 430

Val Asn Val Ser Leu Asn Asp Ser Phe Arg Ser His Ala Val Met Val
        435                 440                 445

Phe Cys Tyr Lys Ala Thr Phe Leu Phe Thr Ser Cys Val Leu Leu Ser
    450                 455                 460

Leu Ala Gln Tyr Val Val Val Gly Leu Gln Arg Glu
465                 470                 475

<210> SEQ ID NO 49
<211> LENGTH: 481
<212> TYPE: PRT
<213> ORGANISM: Homo sapiens

<400> SEQUENCE: 49

Met Lys Gly Arg Gly Met Leu Val Leu Leu His Ala Val Val Leu
1               5                   10                  15

Gly Leu Pro Ser Ala Trp Ala Val Gly Ala Cys Ala Arg Ala Cys Pro
                20                  25                  30

Ala Ala Cys Ala Cys Ser Thr Val Glu Arg Gly Cys Ser Val Arg Cys
            35                  40                  45

Asp Arg Ala Gly Leu Leu Arg Val Pro Ala Glu Pro Cys Glu Ala
50                  55                  60

Val Ser Ile Asp Leu Asp Arg Asn Gly Leu Arg Phe Leu Gly Glu Arg
65                  70                  75                  80

Ala Phe Gly Thr Leu Pro Ser Leu Arg Arg Leu Ser Leu Arg His Asn
                85                  90                  95

Asn Leu Ser Phe Ile Thr Pro Gly Ala Phe Lys Gly Leu Pro Arg Leu
            100                 105                 110

Ala Glu Leu Arg Leu Ala His Asn Gly Asp Leu Arg Tyr Leu His Ala
        115                 120                 125

Arg Thr Phe Ala Ala Leu Ser Arg Leu Arg Arg Leu Asp Leu Ala Ala
    130                 135                 140

Cys Arg Leu Phe Ser Val Pro Glu Arg Leu Leu Ala Glu Leu Pro Ala
145                 150                 155                 160

Leu Arg Glu Leu Ala Ala Phe Asp Asn Leu Phe Arg Arg Val Pro Gly
                165                 170                 175

Ala Leu Arg Gly Leu Ala Asn Leu Thr His Ala His Leu Glu Arg Gly
            180                 185                 190

Arg Ile Glu Ala Val Ala Ser Ser Leu Gln Gly Leu Arg Arg Leu
    195                 200                 205

Arg Ser Leu Ser Leu Gln Ala Asn Arg Val Arg Ala Val His Ala Gly
    210                 215                 220

Ala Phe Gly Asp Cys Gly Val Leu Glu His Leu Leu Leu Asn Asp Asn
225                 230                 235                 240

Leu Leu Ala Glu Leu Pro Ala Asp Ala Phe Arg Gly Leu Arg Arg Leu
                245                 250                 255

Arg Thr Leu Asn Leu Gly Gly Asn Ala Leu Asp Arg Val Ala Arg Ala
            260                 265                 270
```

```
Trp Phe Ala Asp Leu Ala Glu Leu Glu Leu Tyr Leu Asp Arg Asn
            275                 280                 285
Ser Ile Ala Phe Val Glu Glu Gly Ala Phe Gln Asn Leu Ser Gly Leu
    290                 295                 300
Leu Ala Leu His Leu Asn Gly Asn Arg Leu Thr Val Leu Ala Trp Val
305                 310                 315                 320
Ala Phe Gln Pro Gly Phe Phe Leu Gly Arg Leu Phe Leu Phe Arg Asn
            325                 330                 335
Pro Trp Cys Cys Asp Cys Arg Leu Glu Trp Leu Arg Asp Trp Met Glu
            340                 345                 350
Gly Ser Gly Arg Val Thr Asp Val Pro Cys Ala Ser Pro Gly Ser Val
            355                 360                 365
Ala Gly Leu Asp Leu Ser Gln Val Thr Phe Gly Arg Ser Ser Asp Gly
            370                 375                 380
Leu Cys Val Asp Pro Glu Glu Leu Asn Leu Thr Thr Ser Ser Pro Gly
385                 390                 395                 400
Pro Ser Pro Glu Pro Ala Ala Thr Thr Val Ser Arg Phe Ser Ser Leu
            405                 410                 415
Leu Ser Lys Leu Leu Ala Pro Arg Val Pro Val Glu Glu Ala Ala Asn
            420                 425                 430
Thr Thr Gly Gly Leu Ala Asn Ala Ser Leu Ser Asp Ser Leu Ser Ser
            435                 440                 445
Arg Gly Val Gly Gly Ala Gly Arg Gln Pro Trp Phe Leu Leu Ala Ser
            450                 455                 460
Cys Leu Leu Pro Ser Val Ala Gln His Val Val Phe Gly Leu Gln Met
465                 470                 475                 480
Asp

<210> SEQ ID NO 50
<211> LENGTH: 22
<212> TYPE: PRT
<213> ORGANISM: artificial sequence
<220> FEATURE:
<223> OTHER INFORMATION: mouse nyctalopin fragment

<400> SEQUENCE: 50

Cys Leu Arg Ala Cys Pro Ala Ala Cys Thr Cys Ser His Val Glu Arg
1               5                   10                  15

Gly Cys Ser Val Arg Cys
            20

<210> SEQ ID NO 51
<211> LENGTH: 22
<212> TYPE: PRT
<213> ORGANISM: artificial sequence
<220> FEATURE:
<223> OTHER INFORMATION: human nyctalopin fragment

<400> SEQUENCE: 51

Cys Ala Arg Ala Cys Pro Ala Ala Cys Ala Cys Ser Thr Val Glu Arg
1               5                   10                  15

Gly Cys Ser Val Arg Cys
            20

<210> SEQ ID NO 52
<211> LENGTH: 38
<212> TYPE: PRT
<213> ORGANISM: artificial sequence
<220> FEATURE:
```

<223> OTHER INFORMATION: 15-52 mouse nyctalopin

<400> SEQUENCE: 52

Tyr Thr Arg Ala Thr Glu Ala Cys Leu Arg Ala Cys Pro Ala Ala Cys
1               5                   10                  15

Thr Cys Ser His Val Glu Arg Gly Cys Ser Val Arg Cys Asp Arg Ala
            20                  25                  30

Gly Leu Gln Arg Val Pro
        35

<210> SEQ ID NO 53
<211> LENGTH: 38
<212> TYPE: PRT
<213> ORGANISM: artificial sequence
<220> FEATURE:
<223> OTHER INFORMATION: 20-57 human nyctalopin

<400> SEQUENCE: 53

Ser Ala Trp Ala Val Gly Ala Cys Ala Arg Ala Cys Pro Ala Ala Cys
1               5                   10                  15

Ala Cys Ser Thr Val Glu Arg Gly Cys Ser Val Arg Cys Asp Arg Ala
            20                  25                  30

Gly Leu Leu Arg Val Pro
        35

<210> SEQ ID NO 54
<211> LENGTH: 354
<212> TYPE: PRT
<213> ORGANISM: Mus musculus

<400> SEQUENCE: 54

Met Leu Cys Ser Leu Phe Leu Leu Leu Ala Val Gly Arg Val Gln
1               5                   10                  15

Thr Thr Arg Pro Cys Phe Pro Gly Cys Gln Cys Glu Glu Thr Phe
            20                  25                  30

Gly Leu Phe Asp Ser Phe Ser Leu Ile Arg Val Asp Cys Ser Ser Leu
        35                  40                  45

Gly Pro His Ile Val Pro Val Pro Ile Pro Leu Asp Thr Ala His Leu
    50                  55                  60

Asp Leu Ser Ser Asn Arg Leu Glu Thr Val Asn Glu Ser Val Leu Ala
65                  70                  75                  80

Gly Pro Gly Tyr Thr Thr Leu Ala Gly Leu Asp Leu Ser Tyr Asn Leu
                85                  90                  95

Leu Thr Ser Ile Met Pro Ser Ala Phe Ser Arg Leu Arg Tyr Leu Glu
            100                 105                 110

Ser Leu Asp Leu Ser His Asn Gly Leu Ala Ala Leu Pro Ala Glu Ile
        115                 120                 125

Phe Thr Ser Ser Pro Leu Ser Asp Ile Asn Leu Ser His Asn Arg Leu
    130                 135                 140

Arg Glu Val Ser Ile Ser Ala Phe Thr Thr His Ser Gln Gly Arg Ala
145                 150                 155                 160

Leu His Val Asp Leu Ser His Asn Leu Ile His Arg Leu Pro His
                165                 170                 175

Pro Ala Arg Ala Ser Leu Pro Ala Pro Thr Ile Gln Ser Leu Asn Leu
            180                 185                 190

Ser Trp Asn Arg Phe Arg Ala Val Pro Asp Leu Arg Asp Leu Pro Leu
        195                 200                 205

```
Arg Tyr Leu Ser Leu Asp Gly Asn Pro Leu Ala Thr Ile Asn Pro Asp
    210                 215                 220

Ala Phe Met Gly Leu Ala Gly Leu Thr His Leu Ser Leu Ala Ser Leu
225                 230                 235                 240

Gln Gly Ile Leu His Leu Pro Pro His Gly Phe Arg Glu Leu Pro Gly
                245                 250                 255

Leu Gln Val Leu Asp Leu Ser Gly Asn Pro Lys Leu Lys Trp Ala Gly
            260                 265                 270

Ala Glu Val Phe Ser Gly Leu Leu Gln Glu Leu Asp Leu Ser
        275                 280                 285

Gly Ser Ser Leu Val Pro Leu Pro Glu Met Leu Leu His His Leu Pro
290                 295                 300

Ala Leu Gln Ser Val Ser Val Gly Gln Asp Val Gln Cys Arg Arg Leu
305                 310                 315                 320

Val Arg Glu Gly Ala Tyr His Arg Gln Pro Gly Ser Ser Pro Lys Val
                325                 330                 335

Val Leu His Cys Gly Asp Thr Gln Glu Ser Ala Ala Arg Gly Pro Asp
                340                 345                 350

Ile Leu

<210> SEQ ID NO 55
<211> LENGTH: 353
<212> TYPE: PRT
<213> ORGANISM: Homo sapiens

<400> SEQUENCE: 55

Met Pro Trp Pro Leu Leu Leu Leu Leu Ala Val Ser Gly Ala Gln Thr
1               5                   10                  15

Thr Arg Pro Cys Phe Pro Gly Cys Gln Cys Glu Val Glu Thr Phe Gly
                20                  25                  30

Leu Phe Asp Ser Phe Ser Leu Thr Arg Val Asp Cys Ser Gly Leu Gly
            35                  40                  45

Pro His Ile Met Pro Val Pro Ile Pro Leu Asp Thr Ala His Leu Asp
50                  55                  60

Leu Ser Ser Asn Arg Leu Glu Met Val Asn Glu Ser Val Leu Ala Gly
65                  70                  75                  80

Pro Gly Tyr Thr Thr Leu Ala Gly Leu Asp Leu Ser His Asn Leu Leu
                85                  90                  95

Thr Ser Ile Ser Pro Thr Ala Phe Ser Arg Leu Arg Tyr Leu Glu Ser
                100                 105                 110

Leu Asp Leu Ser His Asn Gly Leu Thr Ala Leu Pro Ala Glu Ser Phe
            115                 120                 125

Thr Ser Ser Pro Leu Ser Asp Val Asn Leu Ser His Asn Gln Leu Arg
130                 135                 140

Glu Val Ser Val Ser Ala Phe Thr Thr His Ser Gln Gly Arg Ala Leu
145                 150                 155                 160

His Val Asp Leu Ser His Asn Leu Ile His Arg Leu Val Pro His Pro
                165                 170                 175

Thr Arg Ala Gly Leu Pro Ala Pro Thr Ile Gln Ser Leu Asn Leu Ala
            180                 185                 190

Trp Asn Arg Leu His Ala Val Pro Asn Leu Arg Asp Leu Pro Leu Arg
        195                 200                 205

Tyr Leu Ser Leu Asp Gly Asn Pro Leu Ala Val Ile Gly Pro Gly Ala
    210                 215                 220
```

```
Phe Ala Gly Leu Gly Gly Leu Thr His Leu Ser Leu Ala Ser Leu Gln
225                 230                 235                 240

Arg Leu Pro Glu Leu Ala Pro Ser Gly Phe Arg Glu Leu Pro Gly Leu
            245                 250                 255

Gln Val Leu Asp Leu Ser Gly Asn Pro Lys Leu Asn Trp Ala Gly Ala
        260                 265                 270

Glu Val Phe Ser Gly Leu Ser Ser Leu Gln Glu Leu Asp Leu Ser Gly
    275                 280                 285

Thr Asn Leu Val Pro Leu Pro Glu Ala Leu Leu Leu His Leu Pro Ala
290                 295                 300

Leu Gln Ser Val Ser Val Gly Gln Asp Val Arg Cys Arg Arg Leu Val
305                 310                 315                 320

Arg Glu Gly Thr Tyr Pro Arg Arg Pro Gly Ser Ser Pro Lys Val Ala
                325                 330                 335

Leu His Cys Val Asp Thr Arg Asp Ser Ala Ala Arg Gly Pro Thr Ile
            340                 345                 350

Leu

<210> SEQ ID NO 56
<211> LENGTH: 25
<212> TYPE: PRT
<213> ORGANISM: artificial sequence
<220> FEATURE:
<223> OTHER INFORMATION: mouse tsukushi fragment

<400> SEQUENCE: 56

Cys Phe Pro Gly Cys Gln Cys Glu Glu Glu Thr Phe Gly Leu Phe Asp
1               5                   10                  15

Ser Phe Ser Leu Ile Arg Val Asp Cys
            20                  25

<210> SEQ ID NO 57
<211> LENGTH: 24
<212> TYPE: PRT
<213> ORGANISM: artificial sequence
<220> FEATURE:
<223> OTHER INFORMATION: human tsukushi fragment

<400> SEQUENCE: 57

Cys Phe Pro Gly Cys Gln Cys Glu Val Glu Thr Phe Gly Leu Phe Asp
1               5                   10                  15

Ser Phe Ser Leu Thr Arg Val Asp
            20

<210> SEQ ID NO 58
<211> LENGTH: 41
<212> TYPE: PRT
<213> ORGANISM: artificial sequence
<220> FEATURE:
<223> OTHER INFORMATION: 14-54 mouse tsukushi

<400> SEQUENCE: 58

Arg Val Gln Thr Thr Arg Pro Cys Phe Pro Gly Cys Gln Cys Glu Glu
1               5                   10                  15

Glu Thr Phe Gly Leu Phe Asp Ser Phe Ser Leu Ile Arg Val Asp Cys
            20                  25                  30

Ser Ser Leu Gly Pro His Ile Val Pro
        35                  40

<210> SEQ ID NO 59
```

```
<211> LENGTH: 41
<212> TYPE: PRT
<213> ORGANISM: artificial sequence
<220> FEATURE:
<223> OTHER INFORMATION: 13-53 human tsukushi

<400> SEQUENCE: 59

Gly Ala Gln Thr Thr Arg Pro Cys Phe Pro Gly Cys Gln Cys Glu Val
1               5                   10                  15

Glu Thr Phe Gly Leu Phe Asp Ser Phe Ser Leu Thr Arg Val Asp Cys
            20                  25                  30

Ser Gly Leu Gly Pro His Ile Met Pro
        35                  40

<210> SEQ ID NO 60
<211> LENGTH: 611
<212> TYPE: PRT
<213> ORGANISM: Mus musculus

<400> SEQUENCE: 60

Met Ala Gly Ser Arg Gly Leu Pro Leu Leu Leu Val Leu Gln Leu
1               5                   10                  15

Phe Leu Gly Pro Val Leu Pro Val Arg Ala Pro Val Phe Gly Arg Ser
            20                  25                  30

Asp Thr Pro Thr Leu Ser Pro Glu Glu Asn Glu Phe Val Glu Glu
            35                  40                  45

Asn Gln Pro Val Leu Val Leu Ser Ser Glu Glu Pro Glu Pro Gly Pro
    50                  55                  60

Ala Thr Val Asp Cys Pro Arg Asp Cys Ala Cys Ser Gln Glu Gly Val
65                  70                  75                  80

Val Asp Cys Gly Gly Ile Asp Leu Arg Glu Phe Pro Gly Asp Leu Pro
                85                  90                  95

Glu His Thr Asn His Leu Ser Leu Gln Asn Asn Gln Leu Glu Lys Ile
            100                 105                 110

Tyr Pro Glu Glu Leu Ser Arg Leu Gln Arg Leu Glu Thr Leu Asn Leu
        115                 120                 125

Gln Asn Asn Arg Leu Thr Ser Arg Gly Leu Pro Glu Glu Ala Phe Glu
    130                 135                 140

His Leu Thr Ser Leu Asn Tyr Leu Tyr Leu Ala Asn Asn Lys Leu Thr
145                 150                 155                 160

Leu Ala Pro Arg Phe Leu Pro Asn Ala Leu Ile Ser Val Asp Phe Ala
                165                 170                 175

Ala Asn Tyr Leu Thr Lys Ile Tyr Gly Leu Thr Phe Gly Gln Lys Pro
            180                 185                 190

Asn Leu Arg Ser Val Tyr Leu His Asn Asn Lys Leu Ala Asp Ala Gly
        195                 200                 205

Leu Pro Asp His Met Phe Asn Gly Ser Ser Asn Val Glu Ile Leu Ile
    210                 215                 220

Leu Ser Ser Asn Phe Leu Arg His Val Pro Lys His Leu Pro Pro Ala
225                 230                 235                 240

Leu Tyr Lys Leu His Leu Lys Asn Asn Lys Leu Glu Lys Ile Pro Pro
                245                 250                 255

Gly Ala Phe Ser Glu Leu Ser Asn Leu Arg Glu Leu Tyr Leu Gln Asn
            260                 265                 270

Asn Tyr Leu Thr Asp Glu Gly Leu Asp Asn Glu Thr Phe Trp Lys Leu
        275                 280                 285
```

```
Ser Ser Leu Glu Tyr Leu Asp Leu Ser Ser Asn Asn Leu Ser Arg Val
    290                 295                 300

Pro Ala Gly Leu Pro Arg Ser Leu Val Leu His Leu Glu Lys Asn
305                 310                 315                 320

Ala Ile Gln Ser Val Glu Ala Asp Val Leu Thr Pro Ile Arg Asn Leu
                325                 330                 335

Glu Tyr Leu Leu Leu His Ser Asn Gln Leu Gln Ala Lys Gly Ile His
                340                 345                 350

Pro Leu Ala Phe Gln Gly Leu Lys Lys Leu His Thr Val His Leu Tyr
            355                 360                 365

Asn Asn Ala Leu Glu Arg Val Pro Ser Gly Leu Pro Arg Arg Val Arg
    370                 375                 380

Thr Leu Met Ile Leu His Asn Gln Ile Thr Gly Ile Gly Arg Glu Asp
385                 390                 395                 400

Phe Ala Thr Thr Tyr Phe Leu Glu Glu Leu Asn Leu Ser Tyr Asn Arg
                405                 410                 415

Ile Thr Ser Pro Gln Met His Arg Asp Ala Phe Arg Lys Leu Arg Leu
                420                 425                 430

Leu Arg Ser Leu Asp Leu Ser Gly Asn Arg Leu Gln Thr Leu Pro Pro
            435                 440                 445

Gly Leu Pro Lys Asn Val His Val Leu Lys Val Lys Arg Asn Glu Leu
    450                 455                 460

Ala Ala Leu Ala Arg Gly Ala Leu Ala Gly Met Ala Gln Leu Arg Glu
465                 470                 475                 480

Leu Tyr Leu Thr Gly Asn Arg Leu Arg Ser Arg Ala Leu Gly Pro Arg
                485                 490                 495

Ala Trp Val Asp Leu Ala Gly Leu Gln Leu Leu Asp Ile Ala Gly Asn
                500                 505                 510

Gln Leu Thr Glu Val Pro Glu Gly Leu Pro Pro Ser Leu Glu Tyr Leu
            515                 520                 525

Tyr Leu Gln Asn Asn Lys Ile Ser Ala Val Pro Ala Asn Ala Phe Asp
    530                 535                 540

Ser Thr Pro Asn Leu Lys Gly Ile Phe Leu Arg Phe Asn Lys Leu Ala
545                 550                 555                 560

Val Gly Ser Val Val Glu Ser Ala Phe Arg Arg Leu Lys His Leu Gln
                565                 570                 575

Val Leu Asp Ile Glu Gly Asn Phe Glu Phe Gly Asn Gly Ser Lys Asp
                580                 585                 590

Lys Asp Glu Glu Glu Glu Glu Glu Glu Glu Glu Asp Glu Glu Glu
            595                 600                 605

Glu Thr Arg
    610

<210> SEQ ID NO 61
<211> LENGTH: 613
<212> TYPE: PRT
<213> ORGANISM: Homo sapiens

<400> SEQUENCE: 61

Met Ala Gln Ser Arg Val Leu Leu Leu Leu Leu Leu Pro Pro Gln
1               5                   10                  15

Leu His Leu Gly Pro Val Leu Ala Val Arg Ala Pro Gly Phe Gly Arg
                20                  25                  30

Ser Gly Gly His Ser Leu Ser Pro Glu Glu Asn Glu Phe Ala Glu Glu
            35                  40                  45
```

```
Glu Pro Val Leu Val Leu Ser Pro Glu Glu Gly Pro Gly Pro Ala
    50                  55                  60

Ala Val Ser Cys Pro Arg Asp Cys Ala Cys Ser Gln Glu Gly Val Val
65                  70                  75                  80

Asp Cys Gly Gly Ile Asp Leu Arg Glu Phe Pro Gly Asp Leu Pro Glu
                85                  90                  95

His Thr Asn His Leu Ser Leu Gln Asn Asn Gln Leu Glu Lys Ile Tyr
            100                 105                 110

Pro Glu Glu Leu Ser Arg Leu His Arg Leu Glu Thr Leu Asn Leu Gln
        115                 120                 125

Asn Asn Arg Leu Thr Ser Arg Gly Leu Pro Glu Lys Ala Phe Glu His
    130                 135                 140

Leu Thr Asn Leu Asn Tyr Leu Tyr Leu Ala Asn Asn Lys Leu Thr Leu
145                 150                 155                 160

Ala Pro Arg Phe Leu Pro Asn Ala Leu Ile Ser Val Asp Phe Ala Ala
                165                 170                 175

Asn Tyr Leu Thr Lys Ile Tyr Gly Leu Thr Phe Gly Gln Lys Pro Asn
            180                 185                 190

Leu Arg Ser Val Tyr Leu His Asn Asn Lys Leu Ala Asp Ala Gly Leu
        195                 200                 205

Pro Asp Asn Met Phe Asn Gly Ser Ser Asn Val Glu Val Leu Ile Leu
    210                 215                 220

Ser Ser Asn Phe Leu Arg His Val Pro Lys His Leu Pro Pro Ala Leu
225                 230                 235                 240

Tyr Lys Leu His Leu Lys Asn Asn Lys Leu Lys Ile Pro Pro Gly
                245                 250                 255

Ala Phe Ser Glu Leu Ser Ser Leu Arg Glu Leu Tyr Leu Gln Asn Asn
            260                 265                 270

Tyr Leu Thr Asp Glu Gly Leu Asp Asn Glu Thr Phe Trp Lys Leu Ser
        275                 280                 285

Ser Leu Glu Tyr Leu Asp Leu Ser Ser Asn Asn Leu Ser Arg Val Pro
    290                 295                 300

Ala Gly Leu Pro Arg Ser Leu Val Leu Leu His Leu Glu Lys Asn Ala
305                 310                 315                 320

Ile Arg Ser Val Asp Ala Asn Val Leu Thr Pro Ile Arg Ser Leu Glu
                325                 330                 335

Tyr Leu Leu Leu His Ser Asn Gln Leu Arg Glu Gln Gly Ile His Pro
            340                 345                 350

Leu Ala Phe Gln Gly Leu Lys Arg Leu His Thr Val His Leu Tyr Asn
        355                 360                 365

Asn Ala Leu Glu Arg Val Pro Ser Gly Leu Pro Arg Arg Val Arg Thr
    370                 375                 380

Leu Met Ile Leu His Asn Gln Ile Thr Gly Ile Gly Arg Glu Asp Phe
385                 390                 395                 400

Ala Thr Thr Tyr Phe Leu Glu Glu Leu Asn Leu Ser Tyr Asn Arg Ile
                405                 410                 415

Thr Ser Pro Gln Val His Arg Asp Ala Phe Arg Lys Leu Arg Leu Leu
            420                 425                 430

Arg Ser Leu Asp Leu Ser Gly Asn Arg Leu His Met Leu Pro Pro Gly
        435                 440                 445

Leu Pro Arg Asn Val His Val Leu Lys Val Lys Arg Asn Glu Leu Ala
    450                 455                 460
```

```
Ala Leu Ala Arg Gly Ala Leu Ala Gly Met Ala Gln Leu Arg Glu Leu
465                 470                 475                 480

Tyr Leu Thr Ser Asn Arg Leu Arg Ser Arg Ala Leu Gly Pro Arg Ala
                485                 490                 495

Trp Val Asp Leu Ala His Leu Gln Leu Leu Asp Ile Ala Gly Asn Gln
            500                 505                 510

Leu Thr Glu Ile Pro Glu Gly Leu Pro Glu Ser Leu Glu Tyr Leu Tyr
        515                 520                 525

Leu Gln Asn Asn Lys Ile Ser Ala Val Pro Ala Asn Ala Phe Asp Ser
    530                 535                 540

Thr Pro Asn Leu Lys Gly Ile Phe Leu Arg Phe Asn Lys Leu Ala Val
545                 550                 555                 560

Gly Ser Val Val Asp Ser Ala Phe Arg Arg Leu Lys His Leu Gln Val
                565                 570                 575

Leu Asp Ile Glu Gly Asn Leu Glu Phe Gly Asp Ile Ser Lys Asp Arg
            580                 585                 590

Gly Arg Leu Gly Lys Glu Lys Glu Glu Glu Glu Glu Glu Glu Glu Glu
        595                 600                 605

Glu Glu Glu Thr Arg
    610
```

<210> SEQ ID NO 62
<211> LENGTH: 15
<212> TYPE: PRT
<213> ORGANISM: artificial sequence
<220> FEATURE:
<223> OTHER INFORMATION: podocan fragment

<400> SEQUENCE: 62

```
Cys Pro Arg Asp Cys Ala Cys Ser Gln Glu Gly Val Val Asp Cys
1               5                   10                  15
```

<210> SEQ ID NO 63
<211> LENGTH: 31
<212> TYPE: PRT
<213> ORGANISM: artificial sequence
<220> FEATURE:
<223> OTHER INFORMATION: 62-92 mouse podocan

<400> SEQUENCE: 63

```
Pro Gly Pro Ala Thr Val Asp Cys Pro Arg Asp Cys Ala Cys Ser Gln
1               5                   10                  15

Glu Gly Val Val Asp Cys Gly Gly Ile Asp Leu Arg Glu Phe Pro
            20                  25                  30
```

<210> SEQ ID NO 64
<211> LENGTH: 31
<212> TYPE: PRT
<213> ORGANISM: artificial sequence
<220> FEATURE:
<223> OTHER INFORMATION: 61-91 human podocan

<400> SEQUENCE: 64

```
Pro Gly Pro Ala Ala Val Ser Cys Pro Arg Asp Cys Ala Cys Ser Gln
1               5                   10                  15

Glu Gly Val Val Asp Cys Gly Gly Ile Asp Leu Arg Glu Phe Pro
            20                  25                  30
```

<210> SEQ ID NO 65
<211> LENGTH: 559
<212> TYPE: PRT

<213> ORGANISM: Mus musculus

<400> SEQUENCE: 65

```
Met Arg Pro Gln Glu Leu Leu Leu Leu Leu Met Leu Lys Trp Ser
1               5                   10                  15

Leu Ala His Thr Glu Asp Pro Ala Phe Pro His Leu Gly Asp Ser Ser
            20                  25                  30

Gln Pro Leu Pro Arg Pro Cys Pro Trp Arg Cys Ser Cys Pro Arg Asp
        35                  40                  45

Asp Thr Val Asp Cys Ala Gly Leu Asp Leu Arg Ile Phe Pro Asp Asn
    50                  55                  60

Ile Thr Arg Ala Ala Arg His Leu Ser Leu Gln Asn Asn Gln Leu Arg
65                  70                  75                  80

Glu Leu Pro Tyr Asn Glu Leu Ser Arg Leu Ser Gly Leu Arg Thr Leu
                85                  90                  95

Asp Leu His Ser Asn Leu Ile Thr Ser Glu Gly Leu Pro Asp Glu Ala
            100                 105                 110

Phe Glu Ser Leu Asn Gln Leu Glu Asn Phe Tyr Val Ala His Asn Lys
        115                 120                 125

Leu Ser Val Ala Pro Gln Phe Leu Pro Arg Ser Leu Arg Val Ala Asp
    130                 135                 140

Leu Ala Ala Asn Glu Val Val Glu Ile Phe Pro Leu Thr Phe Gly Glu
145                 150                 155                 160

Lys Pro Ala Leu Arg Ser Val Tyr Leu His Asn Asn Arg Leu Arg Asn
                165                 170                 175

Thr Gly Leu Pro Pro Asn Thr Phe His Gly Ser Glu Val Ile Thr Thr
            180                 185                 190

Leu Ser Leu Ser Ser Asn Gln Leu Ser Tyr Leu Pro Pro Ser Leu Pro
        195                 200                 205

Ala Ser Leu Glu Arg Leu His Leu Gln Asn Asn Leu Ile Ser Lys Val
    210                 215                 220

Pro Arg Gly Ala Leu Ser Leu Gln Thr His Leu Arg Glu Leu Tyr Leu
225                 230                 235                 240

Gln His Asn Gln Leu Thr Asp Ser Gly Leu Asp Ala Thr Thr Phe Ser
                245                 250                 255

Lys Leu Ser Ser Leu Glu Tyr Leu Asp Leu Ser His Asn Gln Leu Ala
            260                 265                 270

Thr Val Pro Glu Gly Leu Pro Gly Thr Leu Thr Ile Leu His Leu Gly
        275                 280                 285

Arg Asn Cys Ile Arg His Val Glu Ala Val Arg Leu His Lys Ala Arg
    290                 295                 300

Gly Leu Arg Tyr Leu Leu Leu Gln His Asn Lys Leu Gly Ala Ser Ala
305                 310                 315                 320

Leu Pro Lys Gly Thr Leu Arg Pro Leu Arg Ala Leu His Thr Leu His
                325                 330                 335

Leu Tyr Gly Asn Lys Leu Glu Arg Val Pro Pro Ala Leu Pro Arg His
            340                 345                 350

Leu Gln Ala Leu Val Met Pro His Asn His Val Ala Ala Leu Gly Ala
        355                 360                 365

Arg Asp Leu Val Ser Ala Arg Ala Leu Ala Glu Leu Asn Leu Ala Tyr
    370                 375                 380

Asn Ser Leu Ala Ser Ala His Val His Pro Ser Ala Phe Arg Arg Leu
385                 390                 395                 400
```

```
Arg Ala Leu Arg Ser Leu Asp Leu Ala Gly Asn Gln Leu Thr Arg Leu
                405                 410                 415

Pro Glu Gly Leu Pro Ala Ser Leu Arg Ser Leu Arg Leu Gln Arg Asn
            420                 425                 430

Gln Leu Arg Thr Leu Glu Pro Glu Gln Leu Ala Gly Leu Asn Lys Leu
        435                 440                 445

Arg Glu Leu Asn Leu Ala His Asn Arg Leu Arg Val Gly Asp Ile Gly
    450                 455                 460

Pro Gly Thr Trp His Glu Leu Gln Ala Leu Lys Val Leu Asp Leu Ser
465                 470                 475                 480

His Asn Glu Leu Ser Phe Val Pro Pro Asp Leu Pro Glu Ala Leu Glu
                485                 490                 495

Glu Leu Tyr Leu Gln Ala Asn Arg Ile Ser His Val Gly Pro Glu Ala
            500                 505                 510

Phe Leu Ser Thr Pro His Leu Arg Ala Leu Phe Leu Arg Ala Asn Arg
        515                 520                 525

Leu His Met Thr Ser Ile Arg Ala Glu Ala Leu Gln Gly Leu Thr His
    530                 535                 540

Leu Arg Val Val Asp Thr Ala Glu Asn Pro Glu Gln Val Leu Val
545                 550                 555

<210> SEQ ID NO 66
<211> LENGTH: 512
<212> TYPE: PRT
<213> ORGANISM: Homo sapiens

<400> SEQUENCE: 66

Met Ala Glu Ser Gly Leu Ala Met Trp Pro Ser Leu Leu Leu Leu Leu
1               5                   10                  15

Leu Leu Pro Gly Pro Pro Val Ala Gly Leu Glu Asp Ala Ala Phe
            20                  25                  30

Pro His Leu Gly Glu Ser Leu Gln Pro Leu Leu Arg Ala Cys Pro Leu
        35                  40                  45

Arg Cys Ser Cys Pro Arg Val Asp Thr Val Asp Cys Asp Gly Leu Asp
    50                  55                  60

Leu Arg Val Phe Pro Asp Asn Ile Thr Arg Ala Ala Gln His Leu Ser
65                  70                  75                  80

Leu Gln Asn Asn Gln Leu Gln Glu Leu Pro Tyr Asn Glu Leu Ser Arg
                85                  90                  95

Leu Ser Gly Leu Arg Thr Leu Asn Leu His Asn Asn Leu Ile Ser Ser
            100                 105                 110

Glu Gly Leu Pro Asp Glu Ala Phe Glu Ser Leu Thr Gln Leu Gln His
        115                 120                 125

Leu Cys Val Ala His Asn Lys Leu Ser Val Ala Pro Gln Phe Leu Pro
    130                 135                 140

Arg Ser Leu Arg Val Ala Asp Leu Ala Ala Asn Gln Val Met Glu Ile
145                 150                 155                 160

Phe Pro Leu Thr Phe Gly Glu Lys Pro Ala Leu Arg Ser Val Tyr Leu
                165                 170                 175

His Asn Asn Gln Leu Ser Asn Ala Gly Leu Pro Pro Asp Ala Phe Arg
            180                 185                 190

Gly Ser Glu Ala Ile Ala Thr Leu Ser Leu Ser Asn Asn Gln Leu Ser
        195                 200                 205

Tyr Leu Pro Pro Ser Leu Pro Pro Ser Leu Glu Arg Leu His Leu Gln
    210                 215                 220
```

```
Asn Asn Leu Ile Ser Lys Val Pro Arg Gly Ala Leu Ser Arg Gln Thr
225                 230                 235                 240

Gln Leu Arg Glu Leu Tyr Leu Gln His Asn Gln Leu Thr Asp Ser Gly
            245                 250                 255

Leu Asp Ala Thr Thr Phe Ser Lys Leu His Ser Leu Glu Tyr Leu Asp
        260                 265                 270

Leu Ser His Asn Gln Leu Thr Thr Val Pro Ala Gly Leu Pro Arg Thr
    275                 280                 285

Leu Ala Ile Leu His Leu Gly Arg Asn Arg Ile Arg Gln Val Glu Ala
290                 295                 300

Ala Arg Leu His Gly Ala Arg Gly Leu Arg Tyr Leu Leu Leu Gln His
305                 310                 315                 320

Asn Gln Leu Gly Ser Ser Gly Leu Pro Ala Gly Ala Leu Arg Pro Leu
            325                 330                 335

Arg Gly Leu His Thr Leu His Leu Tyr Gly Asn Gly Leu Asp Arg Val
        340                 345                 350

Pro Pro Ala Leu Pro Arg Arg Leu Arg Ala Leu Val Leu Pro His Asn
    355                 360                 365

His Val Ala Ala Leu Gly Ala Arg Asp Leu Val Ala Thr Pro Gly Leu
370                 375                 380

Thr Glu Leu Asn Leu Ala Tyr Asn Arg Leu Ala Ser Ala Arg Val His
385                 390                 395                 400

His Arg Ala Phe Arg Arg Leu Arg Ala Leu Arg Ser Leu Asp Leu Ala
            405                 410                 415

Gly Asn Gln Leu Thr Arg Leu Pro Met Gly Leu Pro Thr Gly Leu Arg
        420                 425                 430

Thr Leu Gln Leu Gln Arg Asn Gln Leu Arg Met Leu Glu Pro Glu Pro
    435                 440                 445

Leu Ala Gly Leu Asp Gln Leu Arg Glu Leu Ser Leu Ala His Asn Arg
450                 455                 460

Leu Arg Val Gly Asp Ile Gly Pro Gly Thr Trp His Glu Leu Gln Ala
465                 470                 475                 480

Leu Gln Val Arg His Arg Leu Val Ser His Thr Val Pro Arg Ala Pro
            485                 490                 495

Pro Ser Pro Cys Leu Pro Cys His Val Pro Asn Ile Leu Val Ser Trp
        500                 505                 510

<210> SEQ ID NO 67
<211> LENGTH: 15
<212> TYPE: PRT
<213> ORGANISM: artificial sequence
<220> FEATURE:
<223> OTHER INFORMATION: mouse podocan-like protein 1 fragment

<400> SEQUENCE: 67

Cys Pro Trp Arg Cys Ser Cys Pro Arg Asp Asp Thr Val Asp Cys
1               5                   10                  15

<210> SEQ ID NO 68
<211> LENGTH: 15
<212> TYPE: PRT
<213> ORGANISM: artificial sequence
<220> FEATURE:
<223> OTHER INFORMATION: human podocan-like protein 1 fragment

<400> SEQUENCE: 68

Cys Pro Leu Arg Cys Ser Cys Pro Arg Val Asp Thr Val Asp Cys
```

<210> SEQ ID NO 69
<211> LENGTH: 34
<212> TYPE: PRT
<213> ORGANISM: artificial sequence
<220> FEATURE:
<223> OTHER INFORMATION: 29-62 mouse podocan-like protein 1

<400> SEQUENCE: 69

Gly Asp Ser Ser Gln Pro Leu Pro Arg Pro Cys Pro Trp Arg Cys Ser
 1               5                  10                  15

Cys Pro Arg Asp Asp Thr Val Asp Cys Ala Gly Leu Asp Leu Arg Ile
            20                  25                  30

Phe Pro

<210> SEQ ID NO 70
<211> LENGTH: 34
<212> TYPE: PRT
<213> ORGANISM: artificial sequence
<220> FEATURE:
<223> OTHER INFORMATION: 36-69 human podocan-like protein 1

<400> SEQUENCE: 70

Gly Glu Ser Leu Gln Pro Leu Leu Arg Ala Cys Pro Leu Arg Cys Ser
 1               5                  10                  15

Cys Pro Arg Val Asp Thr Val Asp Cys Asp Gly Leu Asp Leu Arg Val
            20                  25                  30

Phe Pro

<210> SEQ ID NO 71
<211> LENGTH: 670
<212> TYPE: PRT
<213> ORGANISM: Mus musculus

<400> SEQUENCE: 71

Met Lys Leu Ala Val Leu Phe Cys Phe Ile Leu Leu Ile Val Leu Gln
 1               5                  10                  15

Thr Asp Cys Glu Arg Gly Thr Arg Arg Gln Arg Arg Met His Gln
            20                  25                  30

Arg Arg Leu Arg Lys Ser Ser Ser Phe His Leu Arg Ala Asn Arg Gln
        35                  40                  45

Leu Glu Val Gln Gln Thr Thr Ala Ala Pro Asp Ala Arg Leu Pro Thr
    50                  55                  60

Ala Asn Ser Asp Tyr Ser Val Glu Glu Asn Ile Glu Ser Leu Leu Ser
65                  70                  75                  80

Asn Leu Gly Val Glu Ser Ser Tyr Ser Val Leu Pro Gly Lys Lys Gly
                85                  90                  95

Tyr Cys Phe Val Lys Gly Met Ile Met Tyr Asn Lys Ala Val Trp Ser
            100                 105                 110

Pro Glu Pro Cys Thr Thr Cys Leu Cys Ser Asn Gly Arg Val Leu Cys
        115                 120                 125

Asp Glu Thr Glu Cys His Pro Lys Ala Cys Pro Tyr Thr Ile Lys Pro
    130                 135                 140

Glu Gly Glu Cys Cys Pro Ile Cys Ser Asp Ala Glu Gln Glu Ser Ile
145                 150                 155                 160

Asn Lys Leu His Lys Gln Val Pro Pro Gln Met Glu Met Asp Gln
                165                 170                 175

```
Val Ala Ile Lys Glu Ala Leu Gln Ser Glu Asp Glu Glu Ile Ala
            180                 185                 190

Glu Gly His Lys Glu His Lys Lys Glu Thr Ser Val Pro Thr Lys Ile
        195                 200                 205

His Gly Asp Gly Glu Arg Thr Glu Arg Lys Leu Arg Pro Glu Lys Glu
    210                 215                 220

Gly Arg Ser Ala His Gln Pro Leu Tyr His Gly Arg Arg Glu Glu Glu
225                 230                 235                 240

Glu Ser Lys Glu Glu Thr Glu Arg Glu Gly Glu Glu Glu Glu Glu Glu
            245                 250                 255

Glu Glu Glu Glu Glu Asp Ala Ile Arg Gly Asp Val Phe Arg Met
        260                 265                 270

Ser Ser Arg Val Ile Pro Gly Thr Pro Arg Gly Arg Pro Arg Leu Pro
    275                 280                 285

Arg Ser Cys Ser Leu Ser Tyr Arg Thr Ile Ser Cys Val His Ala Asp
290                 295                 300

Phe Thr Glu Ile Pro Pro Ile Thr Ala Pro Glu Val Thr Asn Leu Glu
305                 310                 315                 320

Leu Val Gly Asn Ser Ile Ile Ser Ile Pro Asp Glu Ala Phe Asn Gly
                325                 330                 335

Leu Pro Asn Leu Glu Arg Leu Asp Leu Ser Arg Asn Asn Ile Thr Ser
            340                 345                 350

Ser Gly Ile Gly Pro Lys Ala Phe Lys Ser Leu Lys Lys Leu Met Arg
        355                 360                 365

Leu Asn Met Asp Gly Asn Asn Leu Val His Ile Pro Ser Asp Leu Pro
    370                 375                 380

Ser Thr Leu Glu Glu Leu Lys Ile Asn Asp Asn Asn Leu Gln Ala Ile
385                 390                 395                 400

Asp Glu Lys Ser Leu Ser Leu Asn Gln Leu Val Thr Leu Glu Leu
                405                 410                 415

Glu Gly Asn Asn Leu Ser Glu Ile Asn Val Asp Pro Leu Ala Phe Gln
            420                 425                 430

Ser Leu Glu Ser Leu Ser Tyr Leu Arg Leu Gly Arg Asn Lys Phe Arg
        435                 440                 445

Ile Ile Pro Gln Gly Leu Pro Ala Ser Thr Glu Glu Leu Tyr Leu Glu
    450                 455                 460

Asn Asn Gln Ile Glu Glu Ile Thr Glu Ile Cys Phe Asn His Thr Arg
465                 470                 475                 480

Lys Ile Thr Met Ile Ile Leu Arg Tyr Asn Lys Ile Glu Glu Ser Arg
                485                 490                 495

Ile Ala Pro Leu Ala Trp Ile Asn Gln Glu Asn Leu Glu Ser Ile Asp
            500                 505                 510

Leu Ser Tyr Asn Lys Leu Tyr His Val Pro Ser Tyr Leu Pro Lys Ser
        515                 520                 525

Leu Leu His Leu Val Leu Ile Gly Asn Gln Ile Asp Arg Ile Pro Gly
    530                 535                 540

Tyr Val Phe Gly His Met Gln Pro Gly Leu Glu Tyr Leu Tyr Leu Ser
545                 550                 555                 560

Phe Asn Arg Leu Ser Asp Asp Gly Val Asp Leu Val Ser Phe Tyr Gly
                565                 570                 575

Ala Tyr His Ser Leu Arg Glu Leu Phe Leu Asp His Asn Asp Phe Lys
            580                 585                 590

Ser Ile Pro Pro Gly Ile Gln Asp Met Lys Ala Leu His Phe Leu Arg
```

```
                  595                 600                 605
Leu Asn Asn Lys Ile Arg Asn Ile His Pro Glu Gln Ile Cys Asn
    610                 615                 620

Ala Glu Glu Asp Glu Asp Ser Ala Leu Glu His Leu His Leu Glu Asn
625                 630                 635                 640

Asn Tyr Ile Arg Thr Arg Glu Ile Ser Ser Tyr Ala Phe Ser Cys Ile
                    645                 650                 655

Arg Leu Tyr Ser Ser Ile Val Leu Lys Pro Gln His Ile Lys
                660                 665                 670

<210> SEQ ID NO 72
<211> LENGTH: 677
<212> TYPE: PRT
<213> ORGANISM: Homo sapiens

<400> SEQUENCE: 72

Met Lys Ile Ala Val Leu Phe Cys Phe Phe Leu Leu Ile Ile Phe Gln
1               5                   10                  15

Thr Asp Phe Gly Lys Asn Glu Glu Ile Pro Arg Lys Gln Arg Arg Lys
                20                  25                  30

Ile Tyr His Arg Arg Leu Arg Lys Ser Ser Thr Ser His Lys His Arg
            35                  40                  45

Ser Asn Arg Gln Leu Gly Ile Pro Gln Thr Thr Val Phe Thr Pro Val
50                  55                  60

Ala Arg Leu Pro Ile Val Asn Phe Asp Tyr Ser Met Glu Glu Lys Phe
65                  70                  75                  80

Glu Ser Phe Ser Ser Phe Pro Gly Val Glu Ser Ser Tyr Asn Val Leu
                85                  90                  95

Pro Gly Lys Lys Gly His Cys Leu Val Lys Gly Ile Thr Met Tyr Asn
                100                 105                 110

Lys Ala Val Trp Ser Pro Glu Pro Cys Thr Thr Cys Leu Cys Ser Asp
            115                 120                 125

Gly Arg Val Leu Cys Asp Glu Thr Met Cys His Pro Gln Arg Cys Pro
130                 135                 140

Gln Thr Val Ile Pro Glu Gly Glu Cys Cys Pro Val Cys Ser Ala Thr
145                 150                 155                 160

Glu Gln Arg Glu Pro Thr Asn Leu Leu His Lys Gln Leu Pro Pro Pro
                165                 170                 175

Gln Val Gly Met Asp Arg Ile Val Arg Lys Glu Ala Leu Gln Ser Glu
            180                 185                 190

Glu Asp Glu Glu Val Lys Glu Glu Asp Thr Glu Gln Lys Arg Glu Thr
        195                 200                 205

Pro Glu Ser Arg Asn Gln Gly Gln Leu Tyr Ser Glu Gly Asp Ser Arg
    210                 215                 220

Gly Gly Asp Arg Lys Gln Arg Pro Gly Glu Glu Arg Arg Leu Ala His
225                 230                 235                 240

Gln Gln Gln Arg Gln Gly Arg Glu Glu Glu Asp Glu Glu Glu Glu
                245                 250                 255

Gly Glu Glu Gly Glu Glu Asp Glu Glu Asp Glu Glu Asp Pro Val Arg
            260                 265                 270

Gly Asp Met Phe Arg Met Pro Ser Arg Ser Pro Leu Pro Ala Pro Pro
        275                 280                 285

Arg Gly Thr Leu Arg Leu Pro Ser Gly Cys Ser Leu Ser Tyr Arg Thr
    290                 295                 300
```

```
Ile Ser Cys Ile Asn Ala Met Leu Thr Gln Ile Pro Pro Leu Thr Ala
305                 310                 315                 320

Pro Gln Ile Thr Ser Leu Glu Leu Thr Gly Asn Ser Ile Ala Ser Ile
            325                 330                 335

Pro Asp Glu Ala Phe Asn Gly Leu Pro Asn Leu Glu Arg Leu Asp Leu
            340                 345                 350

Ser Lys Asn Asn Ile Thr Ser Ser Gly Ile Gly Pro Lys Ala Phe Lys
            355                 360                 365

Leu Leu Lys Lys Leu Met Arg Ser Asn Met Asp Gly Asn Asn Leu Ile
            370                 375                 380

Gln Ile Pro Ser Gln Leu Pro Ser Thr Leu Glu Glu Leu Lys Val Asn
385                 390                 395                 400

Glu Asn Asn Leu Gln Ala Ile Asp Glu Glu Ser Leu Ser Asp Leu Asn
            405                 410                 415

Gln Leu Val Thr Leu Glu Leu Glu Gly Asn Asn Leu Ser Glu Ala Asn
            420                 425                 430

Val Asn Pro Leu Ala Phe Lys Pro Leu Lys Ser Leu Ala Tyr Leu Arg
            435                 440                 445

Leu Gly Lys Asn Lys Phe Arg Ile Ile Pro Gln Gly Leu Pro Gly Ser
450                 455                 460

Ile Glu Glu Leu Tyr Leu Glu Asn Asn Gln Ile Glu Glu Ile Thr Glu
465                 470                 475                 480

Ile Cys Phe Asn His Thr Arg Lys Ile Asn Val Ile Val Leu Arg Tyr
            485                 490                 495

Asn Lys Ile Glu Glu Asn Arg Ile Ala Pro Leu Ala Trp Ile Asn Gln
            500                 505                 510

Glu Asn Leu Glu Ser Ile Asp Leu Ser Tyr Asn Lys Leu Tyr His Val
            515                 520                 525

Pro Ser Tyr Leu Pro Lys Ser Leu Leu His Leu Val Leu Leu Gly Asn
530                 535                 540

Gln Ile Glu Arg Ile Pro Gly Tyr Val Phe Gly His Met Glu Pro Gly
545                 550                 555                 560

Leu Glu Tyr Leu Tyr Leu Ser Phe Asn Lys Leu Ala Asp Asp Gly Met
            565                 570                 575

Asp Arg Val Ser Phe Tyr Gly Ala Tyr His Ser Leu Arg Glu Leu Phe
            580                 585                 590

Leu Asp His Asn Asp Leu Lys Ser Ile Pro Pro Gly Ile Gln Glu Met
            595                 600                 605

Lys Ala Leu His Phe Leu Arg Leu Asn Asn Asn Lys Ile Arg Asn Ile
610                 615                 620

Leu Pro Glu Glu Ile Cys Asn Ala Glu Glu Asp Asp Ser Asn Leu
625                 630                 635                 640

Glu His Leu His Leu Glu Asn Asn Tyr Ile Lys Ile Arg Glu Ile Pro
            645                 650                 655

Ser Tyr Thr Phe Ser Cys Ile Arg Ser Tyr Ser Ile Val Leu Lys
            660                 665                 670

Pro Gln Asn Ile Lys
        675
```

<210> SEQ ID NO 73
<211> LENGTH: 31
<212> TYPE: PRT
<213> ORGANISM: artificial sequence
<220> FEATURE:
<223> OTHER INFORMATION: 109-139 mouse ECM2

<400> SEQUENCE: 73

Ala Val Trp Ser Pro Glu Pro Cys Thr Thr Cys Leu Cys Ser Asn Gly
1               5                   10                  15

Arg Val Leu Cys Asp Glu Thr Glu Cys His Pro Lys Ala Cys Pro
            20                  25                  30

<210> SEQ ID NO 74
<211> LENGTH: 31
<212> TYPE: PRT
<213> ORGANISM: artificial sequence
<220> FEATURE:
<223> OTHER INFORMATION: 114-144 human ECM2

<400> SEQUENCE: 74

Ala Val Trp Ser Pro Glu Pro Cys Thr Thr Cys Leu Cys Ser Asp Gly
1               5                   10                  15

Arg Val Leu Cys Asp Glu Thr Met Cys His Pro Gln Arg Cys Pro
            20                  25                  30

<210> SEQ ID NO 75
<211> LENGTH: 41
<212> TYPE: PRT
<213> ORGANISM: artificial sequence
<220> FEATURE:
<223> OTHER INFORMATION: 31-71 mouse decorin fragment

<400> SEQUENCE: 75

Asp Glu Ala Ser Gly Ile Ile Pro Tyr Asp Pro Asp Asn Pro Leu Ile
1               5                   10                  15

Ser Met Cys Pro Tyr Arg Cys Gln Cys His Leu Arg Val Val Gln Cys
            20                  25                  30

Ser Asp Leu Gly Leu Asp Lys Val Pro
            35                  40

<210> SEQ ID NO 76
<211> LENGTH: 14
<212> TYPE: PRT
<213> ORGANISM: Artificial Sequence
<220> FEATURE:
<223> OTHER INFORMATION: Pepride fragment capable of binding myostatin
<220> FEATURE:
<221> NAME/KEY: VARIANT
<222> LOCATION: (1)...(14)
<223> OTHER INFORMATION: Xaa = Any Amino Acid

<400> SEQUENCE: 76

Cys Xaa Xaa Xaa Cys Xaa Cys Xaa Xaa Xaa Xaa Xaa Xaa Cys
1               5                   10

<210> SEQ ID NO 77
<211> LENGTH: 17
<212> TYPE: PRT
<213> ORGANISM: Artificial Sequence
<220> FEATURE:
<223> OTHER INFORMATION: Pepride fragment capable of binding myostatin
<220> FEATURE:
<221> NAME/KEY: VARIANT
<222> LOCATION: (1)...(17)
<223> OTHER INFORMATION: Xaa = Any Amino Acid

<400> SEQUENCE: 77

Cys Xaa Xaa Xaa Cys Xaa Cys Xaa Xaa Xaa Xaa Xaa Xaa Xaa Xaa Xaa
1               5                   10                  15

Cys

```
<210> SEQ ID NO 78
<211> LENGTH: 13
<212> TYPE: PRT
<213> ORGANISM: Artificial Sequence
<220> FEATURE:
<223> OTHER INFORMATION: Pepride fragment capable of binding myostatin
<220> FEATURE:
<221> NAME/KEY: VARIANT
<222> LOCATION: (1)...(13)
<223> OTHER INFORMATION: Xaa = Any Amino Acid

<400> SEQUENCE: 78

Cys Xaa Xaa Cys Xaa Cys Xaa Xaa Xaa Xaa Xaa Xaa Cys
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Pepride fragment capable of binding myostatin
<220> FEATURE:
<221> NAME/KEY: VARIANT
<222> LOCATION: (1)...(15)
<223> OTHER INFORMATION: Xaa = Any Amino Acid

<400> SEQUENCE: 79

Cys Xaa Xaa Xaa Cys Xaa Cys Xaa Xaa Xaa Xaa Xaa Xaa Xaa Cys
1               5                   10                  15
```